(12) United States Patent
Daily et al.

(10) Patent No.: US 7,985,216 B2
(45) Date of Patent: Jul. 26, 2011

(54) MEDICINAL CONTAINER ENGAGEMENT AND AUTOMATIC NEEDLE DEVICE

(75) Inventors: David Daily, Herzlia (IL); Lior Raday, D. N. Hof Ashkelon (IL)

(73) Assignee: Dali Medical Devices Ltd., Rishon Le Zion (IL)

( * ) Notice: Subject to any disclaimer, the term of this patent is extended or adjusted under 35 U.S.C. 154(b) by 629 days.

(21) Appl. No.: 10/592,891

(22) PCT Filed: Mar. 15, 2005

(86) PCT No.: PCT/IL2005/000298
§ 371 (c)(1),
(2), (4) Date: Sep. 29, 2008

(87) PCT Pub. No.: WO2005/086587
PCT Pub. Date: Sep. 22, 2005

(65) Prior Publication Data
US 2009/0018506 A1 Jan. 15, 2009

(30) Foreign Application Priority Data
Mar. 16, 2004 (IL) .......................................... 160891

(51) Int. Cl.
- A61M 37/00 (2006.01)
- A61M 5/00 (2006.01)
- A61M 39/00 (2006.01)
- A61M 39/10 (2006.01)
- A61M 25/16 (2006.01)
- A61M 25/18 (2006.01)

(52) U.S. Cl. ........... 604/533; 604/82; 604/131; 604/263
(58) Field of Classification Search .......... 604/131–137, 604/533, 905, 414, 68, 82
See application file for complete search history.

(56) References Cited

U.S. PATENT DOCUMENTS

| | | |
|---|---|---|
| 4,058,121 A | 11/1977 | Choksi et al. |
| 4,333,457 A | 6/1982 | Margulies |
| 4,474,572 A | 10/1984 | McNaughton et al. |
| 4,475,906 A | 10/1984 | Holzner et al. |
| 4,484,910 A | 11/1984 | Sarnoff et al. |
| 4,487,602 A | 12/1984 | Christensen et al. |
| 4,505,710 A | 3/1985 | Collins |
| 4,512,767 A | 4/1985 | Denance et al. |
| 4,515,590 A | 5/1985 | Daniel et al. |
| 4,518,387 A | 5/1985 | Murphy et al. |
| 4,529,401 A | 7/1985 | Leslie et al. |
| 4,529,403 A | 7/1985 | Kamstra et al. |
| 4,530,695 A | 7/1985 | Phillips et al. |

(Continued)

FOREIGN PATENT DOCUMENTS

WO 03047663 6/2003

OTHER PUBLICATIONS

US 5,954,699, Jost, et al. (withdrawn).

Primary Examiner — Nicholas D Lucchesi
Assistant Examiner — Rebecca E Eisenberg
(74) Attorney, Agent, or Firm — Fish & Richardson P.C.

(57) ABSTRACT

A medicinal container engagement and automatic needle device including an automatic needle assembly and a medicinal container receptacle removably joined to the automatic needle assembly.

46 Claims, 53 Drawing Sheets

U.S. PATENT DOCUMENTS

| | | |
|---|---|---|
| 4,534,759 A | 8/1985 | Trawoger et al. |
| 4,543,101 A | 9/1985 | Crouch |
| 4,547,189 A | 10/1985 | Moore, Jr. |
| 4,553,962 A | 11/1985 | Brunet et al. |
| 4,573,970 A | 3/1986 | Wagner et al. |
| 4,573,976 A | 3/1986 | Sampson et al. |
| 4,573,993 A | 3/1986 | Hoag et al. |
| 4,578,061 A | 3/1986 | Lemelson |
| 4,578,064 A | 3/1986 | Sarnoff et al. |
| 4,580,561 A | 4/1986 | Williamson |
| 4,592,742 A | 6/1986 | Landau et al. |
| 4,592,744 A | 6/1986 | Jagger et al. |
| 4,594,073 A | 6/1986 | Stine |
| 4,596,558 A | 6/1986 | Smith et al. |
| 4,597,753 A | 7/1986 | Turley et al. |
| 4,600,403 A | 7/1986 | Wagner et al. |
| 4,601,708 A | 7/1986 | Jordan |
| 4,613,328 A | 9/1986 | Boyd |
| 4,620,540 A | 11/1986 | Goodale |
| 4,620,847 A | 11/1986 | Shishov et al. |
| 4,624,660 A | 11/1986 | Mijers et al. |
| 4,650,468 A | 3/1987 | Jennings, Jr. |
| 4,658,830 A | 4/1987 | Sarnoff |
| 4,659,326 A | 4/1987 | Johnson et al. |
| 4,664,651 A | 5/1987 | Weinshenker et al. |
| 4,664,654 A | 5/1987 | Strauss |
| 4,666,436 A | 5/1987 | McDonald et al. |
| 4,672,967 A | 6/1987 | Smith |
| 4,681,565 A | 7/1987 | Gourlandt et al. |
| 4,685,474 A | 8/1987 | Kurz et al. |
| 4,687,465 A | 8/1987 | Prindle et al. |
| 4,687,467 A | 8/1987 | Cygielski |
| 4,689,042 A | 8/1987 | Sarnoff et al. |
| 4,699,614 A | 10/1987 | Glazier |
| 4,710,170 A | 12/1987 | Haber et al. |
| 4,722,733 A | 2/1988 | Howson |
| 4,723,937 A | 2/1988 | Sarnoff et al. |
| 4,735,618 A | 4/1988 | Hagen |
| 4,738,663 A | 4/1988 | Bogan |
| 4,743,234 A | 5/1988 | Leopoldi et al. |
| 4,744,955 A | 5/1988 | Shapiro |
| 4,745,907 A | 5/1988 | Russel, Jr. et al. |
| 4,747,829 A | 5/1988 | Jacob et al. |
| 4,747,831 A | 5/1988 | Kulli |
| 4,753,636 A | 6/1988 | Free |
| 4,755,169 A | 7/1988 | Sarnoff et al. |
| 4,758,227 A | 7/1988 | Lancaster, Jr. et al. |
| 4,758,230 A | 7/1988 | Rycroft |
| 4,758,231 A | 7/1988 | Haber et al. |
| 4,766,908 A | 8/1988 | Clement |
| 4,767,407 A | 8/1988 | Foran |
| 4,767,413 A | 8/1988 | Haber et al. |
| 4,770,655 A | 9/1988 | Haber et al. |
| 4,781,683 A | 11/1988 | Wozniak et al. |
| 4,781,685 A | 11/1988 | Lehmann et al. |
| 4,781,688 A | 11/1988 | Thoma et al. |
| 4,784,640 A | 11/1988 | Johnson et al. |
| 4,787,384 A | 11/1988 | Campbell et al. |
| 4,787,893 A | 11/1988 | Villette et al. |
| 4,790,823 A | 12/1988 | Charton et al. |
| 4,790,827 A | 12/1988 | Haber et al. |
| 4,795,432 A | 1/1989 | Karczmer |
| 4,795,433 A | 1/1989 | Sarnoff |
| 4,798,587 A | 1/1989 | Willoughby et al. |
| 4,799,921 A | 1/1989 | Johnson et al. |
| 4,804,370 A | 2/1989 | Haber et al. |
| 4,808,169 A | 2/1989 | Haber et al. |
| 4,813,937 A | 3/1989 | Vaillancourt |
| 4,813,940 A | 3/1989 | Parry et al. |
| 4,820,275 A | 4/1989 | Haber et al. |
| 4,820,286 A | 4/1989 | van der Wal et al. |
| 4,826,484 A | 5/1989 | Haber et al. |
| 4,826,489 A | 5/1989 | Haber et al. |
| 4,826,490 A | 5/1989 | Byrne et al. |
| 4,828,548 A | 5/1989 | Walter |
| 4,832,682 A | 5/1989 | Sarnoff |
| 4,832,693 A | 5/1989 | Gloyer |
| 4,834,704 A | 5/1989 | Reinicke |
| 4,834,718 A | 5/1989 | McDonald |
| 4,842,598 A | 6/1989 | Tran |
| 4,846,811 A | 7/1989 | Vanderhoof |
| 4,850,961 A | 7/1989 | Wanderer et al. |
| 4,850,968 A | 7/1989 | Romano et al. |
| 4,850,971 A | 7/1989 | Colvin |
| 4,850,976 A | 7/1989 | Heinrich et al. |
| 4,850,977 A | 7/1989 | Bayless |
| 4,850,994 A | 7/1989 | Zerbst et al. |
| 4,861,338 A | 8/1989 | Mathiesen et al. |
| 4,863,427 A | 9/1989 | Cocchi et al. |
| 4,863,435 A | 9/1989 | Sturman et al. |
| 4,863,436 A | 9/1989 | Glick |
| 4,865,592 A | 9/1989 | Rycroft |
| 4,874,372 A | 10/1989 | McArthur et al. |
| 4,874,382 A | 10/1989 | Lindemann et al. |
| 4,883,466 A | 11/1989 | Glazier |
| 4,883,472 A | 11/1989 | Michel et al. |
| 4,883,483 A * | 11/1989 | Lindmayer .................... 604/411 |
| 4,886,499 A | 12/1989 | Cirelli et al. |
| 4,887,998 A | 12/1989 | Martin et al. |
| 4,892,107 A | 1/1990 | Haber |
| 4,892,523 A | 1/1990 | Haber |
| 4,894,054 A | 1/1990 | Miskinyar |
| 4,894,055 A | 1/1990 | Sudnak |
| 4,898,589 A | 2/1990 | Dolgin et al. |
| 4,900,303 A | 2/1990 | Lemelson |
| 4,900,307 A | 2/1990 | Kulli |
| 4,900,311 A | 2/1990 | Stern et al. |
| 4,902,279 A | 2/1990 | Schmidtz et al. |
| 4,904,242 A | 2/1990 | Kulli |
| 4,906,236 A | 3/1990 | Alberts et al. |
| 4,908,022 A | 3/1990 | Haber |
| 4,909,794 A | 3/1990 | Haber et al. |
| 4,909,795 A | 3/1990 | Gelabert |
| 4,911,706 A | 3/1990 | Levitt |
| 4,913,702 A | 4/1990 | Yum et al. |
| 4,915,702 A | 4/1990 | Haber |
| 4,917,672 A | 4/1990 | Terndrup et al. |
| 4,919,146 A | 4/1990 | Rhinehart et al. |
| 4,919,657 A | 4/1990 | Haber et al. |
| 4,923,443 A | 5/1990 | Greenwood et al. |
| 4,923,445 A | 5/1990 | Ryan |
| 4,927,414 A | 5/1990 | Kulli |
| 4,929,237 A | 5/1990 | Medway |
| 4,929,241 A | 5/1990 | Kulli |
| 4,931,040 A | 6/1990 | Haber et al. |
| 4,932,944 A | 6/1990 | Jagger et al. |
| 4,932,946 A | 6/1990 | Shields |
| 4,932,947 A | 6/1990 | Cardwell |
| 4,935,013 A | 6/1990 | Haber et al. |
| 4,935,014 A | 6/1990 | Haber |
| 4,936,830 A | 6/1990 | Verlier et al. |
| 4,941,879 A | 7/1990 | Butler et al. |
| 4,944,723 A | 7/1990 | Haber et al. |
| 4,944,725 A | 7/1990 | McDonald |
| 4,946,441 A | 8/1990 | Laderoute |
| 4,950,240 A | 8/1990 | Greenwood et al. |
| 4,950,241 A | 8/1990 | Ranford |
| 4,950,250 A | 8/1990 | Haber et al. |
| 4,950,252 A | 8/1990 | Luther et al. |
| 4,955,866 A | 9/1990 | Corey |
| 4,955,868 A | 9/1990 | Klein |
| 4,955,869 A | 9/1990 | Bin et al. |
| 4,955,870 A | 9/1990 | Ridderheim et al. |
| 4,961,728 A | 10/1990 | Kosinski |
| 4,966,589 A | 10/1990 | Kaufman |
| 4,966,592 A | 10/1990 | Burns et al. |
| 4,966,593 A | 10/1990 | Lennox |
| 4,973,310 A | 11/1990 | Kosinski |
| 4,973,317 A | 11/1990 | Bobrove |
| 4,976,704 A | 12/1990 | McLees |
| 4,988,335 A | 1/1991 | Prindle et al. |
| 4,988,339 A | 1/1991 | Vadher |
| 4,994,045 A | 2/1991 | Ranford |
| 4,998,918 A | 3/1991 | Mimura et al. |
| 4,998,921 A | 3/1991 | Vickroy et al. |
| 4,998,922 A | 3/1991 | Kuracina et al. |
| 5,000,736 A | 3/1991 | Kaufhold, Jr. et al. |

| | | | | | |
|---|---|---|---|---|---|
| 5,000,737 A | 3/1991 | Free et al. | 5,135,510 A | 8/1992 | Maszkiewicz et al. |
| 5,002,548 A | 3/1991 | Campbell et al. | 5,137,515 A | 8/1992 | Hogan |
| 5,007,903 A | 4/1991 | Ellard | 5,137,516 A | 8/1992 | Rand et al. |
| 5,011,475 A | 4/1991 | Olson | 5,141,496 A | 8/1992 | Dalto et al. |
| RE33,585 E | 5/1991 | Haber et al. | 5,143,414 A | 9/1992 | Rosellini |
| 5,015,240 A | 5/1991 | Soproni et al. | 5,147,311 A | 9/1992 | Pickhard et al. |
| 5,017,187 A | 5/1991 | Sullivan | 5,147,326 A | 9/1992 | Talonn et al. |
| 5,019,043 A | 5/1991 | Segui Pastor et al. | 5,147,327 A | 9/1992 | Johnson |
| 5,019,044 A | 5/1991 | Tsao et al. | 5,149,323 A | 9/1992 | Colonna |
| 5,019,047 A | 5/1991 | Kriesel | 5,152,751 A | 10/1992 | Kozlowski |
| 5,019,048 A | 5/1991 | Margolin | 5,156,599 A | 10/1992 | Ranford et al. |
| 5,021,059 A | 6/1991 | Kensey et al. | 5,160,326 A | 11/1992 | Talonn et al. |
| 5,024,665 A | 6/1991 | Kaufman | 5,163,916 A | 11/1992 | Sunderland |
| 5,026,349 A | 6/1991 | Schmitz et al. | 5,163,917 A | 11/1992 | Huefner et al. |
| 5,030,208 A | 7/1991 | Novacek et al. | 5,163,918 A | 11/1992 | Righi et al. |
| 5,034,003 A | 7/1991 | Denance et al. | 5,167,632 A | 12/1992 | Eid et al. |
| 5,037,306 A | 8/1991 | van Schoonhoven et al. | 5,167,641 A | 12/1992 | Schmitz |
| 5,037,382 A | 8/1991 | Kvorning et al. | 5,169,389 A | 12/1992 | Kriesel |
| 5,037,393 A | 8/1991 | Ellgass et al. | 5,169,392 A | 12/1992 | Ranford et al. |
| 5,037,400 A | 8/1991 | Curry | 5,176,641 A | 1/1993 | Idriss |
| 5,041,094 A | 8/1991 | Perego et al. | 5,176,656 A | 1/1993 | Bayless |
| 5,042,977 A | 8/1991 | Bechtold et al. | 5,176,657 A | 1/1993 | Shields |
| 5,045,066 A | 9/1991 | Scheuble et al. | 5,183,468 A | 2/1993 | McLees |
| 5,047,016 A | 9/1991 | Dolgin et al. | 5,183,469 A | 2/1993 | Capaccio |
| 5,049,133 A | 9/1991 | Villen Pascual et al. | 5,188,614 A | 2/1993 | Hart |
| 5,049,136 A | 9/1991 | Johnson | 5,190,526 A | 3/1993 | Murray et al. |
| 5,053,010 A | 10/1991 | McGary et al. | 5,193,552 A | 3/1993 | Columbus et al. |
| 5,053,018 A | 10/1991 | Talonn et al. | 5,195,982 A | 3/1993 | Hoenig |
| 5,055,102 A | 10/1991 | Sitnik | 5,195,983 A | 3/1993 | Boese |
| 5,057,086 A | 10/1991 | Dillard, III et al. | 5,195,985 A | 3/1993 | Hall |
| 5,057,089 A | 10/1991 | Greco | 5,199,952 A | 4/1993 | Marshall, Sr. et al. |
| 5,059,180 A | 10/1991 | McLees | 5,201,708 A | 4/1993 | Martin |
| 5,059,185 A | 10/1991 | Ryan | 5,201,710 A | 4/1993 | Caselli et al. |
| 5,061,249 A | 10/1991 | Campbell | 5,205,826 A | 4/1993 | Chen et al. |
| 5,061,251 A | 10/1991 | Juhasz | 5,205,827 A | 4/1993 | Novacek et al. |
| 5,064,419 A | 11/1991 | Gaarde et al. | 5,207,646 A | 5/1993 | Brunel et al. |
| 5,067,490 A | 11/1991 | Haber | 5,207,699 A | 5/1993 | Coe |
| 5,067,948 A | 11/1991 | Haber et al. | 5,209,739 A | 5/1993 | Talalay |
| 5,071,353 A | 12/1991 | van der Wal et al. | 5,211,628 A | 5/1993 | Marshall |
| 5,080,104 A | 1/1992 | Marks et al. | 5,211,629 A | 5/1993 | Pressly et al. |
| 5,084,027 A | 1/1992 | Bernard | 5,215,524 A | 6/1993 | Vallelunga et al. |
| 5,084,029 A | 1/1992 | Nacci nee Tagliaferri et al. | 5,215,533 A | 6/1993 | Robb et al. |
| 5,084,030 A | 1/1992 | Byrne et al. | 5,215,534 A | 6/1993 | De Harde et al. |
| 5,085,640 A | 2/1992 | Gibbs | 5,215,535 A | 6/1993 | Gettig et al. |
| 5,085,641 A | 2/1992 | Sarnoff et al. | 5,215,536 A | 6/1993 | Lampropoulos et al. |
| 5,085,642 A | 2/1992 | Sarnoff et al. | 5,217,437 A | 6/1993 | Talonn et al. |
| 5,088,986 A | 2/1992 | Nusbaum | 5,219,338 A | 6/1993 | Haworth |
| 5,088,988 A | 2/1992 | Talonn et al. | 5,221,262 A | 6/1993 | Kite et al. |
| 5,092,842 A | 3/1992 | Bechtold et al. | 5,222,943 A | 6/1993 | Mazzara et al. |
| 5,092,843 A | 3/1992 | Monroe et al. | 5,222,947 A | 6/1993 | D'Amico |
| 5,092,851 A | 3/1992 | Ragner | 5,222,974 A | 6/1993 | Kensey et al. |
| 5,092,852 A | 3/1992 | Poling et al. | 5,224,936 A | 7/1993 | Gallagher |
| 5,092,853 A | 3/1992 | Couvertier, II | 5,226,882 A | 7/1993 | Bates et al. |
| 5,098,382 A | 3/1992 | Haber et al. | 5,228,883 A | 7/1993 | Blakely et al. |
| 5,098,400 A | 3/1992 | Crouse et al. | RE34,335 E | 8/1993 | Butler et al. |
| 5,098,401 A | 3/1992 | De Lange | 5,232,457 A | 8/1993 | Grim |
| 5,102,393 A | 4/1992 | Sarnoff et al. | 5,232,458 A | 8/1993 | Chen et al. |
| 5,102,397 A | 4/1992 | Brunet et al. | 5,238,654 A | 8/1993 | Nohl et al. |
| 5,104,378 A | 4/1992 | Haber et al. | 5,242,388 A | 9/1993 | Marshall, Sr. |
| 5,104,380 A | 4/1992 | Holman et al. | 5,242,401 A | 9/1993 | Colsky |
| 5,104,384 A | 4/1992 | Parry et al. | 5,242,416 A | 9/1993 | Hutson |
| 5,104,385 A | 4/1992 | Huband | 5,242,420 A | 9/1993 | Martin |
| 5,106,370 A | 4/1992 | Stewart | 5,246,428 A | 9/1993 | Falknor |
| 5,106,372 A | 4/1992 | Ranford | 5,250,031 A | 10/1993 | Kaplan et al. |
| 5,106,379 A | 4/1992 | Leap | 5,256,152 A | 10/1993 | Marks |
| 5,108,378 A | 4/1992 | Firth et al. | 5,257,976 A | 11/1993 | Fenet et al. |
| 5,108,379 A | 4/1992 | Dolgin et al. | 5,261,894 A | 11/1993 | Smith et al. |
| 5,112,307 A | 5/1992 | Haber et al. | 5,263,933 A | 11/1993 | Novacek et al. |
| 5,112,316 A | 5/1992 | Venturini et al. | 5,267,961 A | 12/1993 | Shaw |
| 5,114,404 A | 5/1992 | Paxton et al. | 5,267,963 A | 12/1993 | Bachynsky |
| 5,120,310 A | 6/1992 | Shaw | 5,269,761 A | 12/1993 | Stehrenberger et al. |
| 5,120,314 A | 6/1992 | Greenwood | 5,269,762 A | 12/1993 | Armbruster et al. |
| 5,120,321 A | 6/1992 | Oksman et al. | 5,269,766 A | 12/1993 | Haber et al. |
| 5,122,118 A | 6/1992 | Haber et al. | 5,273,532 A | 12/1993 | Niezink et al. |
| 5,122,124 A | 6/1992 | Novacek et al. | 5,273,538 A | 12/1993 | Chen et al. |
| 5,125,898 A | 6/1992 | Kaufhold, Jr. et al. | 5,273,539 A | 12/1993 | Chen et al. |
| 5,125,899 A | 6/1992 | Frignoli et al. | 5,273,541 A | 12/1993 | Malenchek |
| 5,127,910 A | 7/1992 | Talonn et al. | 5,273,544 A | 12/1993 | van der Wal et al. |
| 5,135,507 A | 8/1992 | Haber et al. | 5,279,554 A | 1/1994 | Turley et al. |

| | | | | | |
|---|---|---|---|---|---|
| 5,279,566 A | 1/1994 | Kline, Jr. et al. | 5,378,240 A | 1/1995 | Curie et al. |
| 5,279,576 A | 1/1994 | Loo et al. | 5,383,857 A | 1/1995 | Levitov |
| 5,279,577 A | 1/1994 | Collett | 5,385,550 A | 1/1995 | Su et al. |
| 5,279,581 A | 1/1994 | Firth et al. | 5,385,551 A | 1/1995 | Shaw |
| 5,279,582 A | 1/1994 | Davison et al. | 5,385,557 A | 1/1995 | Thompson |
| 5,279,583 A | 1/1994 | Shober, Jr. et al. | 5,389,076 A | 2/1995 | Shaw |
| 5,279,590 A | 1/1994 | Sinko et al. | 5,389,085 A | 2/1995 | D'Alessio et al. |
| 5,282,793 A | 2/1994 | Larson | 5,391,151 A | 2/1995 | Wilmot et al. |
| 5,282,822 A | 2/1994 | Macors et al. | 5,391,183 A | 2/1995 | Janzen et al. |
| 5,282,827 A | 2/1994 | Kensey et al. | 5,395,317 A | 3/1995 | Kambin |
| 5,284,479 A | 2/1994 | de Jong et al. | 5,395,337 A | 3/1995 | Clemens et al. |
| 5,290,233 A | 3/1994 | Campbell | 5,399,163 A | 3/1995 | Peterson et al. |
| 5,290,239 A | 3/1994 | Classey et al. | 5,401,246 A | 3/1995 | Mazur et al. |
| 5,290,240 A | 3/1994 | Horres, Jr. | 5,401,249 A | 3/1995 | Shields |
| 5,290,254 A | 3/1994 | Vaillancourt | 5,401,251 A | 3/1995 | Hui |
| 5,292,314 A | 3/1994 | D'Alessio et al. | 5,403,286 A | 4/1995 | Lockwood, Jr. |
| 5,295,963 A | 3/1994 | Deeks et al. | 5,403,287 A | 4/1995 | Talonn et al. |
| 5,295,965 A | 3/1994 | Wilmot et al. | 5,405,326 A | 4/1995 | Haber et al. |
| 5,295,972 A | 3/1994 | Mischenko | 5,405,327 A | 4/1995 | Chen et al. |
| 5,295,973 A | 3/1994 | Chen et al. | 5,407,436 A | 4/1995 | Toft et al. |
| 5,295,974 A | 3/1994 | O'Laughlin | 5,409,466 A | 4/1995 | Watson et al. |
| 5,295,975 A | 3/1994 | Lockwood, Jr. | RE34,936 E | 5/1995 | Campbell et al. |
| 5,300,029 A | 4/1994 | Denance et al. | 5,411,487 A | 5/1995 | Castagna |
| 5,300,030 A | 4/1994 | Crossman et al. | 5,415,638 A | 5/1995 | Novacek et al. |
| 5,300,040 A | 4/1994 | Martin | 5,415,645 A | 5/1995 | Friend et al. |
| 5,300,045 A | 4/1994 | Plassche, Jr. | 5,415,648 A | 5/1995 | Malay et al. |
| 5,304,137 A | 4/1994 | Fluke | 5,419,766 A | 5/1995 | Chang et al. |
| 5,304,138 A | 4/1994 | Mercado | 5,419,773 A | 5/1995 | Rupp |
| 5,306,251 A | 4/1994 | Alexander et al. | 5,423,746 A | 6/1995 | Burkett et al. |
| 5,306,258 A | 4/1994 | de la Fuente | 5,425,715 A | 6/1995 | Dalling et al. |
| 5,308,332 A | 5/1994 | Dillard, III et al. | 5,425,722 A | 6/1995 | Whisson et al. |
| 5,311,841 A | 5/1994 | Thaxton | 5,429,611 A | 7/1995 | Rait |
| 5,312,353 A | 5/1994 | Boggess et al. | 5,429,612 A | 7/1995 | Berthier et al. |
| 5,312,366 A | 5/1994 | Vailancourt | 5,429,613 A | 7/1995 | D'Amico |
| 5,312,368 A | 5/1994 | Haynes | 5,431,631 A | 7/1995 | Lu et al. |
| 5,312,370 A | 5/1994 | Talonn et al. | 5,431,632 A | 7/1995 | Lu et al. |
| 5,312,371 A | 5/1994 | Dombrowski et al. | 5,433,712 A | 7/1995 | Stiles et al. |
| 5,312,372 A | 5/1994 | DeHarde et al. | 5,445,618 A | 8/1995 | Adobbati |
| 5,314,503 A | 5/1994 | Bobrove et al. | 5,445,620 A | 8/1995 | Haber et al. |
| 5,318,538 A | 6/1994 | Martin | 5,451,210 A | 9/1995 | Kramer et al. |
| 5,320,609 A | 6/1994 | Haber et al. | 5,458,576 A | 10/1995 | Haber et al. |
| 5,322,517 A | 6/1994 | Sircom et al. | 5,458,580 A | 10/1995 | Hajishoreh |
| 5,324,265 A | 6/1994 | Murray et al. | 5,460,611 A | 10/1995 | Alexander |
| 5,328,475 A | 7/1994 | Chen et al. | 5,462,531 A | 10/1995 | Novacek et al. |
| 5,328,482 A | 7/1994 | Sircom et al. | 5,466,223 A | 11/1995 | Bressler et al. |
| 5,328,484 A | 7/1994 | Somers et al. | 5,468,227 A | 11/1995 | Haskell |
| 5,330,430 A | 7/1994 | Sullivan | 5,474,687 A | 12/1995 | Van Vlasselaer |
| 5,334,149 A | 8/1994 | Nortman et al. | 5,478,314 A | 12/1995 | Malenchek |
| 5,334,158 A | 8/1994 | McLees | 5,478,316 A | 12/1995 | Bitdinger et al. |
| 5,334,173 A | 8/1994 | Armstrong, Jr. | 5,478,328 A | 12/1995 | Silverman et al. |
| 5,336,180 A | 8/1994 | Kriesel et al. | 5,480,385 A | 1/1996 | Thorne et al. |
| 5,336,187 A | 8/1994 | Terry et al. | 5,480,387 A | 1/1996 | Gabriel et al. |
| 5,336,199 A | 8/1994 | Castillo et al. | 5,482,039 A | 1/1996 | Place |
| 5,338,303 A | 8/1994 | King et al. | 5,486,163 A | 1/1996 | Haynes |
| 5,338,311 A | 8/1994 | Mahurkar | 5,486,164 A | 1/1996 | Streck |
| 5,342,310 A | 8/1994 | Ueyama et al. | 5,487,732 A | 1/1996 | Jeffrey et al. |
| 5,342,320 A | 8/1994 | Cameron | 5,487,733 A | 1/1996 | Caizza et al. |
| 5,344,407 A | 9/1994 | Ryan | 5,487,734 A | 1/1996 | Thorne et al. |
| 5,344,408 A | 9/1994 | Partika | 5,489,272 A | 2/1996 | Wirtz et al. |
| 5,346,475 A | 9/1994 | Gregorio | 5,492,536 A | 2/1996 | Mascia |
| 5,346,480 A | 9/1994 | Hess et al. | 5,496,278 A | 3/1996 | Buff |
| 5,346,481 A | 9/1994 | Bunin | 5,501,672 A | 3/1996 | Firth et al. |
| 5,348,544 A | 9/1994 | Sweeney et al. | 5,512,048 A | 4/1996 | Slettenmark et al. |
| 5,352,202 A | 10/1994 | Hammett et al. | 5,512,050 A | 4/1996 | Caizza et al. |
| 5,352,203 A | 10/1994 | Vallelunga et al. | RE35,252 E | 5/1996 | Clack et al. |
| 5,352,500 A | 10/1994 | Memon | 5,514,097 A | 5/1996 | Knauer |
| 5,354,287 A | 10/1994 | Wacks | 5,514,107 A | 5/1996 | Haber et al. |
| 5,356,387 A | 10/1994 | Sirbola | 5,520,639 A | 5/1996 | Peterson et al. |
| 5,358,489 A | 10/1994 | Wyrick | 5,520,649 A | 5/1996 | Novacek et al. |
| 5,360,410 A | 11/1994 | Wacks | 5,522,797 A | 6/1996 | Grimm |
| 5,364,362 A | 11/1994 | Schulz et al. | 5,522,812 A | 6/1996 | Talonn et al. |
| 5,364,370 A | 11/1994 | Szerlip et al. | 5,527,283 A | 6/1996 | Swisher, III |
| 5,366,447 A | 11/1994 | Gurley | 5,527,284 A | 6/1996 | Ohnemus et al. |
| 5,368,568 A | 11/1994 | Pitts et al. | 5,527,287 A | 6/1996 | Miskinyar |
| 5,368,570 A | 11/1994 | Thompson et al. | 5,527,307 A | 6/1996 | Srisathapat et al. |
| 5,368,571 A | 11/1994 | Horres, Jr. | 5,529,189 A | 6/1996 | Feldschuh |
| 5,370,619 A | 12/1994 | Rossi et al. | 5,531,691 A | 7/1996 | Shonfeld et al. |
| 5,370,626 A | 12/1994 | Farris | 5,531,692 A | 7/1996 | Rogers |
| 5,374,250 A | 12/1994 | Dixon | 5,531,694 A | 7/1996 | Clemens et al. |

| Patent | Date | Inventor |
|---|---|---|
| 5,531,704 A | 7/1996 | Knotek |
| 5,531,706 A | 7/1996 | de la Fuente |
| 5,533,975 A | 7/1996 | Lu et al. |
| 5,533,984 A | 7/1996 | Parmigiani et al. |
| 5,536,243 A | 7/1996 | Jeyendran |
| 5,536,253 A | 7/1996 | Haber et al. |
| 5,536,257 A | 7/1996 | Byrne et al. |
| 5,538,506 A | 7/1996 | Farris et al. |
| 5,538,508 A | 7/1996 | Steyn et al. |
| 5,540,664 A | 7/1996 | Wyrick |
| 5,540,666 A | 7/1996 | Barta et al. |
| 5,542,920 A | 8/1996 | Cherif Cheikh et al. |
| 5,542,927 A | 8/1996 | Thorne et al. |
| 5,549,558 A | 8/1996 | Martin |
| 5,549,568 A | 8/1996 | Shields |
| 5,549,570 A | 8/1996 | Rogalsky |
| 5,549,572 A | 8/1996 | Byrne et al. |
| 5,549,708 A | 8/1996 | Thorne et al. |
| 5,558,648 A | 9/1996 | Shields |
| 5,562,624 A | 10/1996 | Righi et al. |
| 5,562,626 A | 10/1996 | Sanpietro |
| 5,562,631 A | 10/1996 | Bogert |
| 5,568,623 A | 10/1996 | Ogawa et al. |
| 5,569,202 A | 10/1996 | Kovalic et al. |
| 5,569,203 A | 10/1996 | Chen et al. |
| 5,573,513 A | 11/1996 | Wozencroft et al. |
| 5,575,770 A | 11/1996 | Melsky et al. |
| 5,578,011 A | 11/1996 | Shaw |
| 5,578,014 A | 11/1996 | Erez et al. |
| 5,578,015 A | 11/1996 | Robb et al. |
| 5,582,591 A | 12/1996 | Cheikh et al. |
| 5,584,815 A | 12/1996 | Pawelka et al. |
| 5,586,976 A | 12/1996 | Coutoumanos |
| 5,591,133 A | 1/1997 | Feuerborn et al. |
| 5,591,134 A | 1/1997 | Shu et al. |
| 5,591,138 A | 1/1997 | Vaillancourt |
| 5,593,387 A | 1/1997 | Rupp |
| 5,593,390 A | 1/1997 | Castellano et al. |
| 5,599,309 A | 2/1997 | Marshall et al. |
| 5,599,316 A | 2/1997 | Blakely |
| 5,599,318 A | 2/1997 | Sweeney et al. |
| 5,601,532 A | 2/1997 | Gaba |
| 5,601,535 A | 2/1997 | Byrne et al. |
| 5,605,544 A | 2/1997 | Tsao et al. |
| 5,609,577 A | 3/1997 | Haber et al. |
| 5,611,781 A | 3/1997 | Sircom et al. |
| 5,611,782 A | 3/1997 | Haedt |
| 5,613,500 A | 3/1997 | Bishop |
| 5,613,951 A | 3/1997 | Meyer et al. |
| 5,613,952 A | 3/1997 | Pressly, Sr. et al. |
| 5,615,771 A | 4/1997 | Hollister |
| 5,616,123 A | 4/1997 | Cheikh et al. |
| 5,616,132 A | 4/1997 | Newman et al. |
| 5,616,134 A | 4/1997 | Firth et al. |
| 5,616,135 A | 4/1997 | Thorne et al. |
| 5,620,422 A | 4/1997 | Halbich |
| 5,620,425 A | 4/1997 | Heffernan et al. |
| 5,624,401 A | 4/1997 | Leijd et al. |
| 5,624,405 A | 4/1997 | Futagawa et al. |
| 5,628,765 A | 5/1997 | Morita et al. |
| 5,630,803 A | 5/1997 | Tamaro |
| 5,632,730 A | 5/1997 | Reinert |
| 5,632,733 A | 5/1997 | Shaw |
| 5,634,906 A | 6/1997 | Haber et al. |
| 5,634,909 A | 6/1997 | Schmitz |
| 5,634,937 A | 6/1997 | Mollenauer et al. |
| 5,637,092 A | 6/1997 | Shaw |
| 5,637,094 A | 6/1997 | Stewart, Jr. et al. |
| 5,643,220 A | 7/1997 | Cosme |
| 5,643,222 A | 7/1997 | Mahurkar |
| 5,647,851 A | 7/1997 | Pokras |
| 5,649,622 A | 7/1997 | Hollister |
| 5,651,774 A | 7/1997 | Taranto et al. |
| 5,653,687 A | 8/1997 | Mills et al. |
| 5,653,688 A | 8/1997 | Mills et al. |
| 5,653,693 A | 8/1997 | Miwa et al. |
| 5,656,031 A | 8/1997 | Thorne et al. |
| 5,658,256 A | 8/1997 | Shields |
| 5,658,257 A | 8/1997 | Ryles et al. |
| 5,658,258 A | 8/1997 | Kneer et al. |
| 5,658,259 A | 8/1997 | Pearson et al. |
| 5,662,610 A | 9/1997 | Sircom et al. |
| 5,662,617 A | 9/1997 | Odell et al. |
| 5,665,071 A | 9/1997 | Wyrick |
| 5,665,075 A | 9/1997 | Gyure et al. |
| 5,669,889 A | 9/1997 | Gyure et al. |
| 5,672,155 A | 9/1997 | Riley et al. |
| 5,672,161 A | 9/1997 | Allen et al. |
| 5,681,291 A | 10/1997 | Galli et al. |
| 5,681,295 A | 10/1997 | Gyure et al. |
| 5,688,240 A | 11/1997 | Novacek et al. |
| 5,688,251 A | 11/1997 | Chanoch |
| 5,693,016 A | 12/1997 | Gumaste et al. |
| 5,693,022 A | 12/1997 | Haynes |
| 5,693,023 A | 12/1997 | Adams |
| 5,695,472 A | 12/1997 | Wyrick |
| 5,704,911 A | 1/1998 | Parsons |
| 5,704,921 A | 1/1998 | Carilli |
| 5,707,393 A | 1/1998 | Kensey et al. |
| 5,709,662 A | 1/1998 | Olive et al. |
| 5,709,667 A | 1/1998 | Carilli |
| 5,709,668 A | 1/1998 | Wacks |
| 5,713,866 A | 2/1998 | Wilmot |
| 5,713,871 A | 2/1998 | Stock |
| 5,713,872 A | 2/1998 | Feuerborn et al. |
| 5,716,655 A | 2/1998 | Hamstra et al. |
| 5,720,727 A | 2/1998 | Alexander et al. |
| 5,725,498 A | 3/1998 | Janzen et al. |
| 5,738,655 A | 4/1998 | Vallelunga et al. |
| 5,741,223 A | 4/1998 | Janzen et al. |
| 5,743,879 A | 4/1998 | Kriesel |
| 5,743,887 A | 4/1998 | Brattesani |
| 5,743,888 A | 4/1998 | Wilkes et al. |
| 5,743,891 A | 4/1998 | Tolkoff et al. |
| 5,746,718 A | 5/1998 | Steyn et al. |
| 5,749,854 A | 5/1998 | Shen et al. |
| 5,749,860 A | 5/1998 | Kyte |
| 5,755,692 A | 5/1998 | Manicom et al. |
| 5,769,822 A | 6/1998 | McGary et al. |
| 5,769,827 A | 6/1998 | DeMichele et al. |
| 5,779,675 A | 7/1998 | Reilly et al. |
| 5,779,677 A | 7/1998 | Frezza et al. |
| 5,779,684 A | 7/1998 | Tamaro |
| 5,788,677 A | 8/1998 | Botich et al. |
| 5,788,713 A | 8/1998 | Dubach et al. |
| 5,792,107 A | 8/1998 | Petrocelli et al. |
| 5,792,121 A | 8/1998 | Tamaro |
| 5,792,122 A | 8/1998 | Brimhall et al. |
| 5,795,336 A | 8/1998 | Romano et al. |
| 5,797,885 A | 8/1998 | Rubin |
| 5,800,403 A | 9/1998 | Pressly, Sr. et al. |
| 5,807,334 A | 9/1998 | Hodosh et al. |
| 5,807,345 A | 9/1998 | Grabenkort |
| 5,807,352 A | 9/1998 | Tamaro |
| 5,810,775 A | 9/1998 | Shaw |
| 5,810,784 A | 9/1998 | Tamaro |
| 5,817,054 A | 10/1998 | Grimm |
| 5,817,070 A | 10/1998 | Tamaro |
| 5,820,602 A | 10/1998 | Kovelman et al. |
| 5,823,997 A | 10/1998 | Thorne |
| 5,823,998 A | 10/1998 | Yamagata et al. |
| 5,827,293 A | 10/1998 | Elliott |
| 5,830,130 A | 11/1998 | Janzen et al. |
| 5,836,911 A | 11/1998 | Marzynski et al. |
| 5,836,920 A | 11/1998 | Robertson et al. |
| 5,843,036 A | 12/1998 | Olive et al. |
| 5,843,047 A | 12/1998 | Pyrozyk et al. |
| 5,848,990 A | 12/1998 | Cirelli et al. |
| 5,851,197 A | 12/1998 | Marano et al. |
| 5,853,390 A | 12/1998 | Freschi et al. |
| 5,853,393 A | 12/1998 | Bogert |
| 5,855,839 A | 1/1999 | Brunel et al. |
| 5,858,000 A | 1/1999 | Novacek et al. |
| 5,865,227 A | 2/1999 | Carilli |
| 5,865,804 A | 2/1999 | Bachynsky |
| 5,868,711 A | 2/1999 | Kramer et al. |
| 5,879,337 A | 3/1999 | Kuracina et al. |
| 5,882,342 A | 3/1999 | Cooper et al. |

| Patent | Date | Inventor |
|---|---|---|
| 5,885,257 A | 3/1999 | Badger et al. |
| 5,891,052 A | 4/1999 | Simmons |
| 5,891,092 A | 4/1999 | Castellano |
| 5,891,097 A | 4/1999 | Saito et al. |
| 5,891,105 A | 4/1999 | Mahurkar |
| 5,897,508 A | 4/1999 | Konrad et al. |
| 5,899,885 A | 5/1999 | Reilly et al. |
| 5,899,886 A | 5/1999 | Cosme |
| 5,908,404 A | 6/1999 | Elliott |
| 5,908,408 A | 6/1999 | McGary et al. |
| 5,910,131 A | 6/1999 | McGary et al. |
| 5,911,706 A | 6/1999 | Estabrook et al. |
| 5,919,166 A | 7/1999 | McGary et al. |
| 5,921,959 A | 7/1999 | McGary et al. |
| 5,921,960 A | 7/1999 | McGary et al. |
| 5,921,963 A | 7/1999 | Erez et al. |
| 5,921,964 A | 7/1999 | Martin |
| 5,925,019 A | 7/1999 | Ljungquist et al. |
| 5,927,961 A | 7/1999 | Robinson et al. |
| 5,928,188 A | 7/1999 | McGary et al. |
| 5,928,194 A | 7/1999 | Maget |
| 5,928,205 A | 7/1999 | Marshall et al. |
| 5,931,813 A | 8/1999 | Liu et al. |
| 5,938,638 A | 8/1999 | Passariello et al. |
| 5,938,639 A | 8/1999 | Reilly et al. |
| 5,941,850 A | 8/1999 | Shah et al. |
| 5,944,692 A | 8/1999 | McGary et al. |
| 5,944,693 A | 8/1999 | Jacobs |
| 5,951,522 A | 9/1999 | Rosato et al. |
| 5,957,892 A | 9/1999 | Thorne |
| 5,957,895 A | 9/1999 | Sage et al. |
| 5,957,897 A | 9/1999 | Jeffrey et al. |
| 5,960,797 A | 10/1999 | Kramer et al. |
| 5,961,491 A | 10/1999 | McGary et al. |
| 5,971,953 A | 10/1999 | Bachynsky |
| RE36,398 E | 11/1999 | Byrne et al. |
| 5,979,579 A | 11/1999 | Jurewicz |
| 5,980,494 A | 11/1999 | Malenchek et al. |
| 5,984,899 A | 11/1999 | D'Alessio et al. |
| 5,984,900 A | 11/1999 | Mikkelsen et al. |
| 5,989,219 A | 11/1999 | Villas et al. |
| 5,989,221 A | 11/1999 | Hjertman et al. |
| 5,993,417 A | 11/1999 | Yerfino et al. |
| 5,993,418 A | 11/1999 | Alexander |
| RE36,447 E | 12/1999 | Byrne et al. |
| 5,997,500 A | 12/1999 | Cook et al. |
| 5,997,511 A | 12/1999 | Curie et al. |
| 5,997,513 A | 12/1999 | Smith et al. |
| 6,001,080 A | 12/1999 | Kuracina et al. |
| 6,007,474 A | 12/1999 | Rydell |
| 6,010,486 A | 1/2000 | Carter et al. |
| 6,010,487 A | 1/2000 | DeMichele et al. |
| 6,015,396 A | 1/2000 | Buttgen et al. |
| 6,015,438 A | 1/2000 | Shaw |
| 6,017,325 A | 1/2000 | Yerfino et al. |
| 6,022,337 A | 2/2000 | Herbst et al. |
| 6,033,386 A | 3/2000 | Novacek et al. |
| 6,033,387 A | 3/2000 | Brunel et al. |
| 6,036,674 A | 3/2000 | Caizza et al. |
| 6,039,713 A | 3/2000 | Botich et al. |
| 6,050,974 A | 4/2000 | Allard et al. |
| 6,050,977 A | 4/2000 | Adams |
| 6,056,716 A | 5/2000 | D'Antonio et al. |
| 6,056,724 A | 5/2000 | Lacroix et al. |
| 6,056,734 A | 5/2000 | Jacobsen et al. |
| 6,063,040 A | 5/2000 | Owen et al. |
| 6,063,053 A | 5/2000 | Castellano et al. |
| 6,066,115 A | 5/2000 | Chang Lai et al. |
| 6,068,616 A | 5/2000 | Janus et al. |
| 6,070,623 A | 6/2000 | Aneas et al. |
| 6,074,360 A | 6/2000 | Haar et al. |
| 6,074,369 A | 6/2000 | Sage et al. |
| 6,074,370 A | 6/2000 | Pressly, Sr. et al. |
| 6,077,245 A | 6/2000 | Heinrich et al. |
| 6,080,135 A | 6/2000 | Van Stokkum et al. |
| 6,083,199 A | 7/2000 | Thorley et al. |
| 6,083,200 A | 7/2000 | Grimm et al. |
| 6,086,562 A | 7/2000 | Jacobsen et al. |
| 6,086,569 A | 7/2000 | Schweizer |
| 6,090,077 A | 7/2000 | Shaw |
| 6,090,078 A | 7/2000 | Erskine |
| 6,090,080 A | 7/2000 | Jost et al. |
| 6,093,172 A | 7/2000 | Funderburk et al. |
| 6,099,500 A | 8/2000 | Dysarz |
| 6,099,503 A | 8/2000 | Stradella et al. |
| 6,099,504 A | 8/2000 | Gross et al. |
| 6,102,844 A | 8/2000 | Ravins et al. |
| 6,113,574 A | 9/2000 | Spinello |
| 6,117,112 A | 9/2000 | Mahurkar |
| 6,117,113 A | 9/2000 | Novacek et al. |
| 6,126,637 A | 10/2000 | Kriesel et al. |
| 6,129,710 A | 10/2000 | Padgett et al. |
| 6,142,972 A | 11/2000 | Cheikh et al. |
| 6,149,626 A | 11/2000 | Bachynsky et al. |
| 6,149,629 A | 11/2000 | Wilson et al. |
| 6,156,008 A | 12/2000 | Castellano |
| 6,156,010 A | 12/2000 | Kuracina et al. |
| 6,156,013 A | 12/2000 | Mahurkar |
| 6,156,015 A | 12/2000 | DeMichele et al. |
| 6,159,161 A | 12/2000 | Hodosh |
| 6,159,181 A | 12/2000 | Crossman et al. |
| 6,159,185 A | 12/2000 | Tanihata et al. |
| 6,171,284 B1 | 1/2001 | Kao et al. |
| 6,179,812 B1 | 1/2001 | Botich et al. |
| 6,183,444 B1 | 2/2001 | Glines et al. |
| 6,183,446 B1 | 2/2001 | Jeanbourquin et al. |
| 6,186,980 B1 | 2/2001 | Brunel et al. |
| 6,192,891 B1 | 2/2001 | Gravel et al. |
| 6,193,695 B1 | 2/2001 | Rippstein, Jr. |
| RE37,110 E | 3/2001 | Hollister |
| 6,206,856 B1 | 3/2001 | Mahurkar |
| 6,206,857 B1 | 3/2001 | Chen |
| 6,210,369 B1 | 4/2001 | Wilmot et al. |
| 6,217,550 B1 | 4/2001 | Capes et al. |
| 6,217,559 B1 | 4/2001 | Foster |
| 6,221,044 B1 | 4/2001 | Greco et al. |
| 6,221,051 B1 | 4/2001 | Hjertman et al. |
| 6,221,052 B1 | 4/2001 | Caizza et al. |
| 6,224,576 B1 | 5/2001 | Thorne et al. |
| 6,228,054 B1 | 5/2001 | Dysarz |
| 6,228,055 B1 | 5/2001 | Foerster et al. |
| 6,235,006 B1 | 5/2001 | Dillon et al. |
| 6,238,372 B1 | 5/2001 | Zinger et al. |
| 6,241,707 B1 | 6/2001 | Dysarz |
| 6,241,708 B1 | 6/2001 | Reilly et al. |
| 6,254,575 B1 | 7/2001 | Thorne, Jr. et al. |
| 6,254,580 B1 | 7/2001 | Svedman et al. |
| 6,258,056 B1 | 7/2001 | Turley et al. |
| 6,261,264 B1 | 7/2001 | Tamaro |
| 6,261,265 B1 | 7/2001 | Mosseri et al. |
| 6,267,748 B1 | 7/2001 | Gulliksen et al. |
| 6,270,472 B1 | 8/2001 | Antaki et al. |
| 6,270,481 B1 | 8/2001 | Mason et al. |
| 6,273,870 B1 | 8/2001 | Garvin |
| 6,280,399 B1 | 8/2001 | Rossin et al. |
| 6,280,420 B1 | 8/2001 | Ferguson et al. |
| 6,280,421 B1 | 8/2001 | Kirchhofer et al. |
| 6,283,941 B1 | 9/2001 | Schoenfeld et al. |
| 6,293,925 B1 | 9/2001 | Safabash et al. |
| 6,299,601 B1 | 10/2001 | Hjertman et al. |
| 6,309,374 B1 | 10/2001 | Hecker et al. |
| 6,309,375 B1 | 10/2001 | Glines et al. |
| 6,312,409 B1 | 11/2001 | Gross et al. |
| 6,315,113 B1 | 11/2001 | Britton et al. |
| 6,319,233 B1 | 11/2001 | Jansen et al. |
| 6,319,234 B1 | 11/2001 | Restelli et al. |
| 6,322,536 B1 | 11/2001 | Rosengart et al. |
| RE37,487 E | 12/2001 | Reilly et al. |
| 6,325,781 B1 | 12/2001 | Takagi et al. |
| 6,325,789 B1 | 12/2001 | Janzen et al. |
| 6,331,173 B1 | 12/2001 | Ljungquist et al. |
| 6,332,875 B2 | 12/2001 | Inkpen et al. |
| 6,344,031 B1 | 2/2002 | Novacek et al. |
| 6,356,783 B1 | 3/2002 | Hubbard, Jr. |
| 6,358,236 B1 | 3/2002 | DeFoggi et al. |
| 6,361,525 B2 | 3/2002 | Capes et al. |
| 6,364,865 B1 | 4/2002 | Lavi et al. |
| 6,368,303 B1 | 4/2002 | Caizza |

| Patent No. | Date | Name |
|---|---|---|
| 6,371,938 B1 | 4/2002 | Reilly et al. |
| 6,379,336 B1 | 4/2002 | Asbaghi et al. |
| 6,379,340 B1 | 4/2002 | Zinger et al. |
| 6,387,078 B1 | 5/2002 | Gillespie, III |
| 6,402,716 B1 | 6/2002 | Ryoo et al. |
| 6,409,701 B1 | 6/2002 | Cohn et al. |
| 6,409,703 B1 | 6/2002 | Lu et al. |
| 6,409,706 B1 | 6/2002 | Loy |
| 6,412,490 B1 | 7/2002 | Lee |
| 6,413,236 B1 | 7/2002 | Van Dyke |
| 6,413,237 B1 | 7/2002 | Caizza et al. |
| 6,416,323 B1 | 7/2002 | Grenfell et al. |
| 6,416,497 B1 | 7/2002 | Kirk |
| 6,419,658 B1 | 7/2002 | Restelli et al. |
| 6,428,463 B1 | 8/2002 | Ravins et al. |
| 6,428,517 B1 | 8/2002 | Hochman et al. |
| 6,432,035 B1 | 8/2002 | Ravins et al. |
| 6,432,082 B1 | 8/2002 | Chen et al. |
| 6,432,087 B1 | 8/2002 | Hoeck et al. |
| 6,436,068 B1 | 8/2002 | Bardy |
| 6,440,098 B1 | 8/2002 | Luscher et al. |
| 6,443,929 B1 | 9/2002 | Kuracina et al. |
| 6,447,480 B1 | 9/2002 | Brunel et al. |
| 6,454,743 B1 | 9/2002 | Weber et al. |
| 6,458,105 B1 | 10/2002 | Rippstein, Jr. et al. |
| 6,461,331 B1 | 10/2002 | Van Antwerp |
| 6,461,333 B1 | 10/2002 | Frezza et al. |
| 6,468,247 B1 | 10/2002 | Zamoyski |
| 6,474,375 B2 | 11/2002 | Spero et al. |
| 6,475,194 B2 | 11/2002 | Domici, Jr. et al. |
| 6,478,771 B1 | 11/2002 | Lavi et al. |
| 6,478,780 B1 | 11/2002 | Shields |
| 6,482,176 B1 | 11/2002 | Wich |
| 6,485,469 B1 | 11/2002 | Stewart et al. |
| 6,494,863 B1 | 12/2002 | Shaw et al. |
| 6,500,155 B2 | 12/2002 | Sasso |
| 6,508,755 B1 | 1/2003 | Ravins et al. |
| 6,511,454 B1 | 1/2003 | Nakao et al. |
| 6,514,230 B1 | 2/2003 | Munk et al. |
| 6,517,516 B1 | 2/2003 | Caizza |
| 6,517,517 B1 | 2/2003 | Farrugia et al. |
| 6,524,278 B1 | 2/2003 | Campbell et al. |
| 6,527,734 B2 | 3/2003 | Cragg et al. |
| 6,527,742 B1 | 3/2003 | Malenchek |
| 6,530,896 B1 | 3/2003 | Elliott |
| 6,530,903 B2 | 3/2003 | Wang et al. |
| 6,530,904 B1 | 3/2003 | Edwards et al. |
| 6,537,249 B2 | 3/2003 | Kriesell et al. |
| 6,537,252 B1 | 3/2003 | Hansen et al. |
| 6,544,234 B1 | 4/2003 | Gabriel et al. |
| 6,547,764 B2 | 4/2003 | Larsen et al. |
| 6,551,275 B2 | 4/2003 | Fontayne et al. |
| 6,551,276 B1 | 4/2003 | Mann et al. |
| 6,551,278 B1 | 4/2003 | Geitz |
| 6,551,299 B2 | 4/2003 | Miyoshi et al. |
| 6,554,798 B1 | 4/2003 | Mann et al. |
| 6,558,351 B1 | 5/2003 | Steil et al. |
| 6,558,357 B1 | 5/2003 | Hoeck |
| 6,558,365 B2 | 5/2003 | Zinger et al. |
| 6,565,533 B1 | 5/2003 | Smith et al. |
| 6,565,538 B2 | 5/2003 | Quinn et al. |
| 6,565,553 B2 | 5/2003 | Sadowski et al. |
| 6,569,115 B1 | 5/2003 | Barker et al. |
| 6,572,584 B1 | 6/2003 | Shaw et al. |
| 6,572,585 B2 | 6/2003 | Choi et al. |
| 6,572,590 B1 | 6/2003 | Stevens et al. |
| 6,575,939 B1 | 6/2003 | Brunel et al. |
| 6,579,256 B2 | 6/2003 | Hughes |
| 6,582,405 B2 | 6/2003 | Kawagishi et al. |
| 6,584,910 B1 | 7/2003 | Plass |
| 6,585,690 B1 | 7/2003 | Hoeck et al. |
| 6,585,693 B1 | 7/2003 | Dischler |
| 6,585,702 B1 | 7/2003 | Brunel et al. |
| 6,589,158 B2 | 7/2003 | Winkler |
| 6,592,508 B1 | 7/2003 | Ravins et al. |
| 6,592,555 B1 | 7/2003 | Wen-Pi et al. |
| 6,592,556 B1 | 7/2003 | Thorne |
| 6,595,962 B1 | 7/2003 | Perthu et al. |
| 6,599,268 B1 | 7/2003 | Townsend et al. |
| 6,599,269 B1 | 7/2003 | Lewandowski et al. |
| 6,599,272 B1 | 7/2003 | Hjertman et al. |
| 6,605,058 B1 | 8/2003 | Wich |
| 6,605,067 B1 | 8/2003 | Larsen et al. |
| 6,605,073 B1 | 8/2003 | Pressly, Sr. et al. |
| 6,607,508 B2 | 8/2003 | Knauer |
| 6,607,509 B2 | 8/2003 | Bobroff et al. |
| 6,613,019 B2 | 9/2003 | Munk et al. |
| 6,613,022 B1 | 9/2003 | Doyle |
| 6,616,630 B1 | 9/2003 | Woehr et al. |
| 6,616,638 B2 | 9/2003 | Peters, III |
| 6,616,639 B2 | 9/2003 | Gagnieux et al. |
| 6,620,136 B1 | 9/2003 | Pressly, Sr. et al. |
| 6,620,137 B2 | 9/2003 | Kirchhofer et al. |
| 6,620,138 B1 | 9/2003 | Marrgi et al. |
| 6,623,455 B2 | 9/2003 | Small et al. |
| 6,623,458 B2 | 9/2003 | Woehr et al. |
| 6,623,459 B1 | 9/2003 | Doyle |
| 6,626,309 B1 | 9/2003 | Jansen et al. |
| 6,626,864 B2 | 9/2003 | Jansen et al. |
| 6,629,957 B1 | 10/2003 | Wiklund et al. |
| 6,629,959 B2 | 10/2003 | Kuracina et al. |
| 6,632,198 B2 | 10/2003 | Caizza |
| 6,637,587 B2 | 10/2003 | Britton |
| 6,638,248 B1 | 10/2003 | Brewer et al. |
| 6,638,255 B1 | 10/2003 | Weber et al. |
| 6,641,561 B1 | 11/2003 | Hill et al. |
| 6,645,181 B1 | 11/2003 | Lavi et al. |
| 6,652,482 B2 | 11/2003 | Hochman |
| 6,656,164 B1 | 12/2003 | Smith et al. |
| 6,659,975 B2 | 12/2003 | Amano et al. |
| 6,659,982 B2 | 12/2003 | Douglas et al. |
| 6,663,593 B2 | 12/2003 | Ito et al. |
| 6,669,666 B1 | 12/2003 | Lu et al. |
| 6,673,034 B2 | 1/2004 | Castellano |
| 6,673,044 B2 | 1/2004 | Righi et al. |
| 6,673,049 B2 | 1/2004 | Hommann et al. |
| 6,678,550 B2 | 1/2004 | Hubbard, Jr. |
| 6,679,863 B2 | 1/2004 | Bush, Jr. et al. |
| 6,679,864 B2 | 1/2004 | Gagnieux et al. |
| 6,685,676 B2 | 2/2004 | Jansen et al. |
| 6,685,677 B2 | 2/2004 | Green |
| 6,689,091 B2 | 2/2004 | Bui et al. |
| 6,689,106 B2 | 2/2004 | Bush, Jr. et al. |
| 6,689,107 B1 | 2/2004 | Choudhary et al. |
| 6,689,108 B2 | 2/2004 | Lavi et al. |
| 6,692,470 B2 | 2/2004 | Sanpietro |
| 6,692,471 B2 | 2/2004 | Boudreaux |
| 6,699,218 B2 | 3/2004 | Flaherty et al. |
| 6,702,784 B1 | 3/2004 | Sheckler et al. |
| 6,706,011 B1 | 3/2004 | Murphy-Chutorian et al. |
| 6,706,015 B2 | 3/2004 | Bang et al. |
| 6,706,019 B1 | 3/2004 | Parker et al. |
| 6,709,416 B2 | 3/2004 | Hjertman et al. |
| 6,712,787 B1 | 3/2004 | Dysarz |
| 6,712,788 B2 | 3/2004 | Righi et al. |
| 6,716,191 B2 | 4/2004 | Sergio et al. |
| 6,716,197 B2 | 4/2004 | Svendsen et al. |
| 6,716,198 B2 | 4/2004 | Larsen et al. |
| 6,719,721 B1 | 4/2004 | Okazaki et al. |
| 6,719,728 B2 | 4/2004 | Mason et al. |
| 6,719,730 B2 | 4/2004 | Jansen et al. |
| 6,723,068 B2 | 4/2004 | Lavi et al. |
| 6,723,072 B2 | 4/2004 | Flaherty et al. |
| 6,726,655 B1 | 4/2004 | Lieberman et al. |
| 6,726,658 B2 | 4/2004 | Hochman |
| 6,726,661 B2 | 4/2004 | Munk et al. |
| 6,726,662 B2 | 4/2004 | Altman |
| 6,730,059 B2 | 5/2004 | Caizza et al. |
| 6,736,800 B2 | 5/2004 | Rindlisbacher et al. |
| 6,740,059 B2 | 5/2004 | Flaherty |
| 6,743,203 B2 | 6/2004 | Pickhard et al. |
| 6,749,833 B2 | 6/2004 | Raghavan et al. |
| 6,752,782 B2 | 6/2004 | Liao et al. |
| 6,752,784 B2 | 6/2004 | Tsai et al. |
| 6,752,798 B2 | 6/2004 | McWethy et al. |
| 6,761,706 B2 | 7/2004 | Vaillancourt |
| 6,767,336 B1 | 7/2004 | Kaplan |
| 6,971,999 B2 | 12/2005 | Py et al. |

| | | |
|---|---|---|
| 2001/0037087 A1 | 11/2001 | Knauer |
| 2002/0123719 A1 | 9/2002 | Lavi et al. |
| 2002/0123736 A1 | 9/2002 | Fowles et al. |
| 2002/0133122 A1 | 9/2002 | Giambattista et al. |
| 2003/0023203 A1 | 1/2003 | Lavi et al. |
| 2003/0036725 A1 | 2/2003 | Lavi et al. |
| 2003/0093036 A1 | 5/2003 | Crossman et al. |
| 2003/0105430 A1 | 6/2003 | Lavi et al. |
| 2003/0109827 A1 | 6/2003 | Lavi et al. |
| 2003/0125671 A1 | 7/2003 | Aramata et al. |

\* cited by examiner

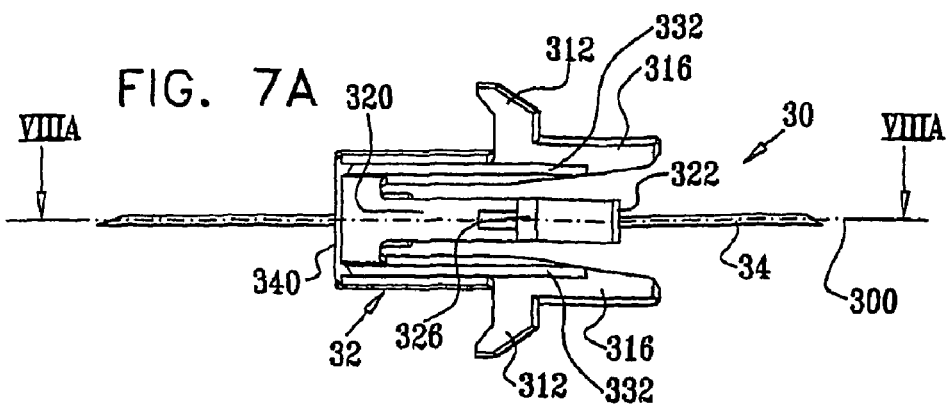
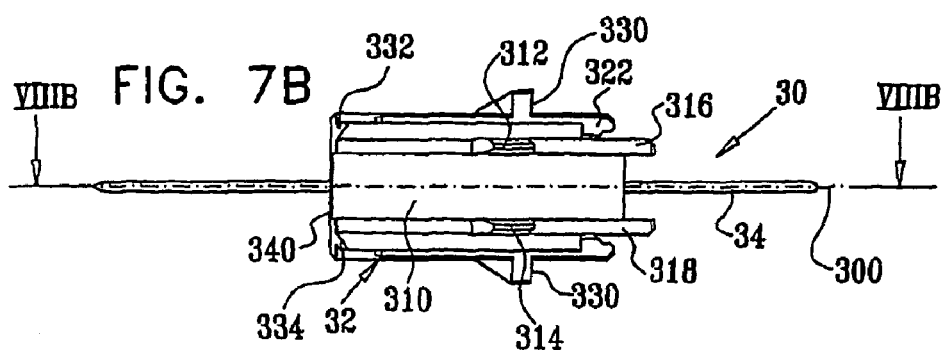
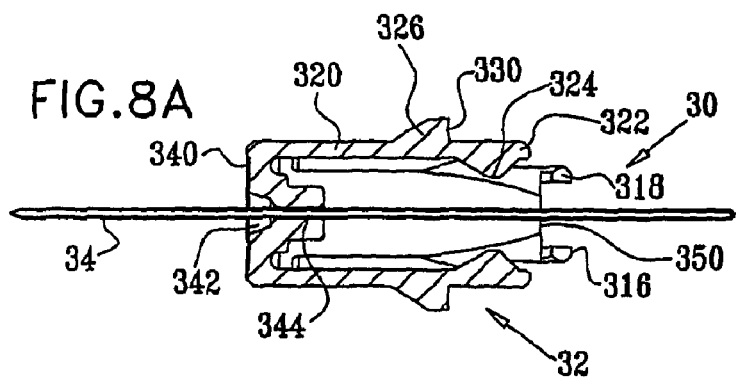
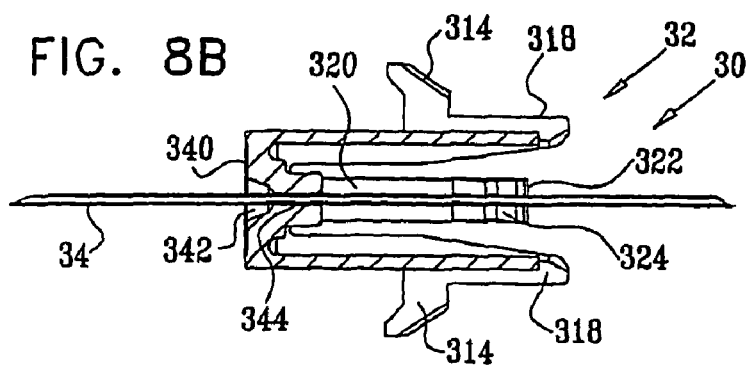

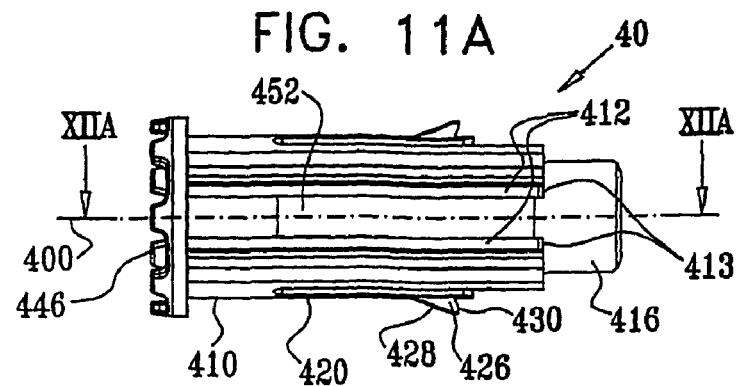
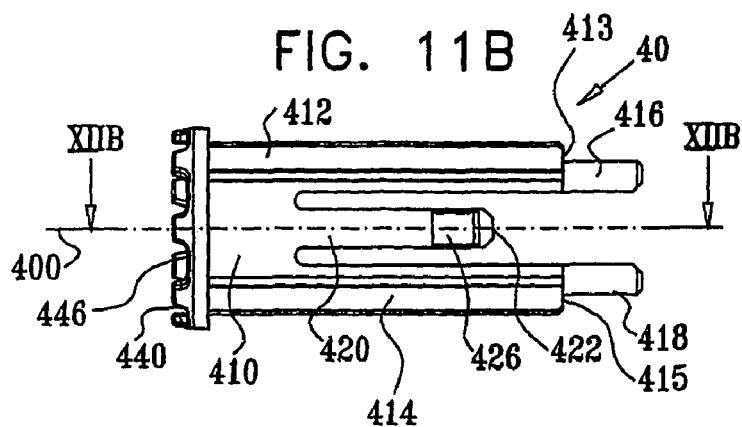
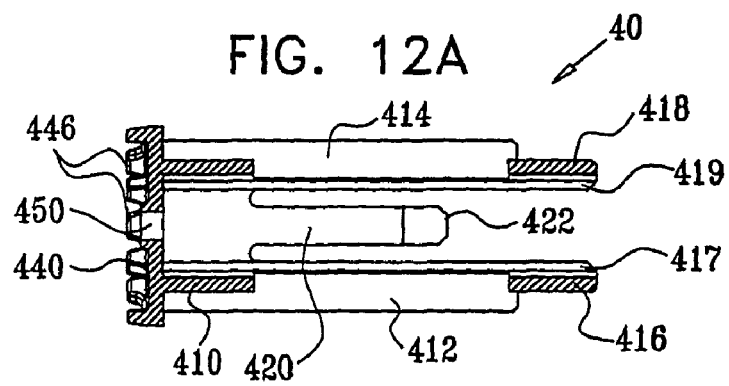
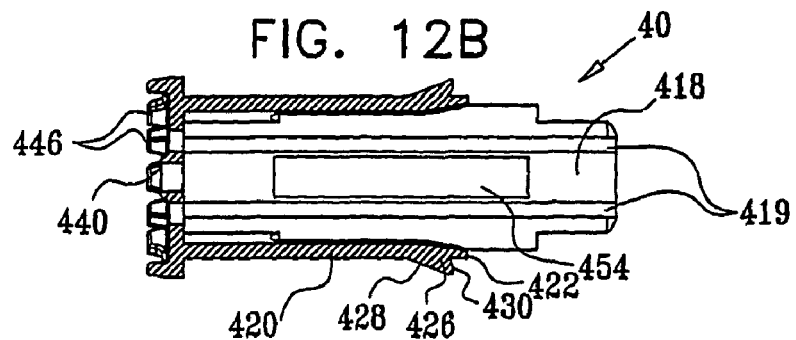

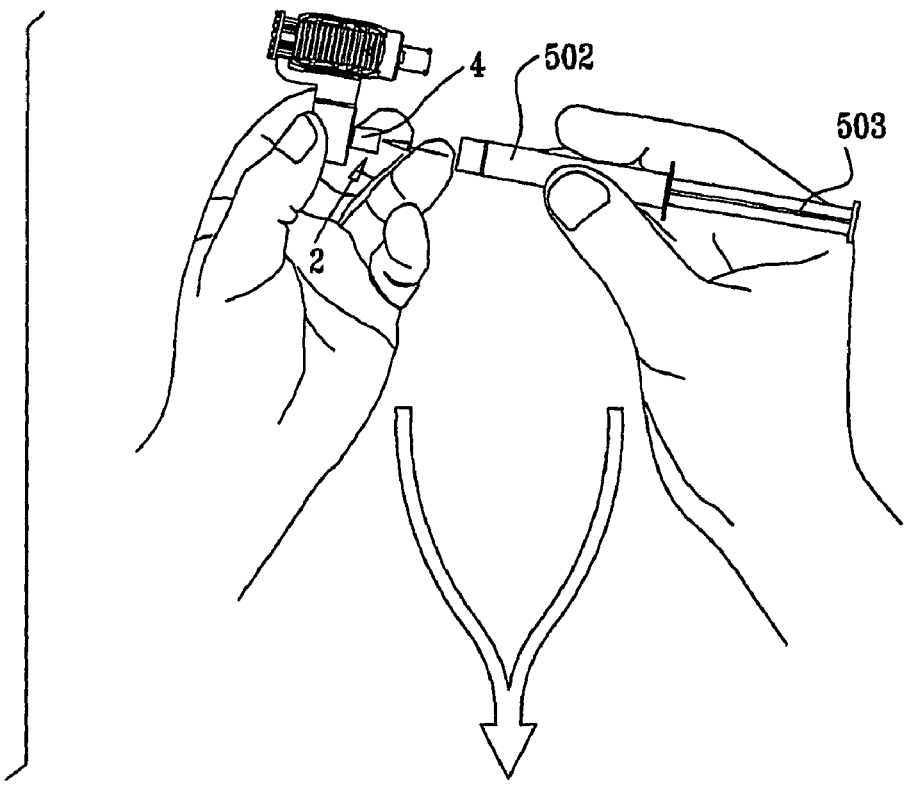
FIG. 14A
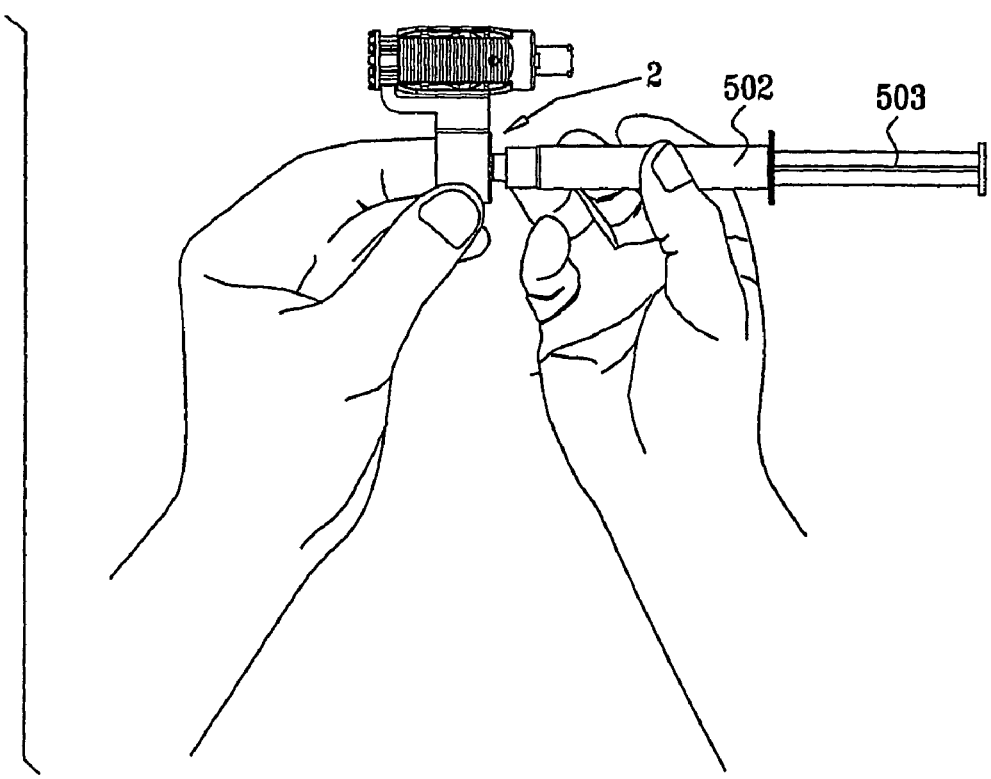

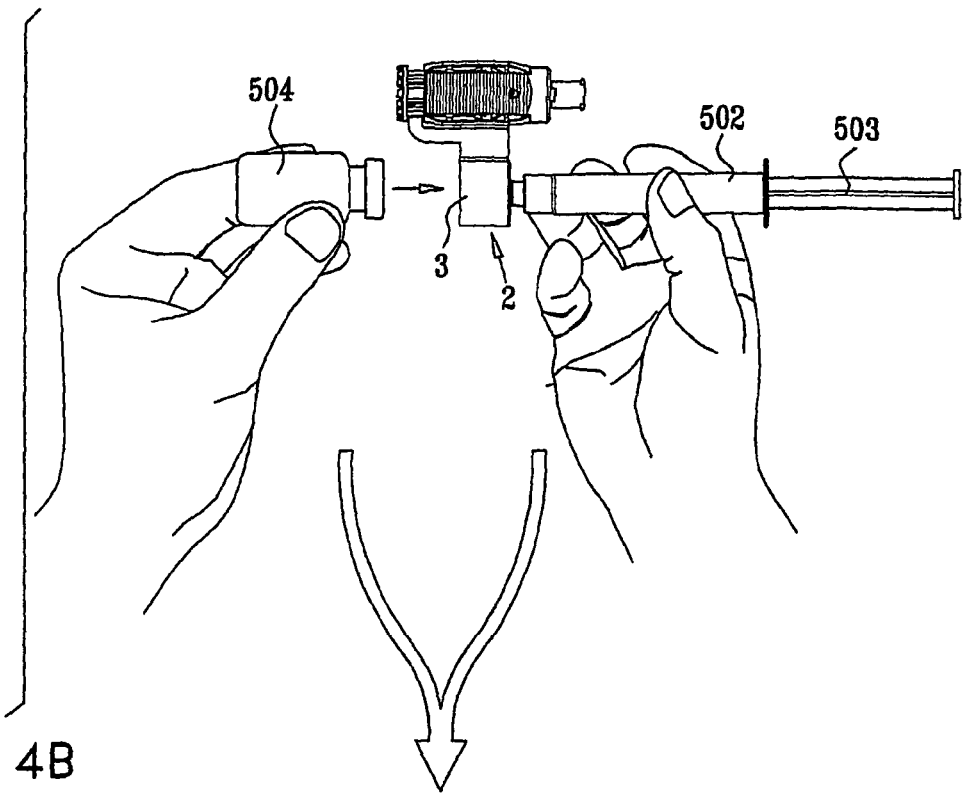
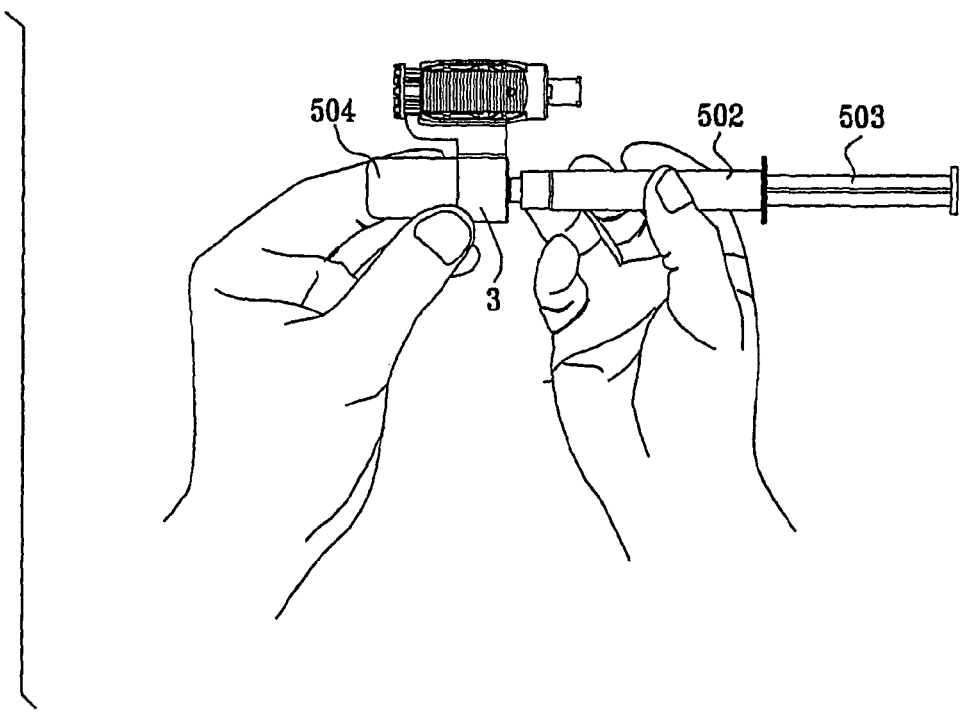
FIG. 14B

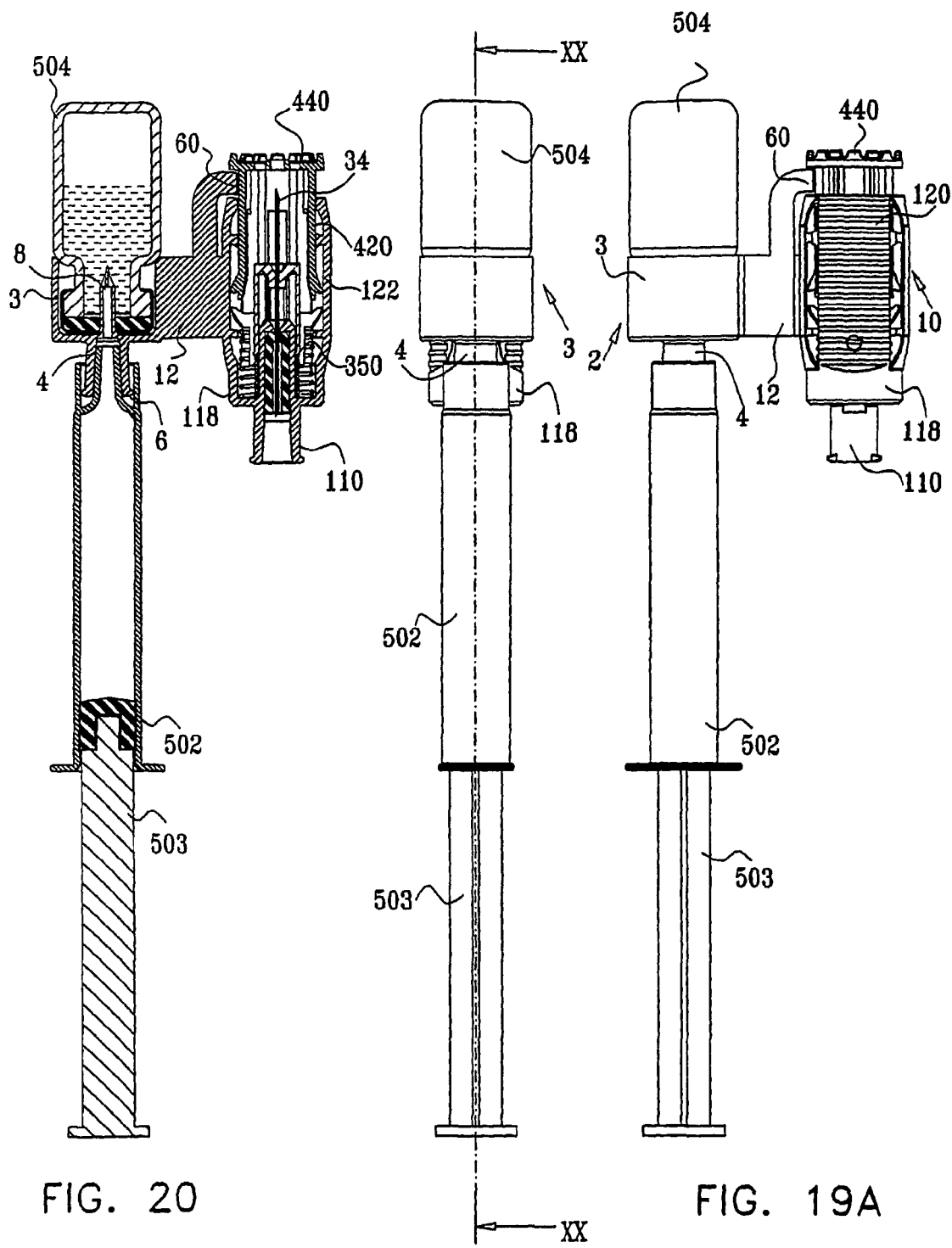

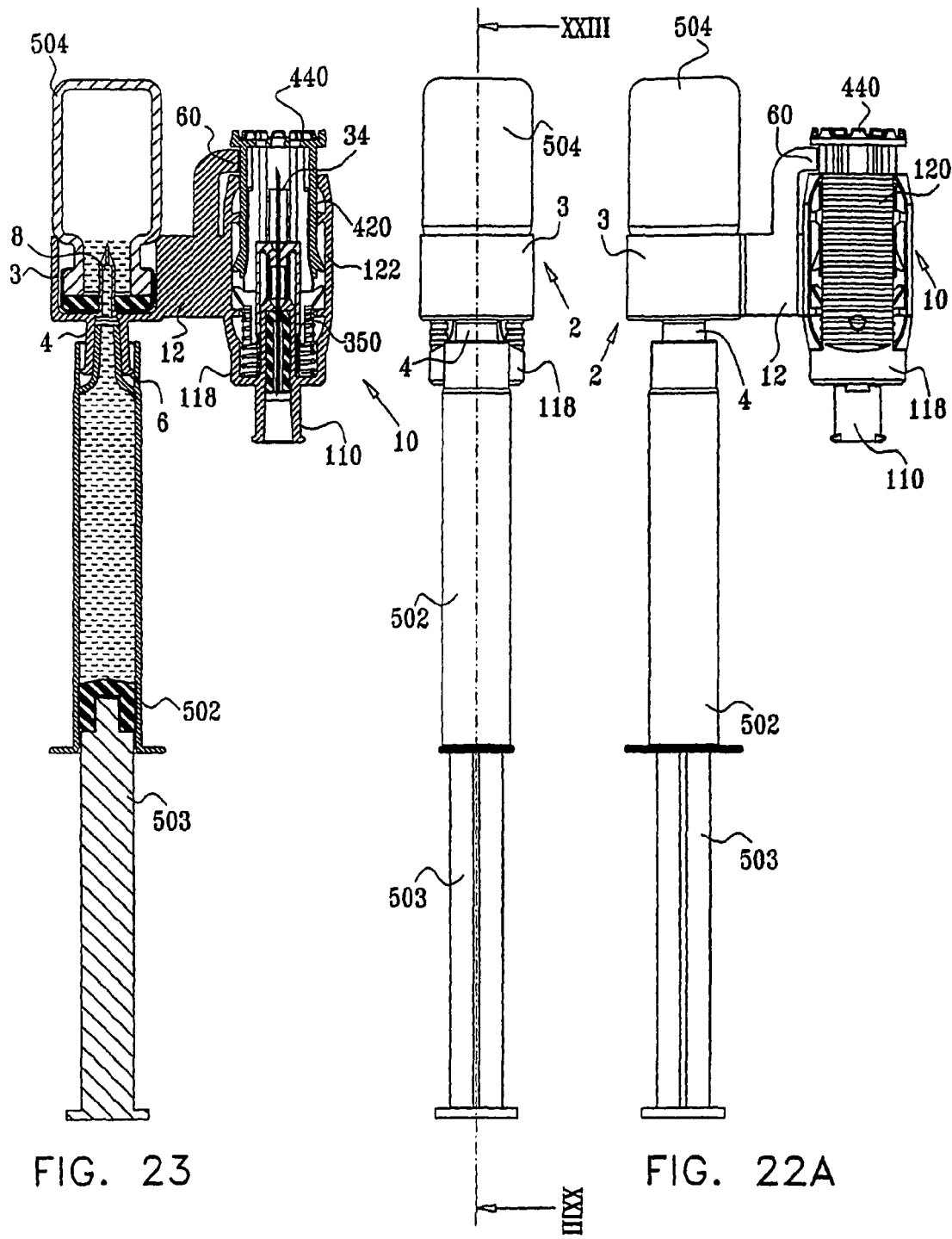

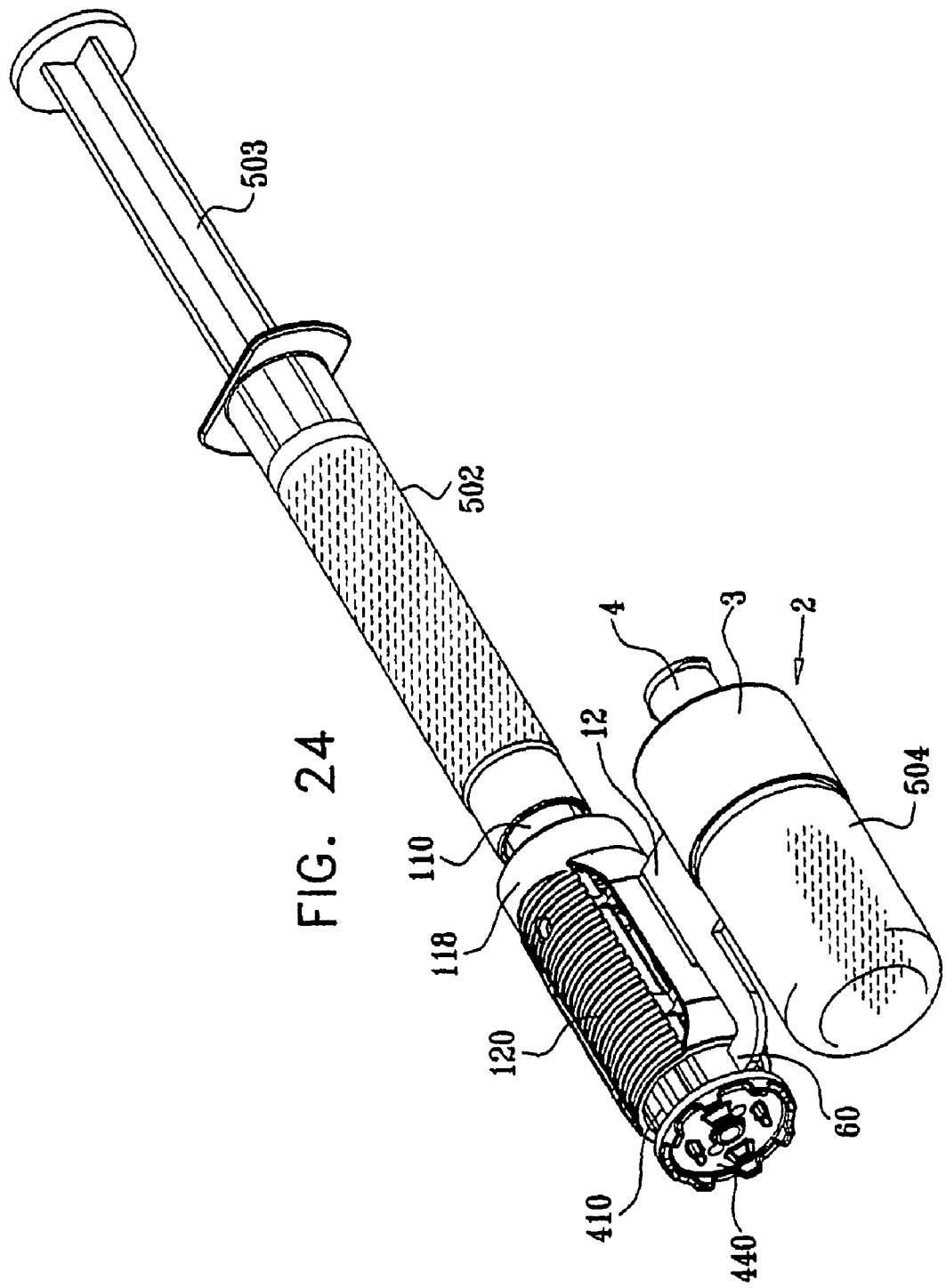

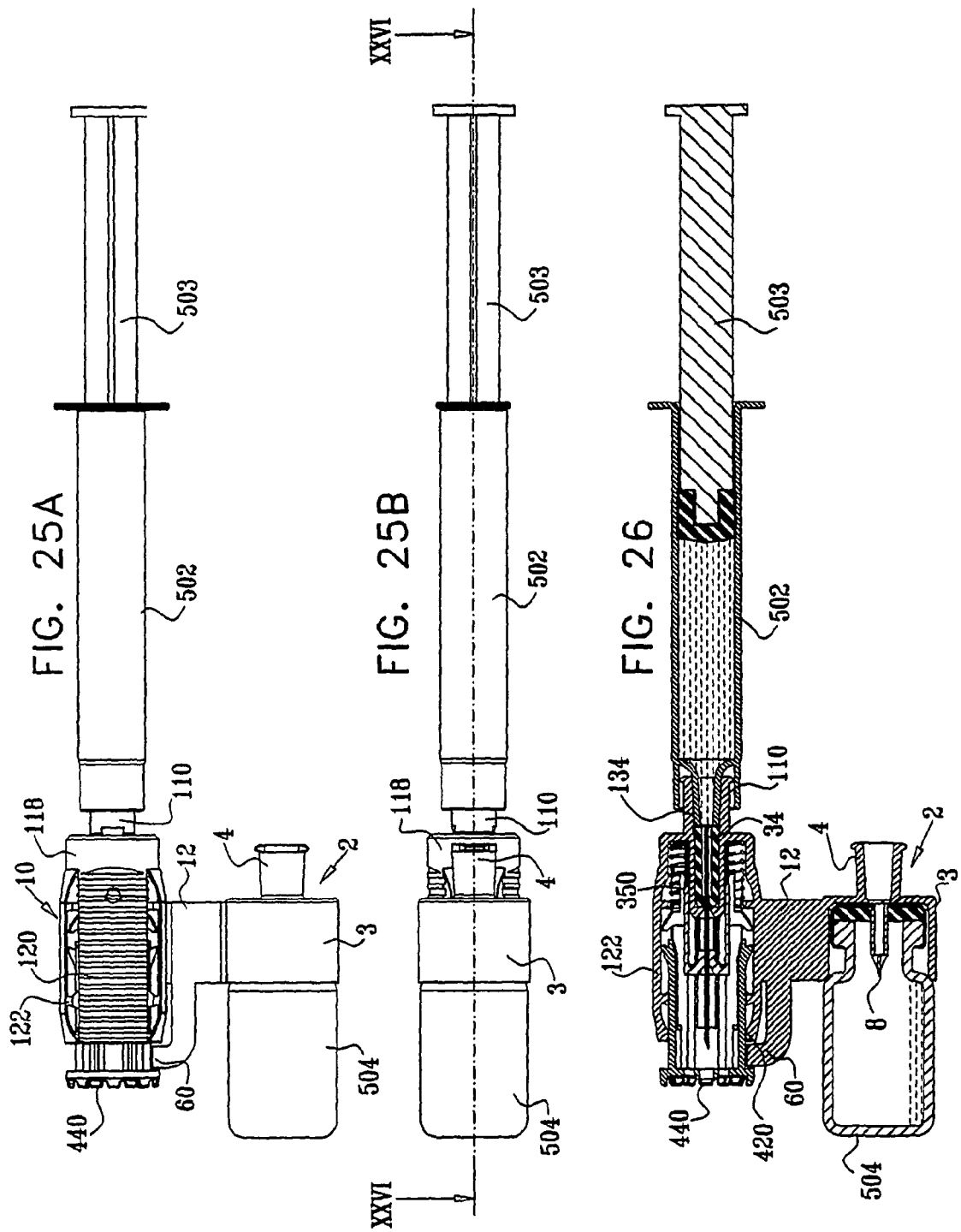

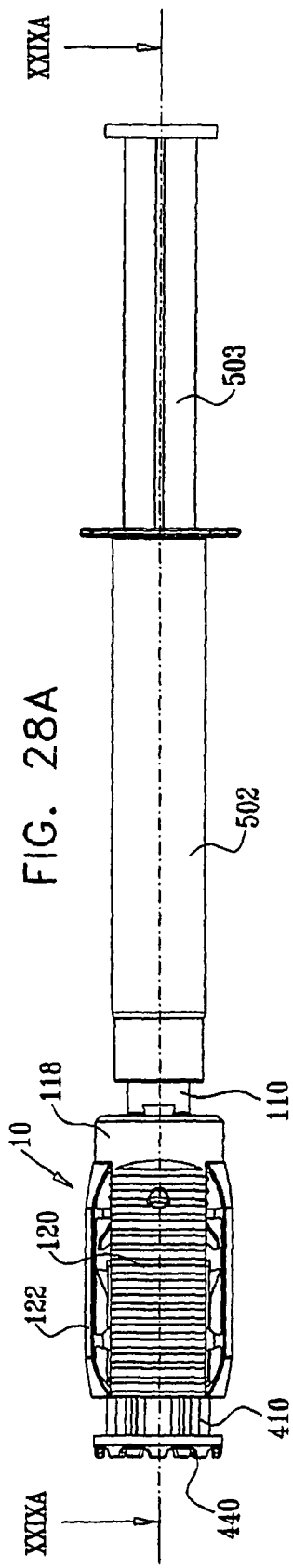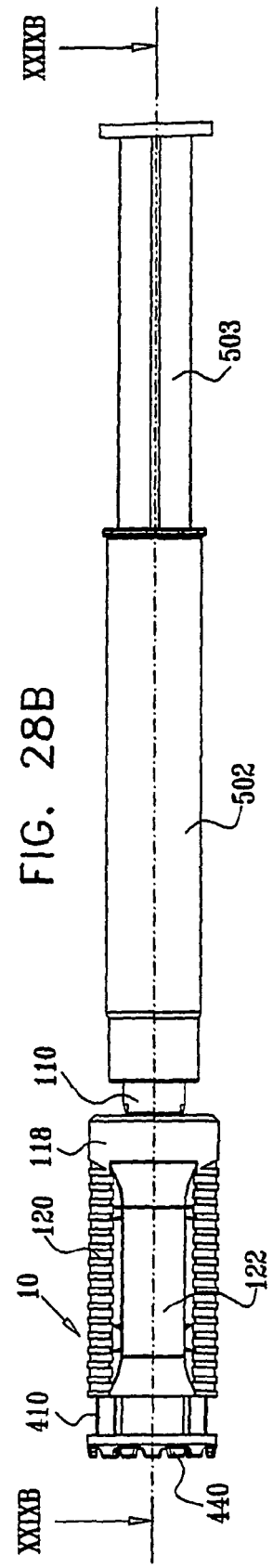

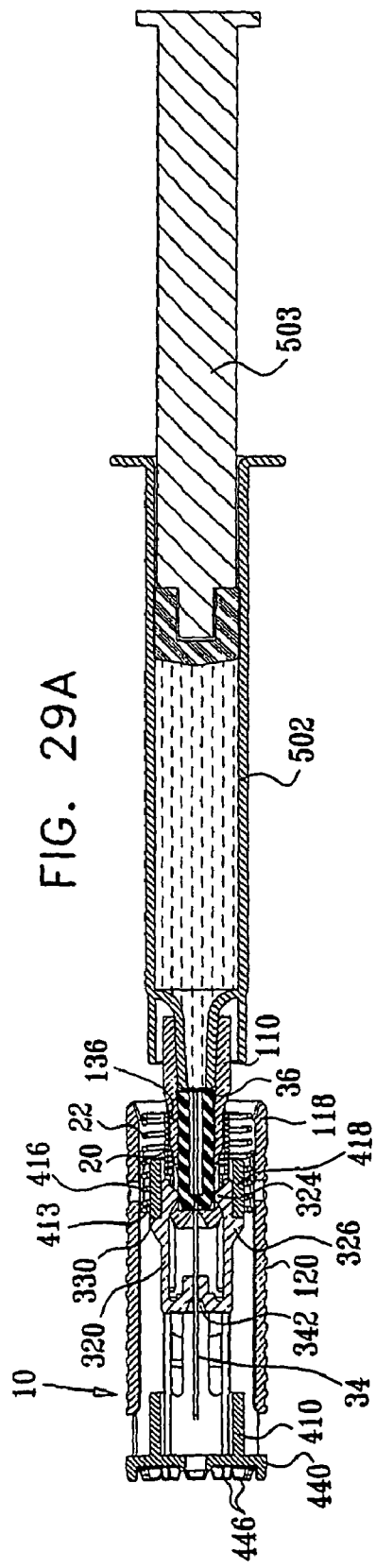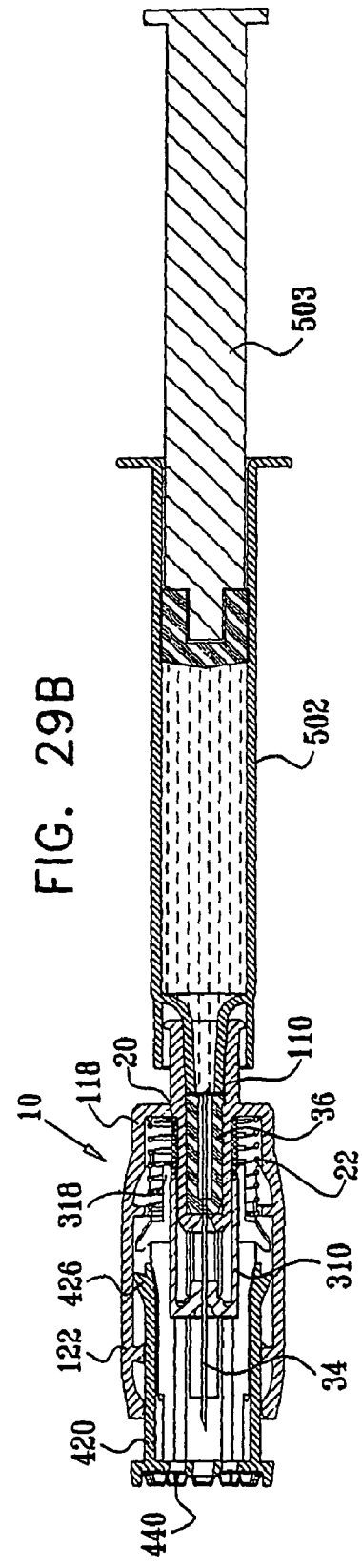

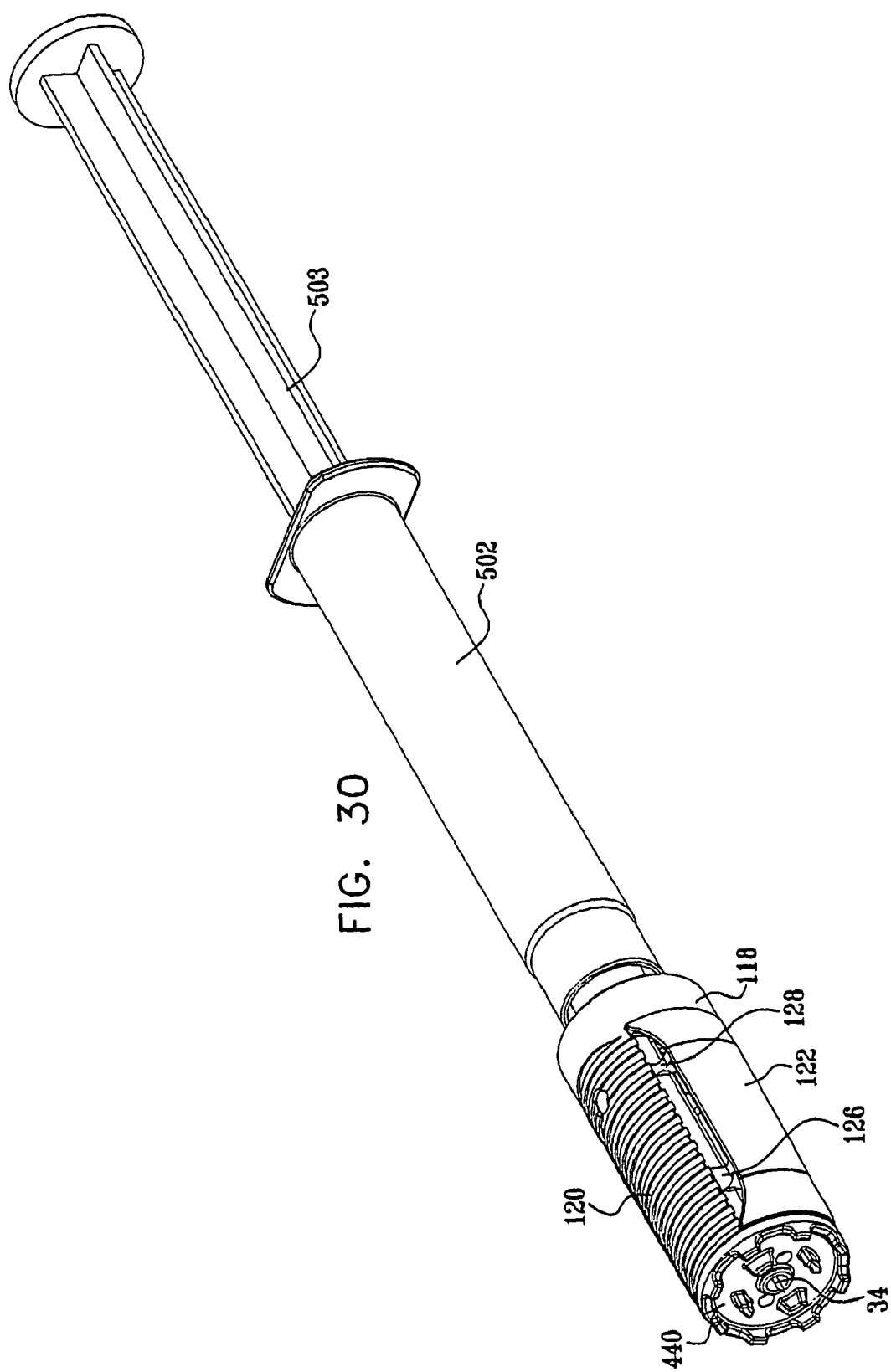

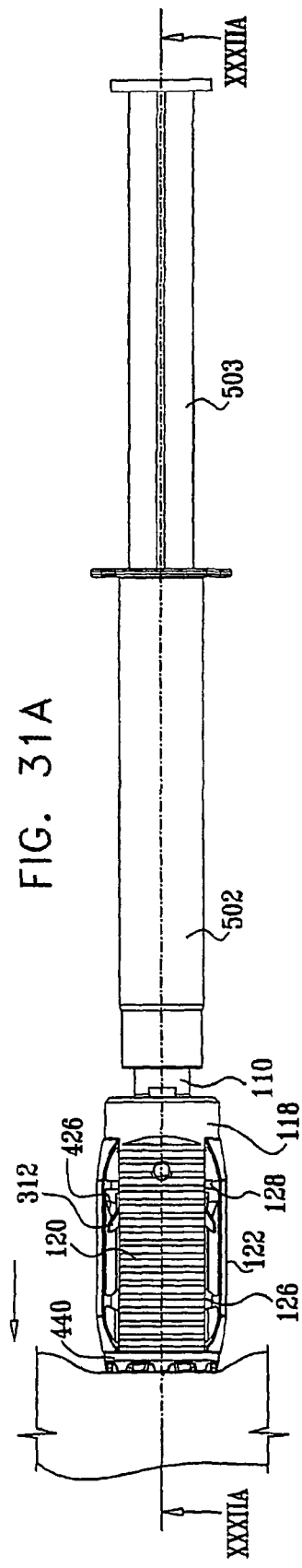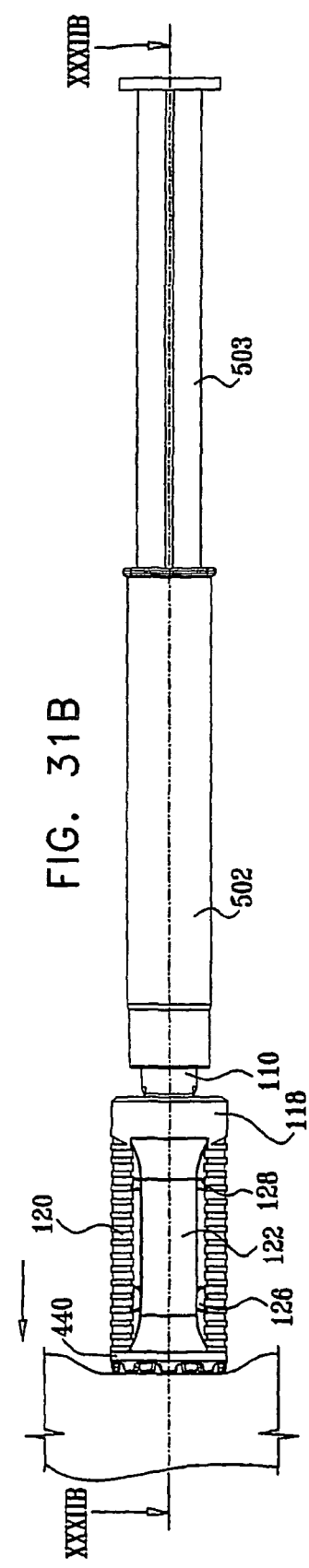
FIG. 31A
FIG. 31B

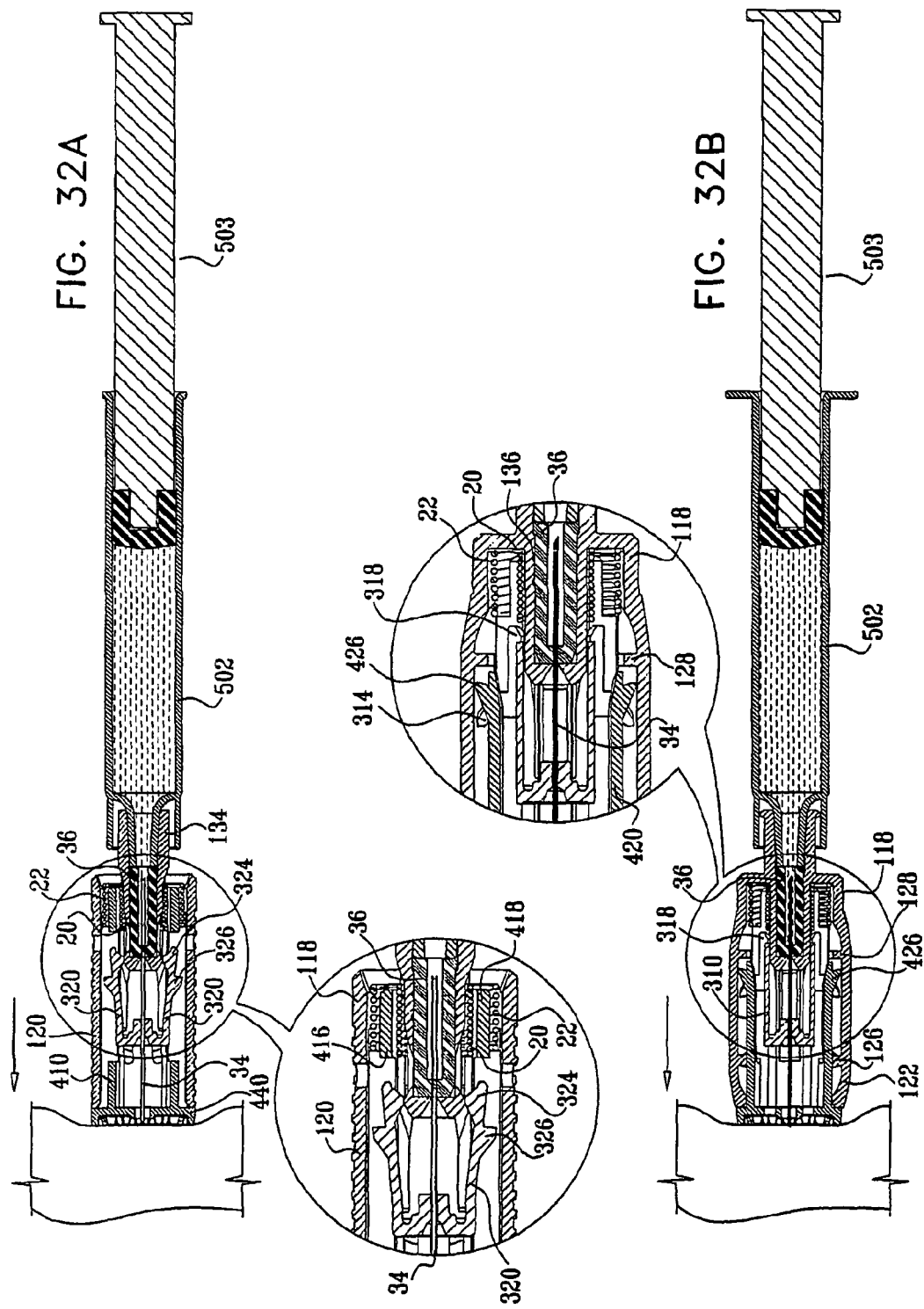

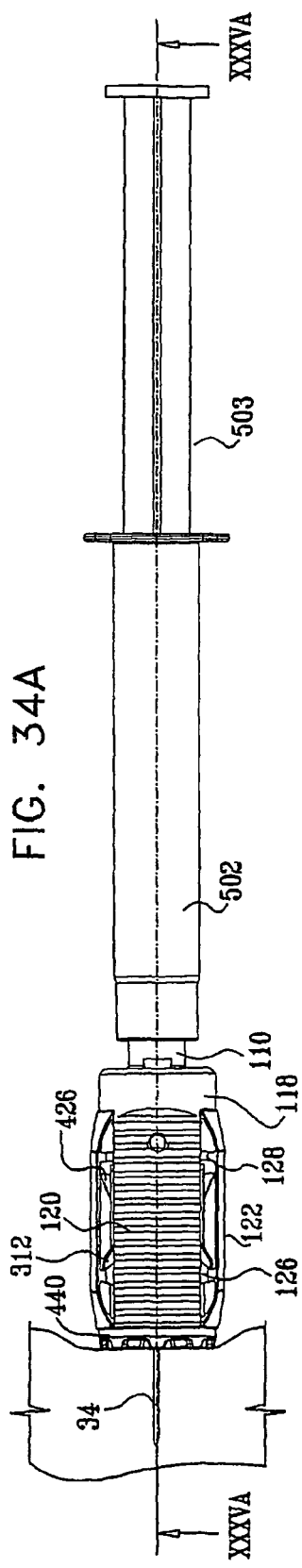
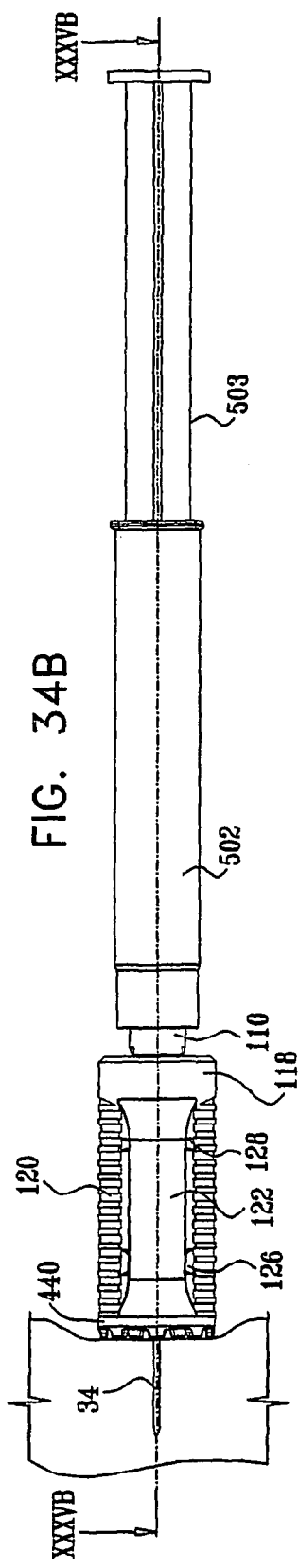
FIG. 34A
FIG. 34B

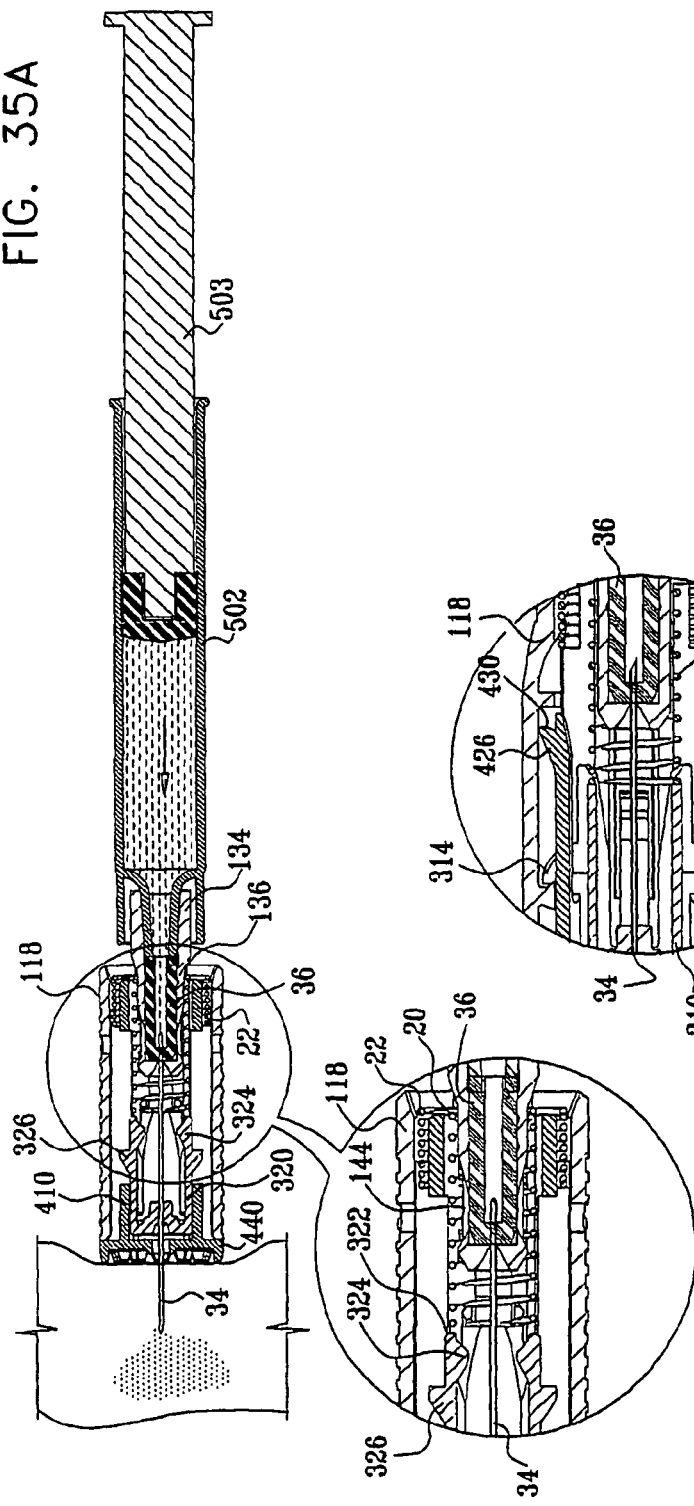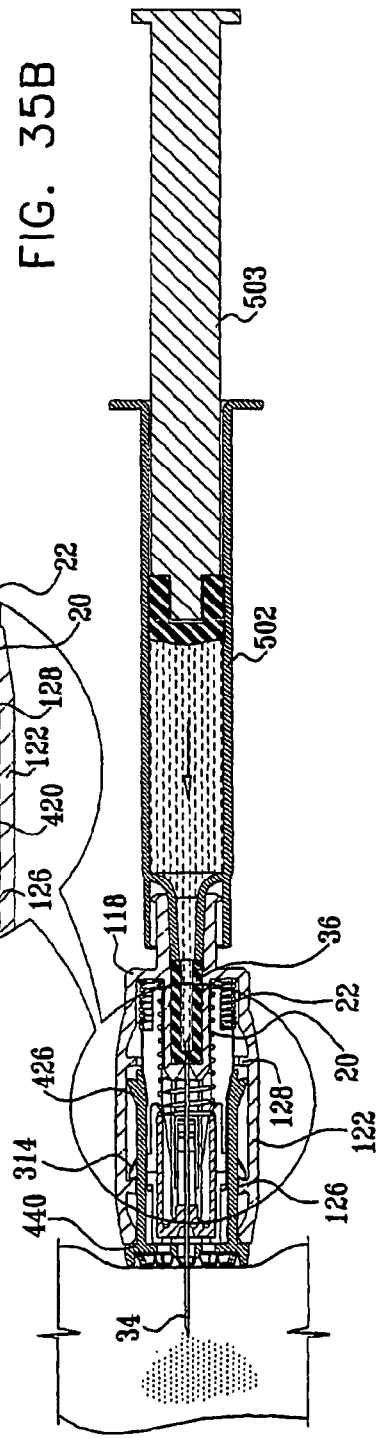

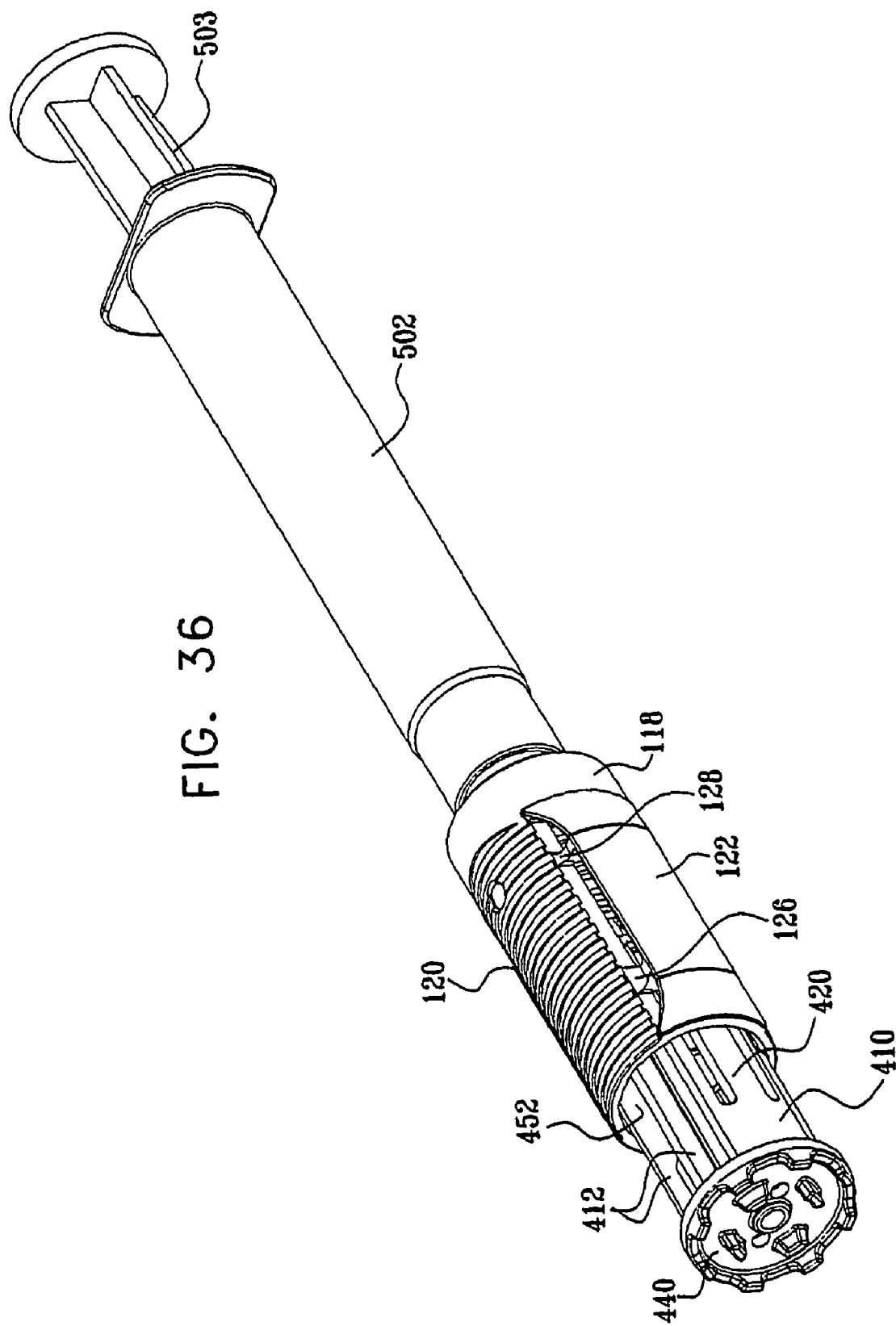

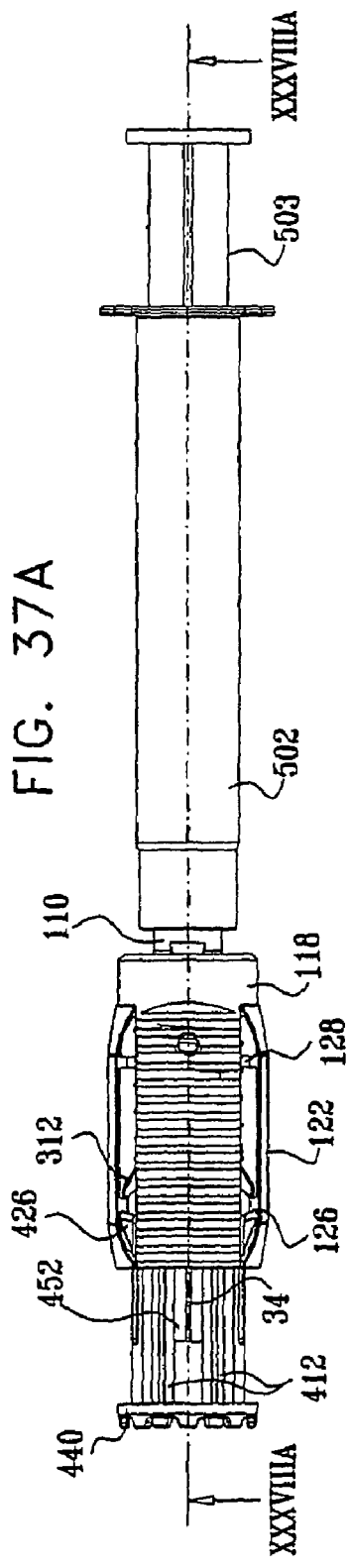
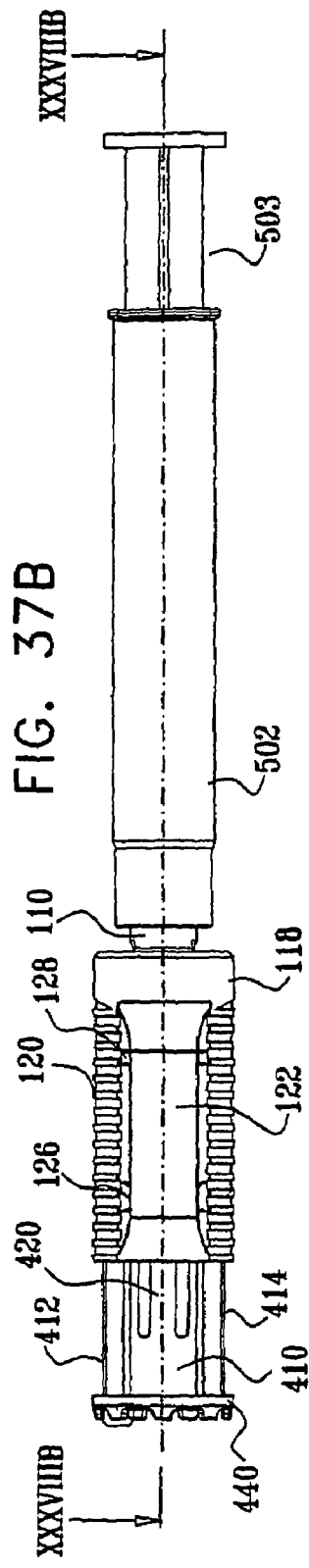
FIG. 37A
FIG. 37B

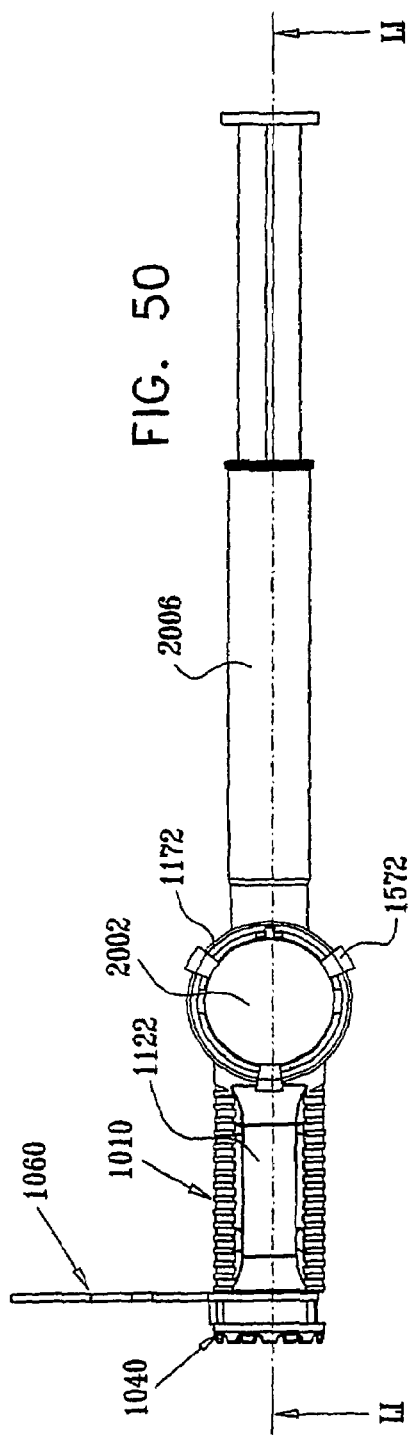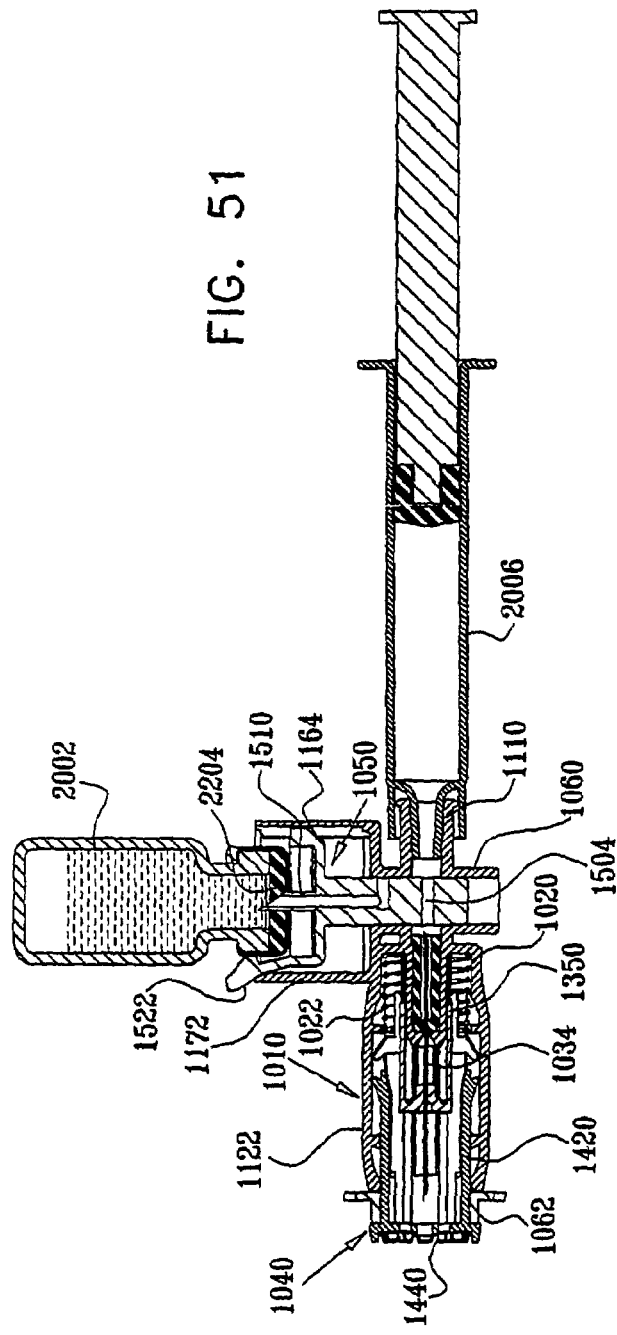

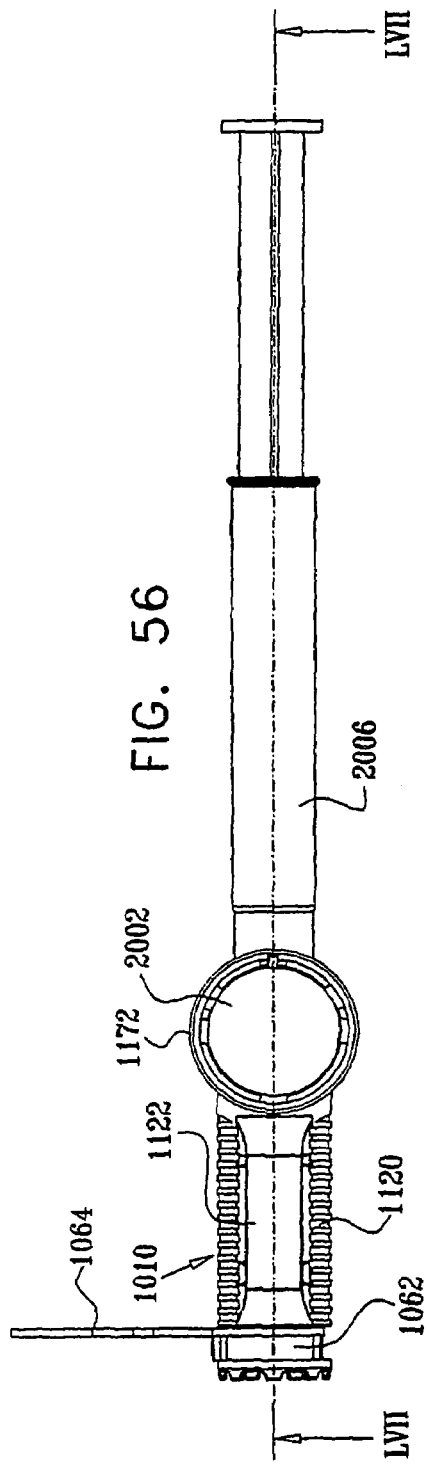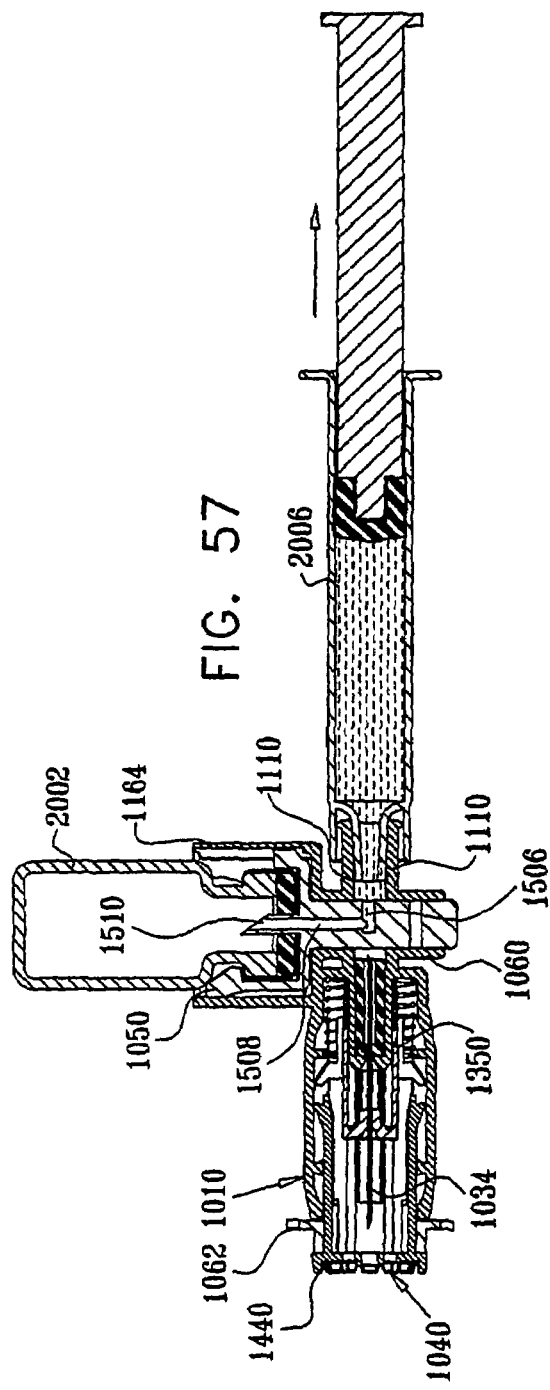

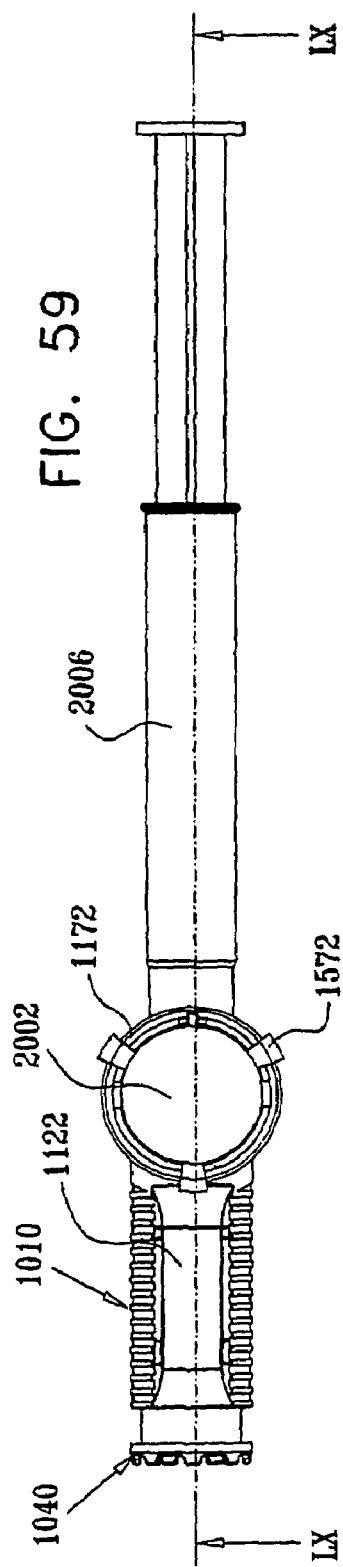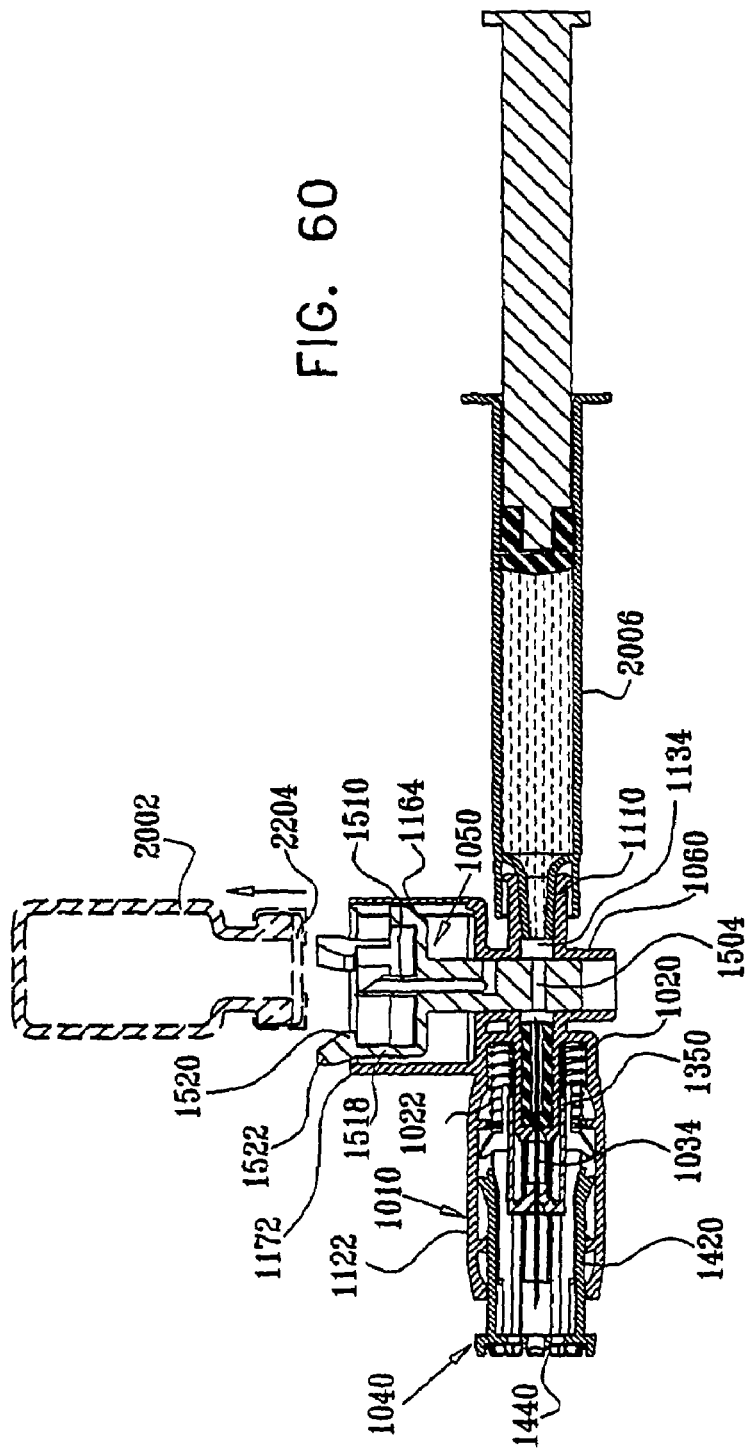

MEDICINAL CONTAINER ENGAGEMENT AND AUTOMATIC NEEDLE DEVICE

FIELD OF THE INVENTION

The present invention relates to medicinal container engagement and automatic needle devices for hypodermic syringes generally.

BACKGROUND OF THE INVENTION

The following U.S. patents and patent application Publications are believed to represent the current state of the art:
U.S. Pat. Nos. 4,058,121; 4,474,572; 4,475,906; 4,484,910; 4,487,602; 4,505,710; 4,512,767; 4,515,590; 4,518,387; 4,529,401; 4,529,403; 4,530,695; 4,534,759; 4,543,101; 4,547,189; 4,553,962; 4,573,993; 4,573,970; 4,573,976; 4,578,061; 4,578,064; 4,580,561; 4,592,744; 4,594,073; 4,596,558; 4,597,753; 4,600,403; 4,601,708; 4,613,328; 4,620,540; 4,620,847; 4,624,660; 4,650,468; 4,658,830; 4,659,326; 4,664,651; 4,664,654; 4,666,436; 4,672,967; 4,681,565; 4,687,465; 4,687,467; 4,689,042; 4,699,614; 4,710,170; 4,722,733; 4,723,937; 4,735,618; 4,738,663; 4,743,234; 4,744,955; 4,745,907; 4,747,829; 4,747,831; 4,753,636; 4,755,169; 4,758,227; 4,758,230; 4,758,231; 4,766,908; 4,767,407; 4,767,413; 4,770,655; 4,781,683; 4,781,685; 4,781,688; 4,784,640; 4,787,384; 4,787,893; 4,790,823; 4,790,827; 4,795,432; 4,795,433; 4,798,587; 4,799,921; 4,804,370; 4,808,169; 4,813,937; 4,813,940; 4,820,275; 4,820,286; 4,826,484; 4,826,489; 4,826,490; 4,828,548; 4,832,682; 4,832,693; 4,834,704; 4,834,718; 4,842,598; 4,846,811; 4,850,961; 4,850,968; 4,850,971; 4,850,976; 4,850,977; 4,850,994; 4,861,338; 4,863,427; 4,863,435; 4,863,436; 4,865,592; 4,874,372; 4,874,382; 4,883,466; 4,883,472; 4,886,499; 4,887,998; 4,892,107; 4,892,523; 4,894,054; 4,894,055; 4,898,589; 4,900,303; 4,900,307; 4,900,311; 4,902,279; 4,904,242; 4,906,236; 4,908,022; 4,909,794; 4,909,795; 4,911,706; 4,913,702; 4,915,702; 4,917,672; 4,919,146; 4,919,657; 4,923,443; 4,923,445; 4,927,414; 4,929,237; 4,929,241; 4,931,040; 4,932,944; 4,932,946; 4,932,947; 4,935,013; 4,935,014; 4,936,830; 4,941,879; 4,944,723; 4,944,725; 4,946,441; 4,950,240; 4,950,241; 4,950,250; 4,950,252; 4,955,866; 4,955,868; 4,955,869; 4,955,870; 4,961,728; 4,966,589; 4,966,592; 4,966,593; 4,973,310; 4,973,317; 4,976,704; 4,988,335; 4,988,339; 4,994,045; 4,998,921; 4,998,922; 5,000,736; 5,000,737; 5,002,548; 5,007,903; 5,011,475; 5,015,240; 5,017,187; 5,019,043; 5,019,044; 5,019,047; 5,019,048; 5,021,059; 5,024,665; 5,026,349; 5,030,208; 5,034,003; 5,037,306; 5,037,382; 5,037,393; 5,037,400; 5,041,094; 5,042,977; 5,045,066; 5,047,016; 5,049,133; 5,049,136; 5,053,010; 5,053,018; 5,055,102; 5,057,086; 5,057,089; 5,059,180; 5,059,185; 5,061,249; 5,061,251; 5,064,419; 5,067,490; 5,067,948; 5,071,353; 5,080,104; 5,084,027; 5,084,029; 5,084,030; 5,085,640; 5,085,641; 5,085,642; 5,088,986; 5,088,988; 5,092,843; 5,092,851; 5,092,852; 5,092,853; 5,098,382; 5,098,400; 5,098,401; 5,102,393; 5,102,397; 5,104,378; 5,104,380; 5,104,384; 5,104,385; 5,106,370; 5,106,372; 5,106,379; 5,108,378; 5,108,379; 5,112,307; 5,112,316; 5,114,404; 5,120,310; 5,120,314; 5,120,321; 5,122,118; 5,122,124; 5,125,898; 5,125,899; 5,127,910; 5,135,507; 5,135,510; 5,137,515; 5,137,516; 5,141,496; 5,143,414; 5,147,311; 5,147,326; 5,147,327; 5,149,323; 5,152,751; 5,156,599; 5,160,326; 5,163,916; 5,163,917; 5,163,918; 5,167,632; 5,167,641; 5,169,389; 5,169,392; 5,176,641; 5,176,655; 5,176,656; 5,176,657; 5,183,468; 5,183,469; 5,188,614; 5,190,526; 5,193,552; 5,195,982; 5,195,983; 5,195,985; 5,199,952; 5,201,708; 5,201,710; 5,205,826; 5,205,827; 5,207,646; 5,207,699; 5,209,739; 5,211,628; 5,211,629; 5,215,524; 5,215,533; 5,215,534; 5,215,535; 5,215,536; 5,217,437; 5,219,338; 5,221,262; 5,222,943; 5,222,947; 5,222,974; 5,224,936; 5,226,882; 5,228,883; 5,232,457; 5,232,458; 5,238,654; 5,242,388; 5,242,401; 5,242,416; 5,242,420; 5,246,428; 5,250,031; 5,256,152; 5,257,976; 5,261,894; 5,263,933; 5,267,961; 5,267,963; 5,269,761; 5,269,762; 5,269,766; 5,273,532; 5,273,538; 5,273,539; 5,273,541; 5,273,544; 5,279,554; 5,279,566; 5,279,576; 5,279,577; 5,279,579; 5,279,581; 5,279,582; 5,279,583; 5,279,590; 5,282,793; 5,282,822; 5,282,827; 5,284,479; 5,290,233; 5,290,239; 5,290,240; 5,290,254; 5,292,314; 5,295,963; 5,295,965; 5,295,972; 5,295,973; 5,295,974; 5,295,975; 5,300,029; 5,300,030; 5,300,040; 5,300,045; 5,304,137; 5,304,138; 5,306,251; 5,306,258; 5,308,332; 5,311,841; 5,312,353; 5,312,366; 5,312,368; 5,312,370; 5,312,371; 5,312,372; 5,314,503; 5,318,538; 5,320,609; 5,322,517; 5,324,265; 5,328,475; 5,328,482; 5,328,484; 5,330,430; 5,334,149; 5,334,158; 5,334,173; 5,336,180; 5,336,187; 5,336,199; 5,338,303; 5,338,311; 5,342,310; 5,342,320; 5,344,407; 5,344,408; 5,346,475; 5,346,480; 5,346,481; 5,348,544; 5,352,200; 5,352,202; 5,352,203; 5,354,287; 5,356,387; 5,358,489; 5,360,410; 5,364,362; 5,364,370; 5,366,447; 5,368,568; 5,368,570; 5,368,571; 5,370,619; 5,370,626; 5,374,250; 5,378,240; 5,383,857; 5,385,550; 5,385,551; 5,385,557; 5,389,076; 5,389,085; 5,391,151; 5,391,183; 5,395,317; 5,395,337; 5,399,163; 5,401,246; 5,401,249; 5,401,251; 5,403,286; 5,403,287; 5,405,326; 5,405,327; 5,407,436; 5,409,466; 5,411,487; 5,415,638; 5,415,645; 5,415,648; 5,419,766; 5,419,773; 5,423,746; 5,425,715; 5,425,722; 5,429,611; 5,429,612; 5,429,613; 5,431,631; 5,431,632; 5,433,712; 5,445,618; 5,445,620; 5,451,210; 5,458,576; 5,458,580; 5,460,611; 5,462,531; 5,466,223; 5,468,227; 5,474,687; 5,478,314; 5,478,316; 5,478,328; 5,480,385; 5,480,387; 5,480,390; 5,482,039; 5,484,414; 5,486,163; 5,486,164; 5,487,732; 5,487,733; 5,487,734; 5,489,272; 5,492,536; 5,496,278; 5,501,672; 5,512,048; 5,512,050; 5,514,097; 5,514,107; 5,520,639; 5,520,649; 5,522,797; 5,522,812; 5,527,283; 5,527,284; 5,527,307; 5,529,189; 5,531,691; 5,531,692; 5,531,694; 5,531,704; 5,531,706; 5,533,975; 5,533,984; 5,536,243; 5,536,253; 5,536,257; 5,538,506; 5,538,508; 5,540,664; 5,540,666; 5,542,920; 5,542,927; 5,549,558; 5,549,568; 5,549,570; 5,549,572; 5,549,708; 5,558,648; 5,562,623; 5,562,624; 5,562,626; 5,562,631; 5,569,202; 5,569,203; 5,573,513; 5,575,770; 5,578,011; 5,578,014; 5,578,015; 5,582,591; 5,586,976; 5,591,133; 5,591,134; 5,591,138; 5,593,387; 5,593,390; 5,599,309; 5,599,313; 5,599,316; 5,599,318; 5,601,532; 5,601,535; 5,605,544; 5,609,577; 5,611,781; 5,611,782; 5,613,500; 5,613,951; 5,613,952; 5,615,771; 5,616,123; 5,616,132; 5,616,134; 5,616,135; 5,620,422; 5,620,425; 5,624,401; 5,624,405; 5,628,765; 5,630,803; 5,632,730; 5,632,733; 5,634,906; 5,634,909; 5,634,937; 5,637,092; 5,637,094; 5,643,220; 5,643,222; 5,647,851; 5,649,622; 5,651,774; 5,653,687; 5,653,688; 5,653,693; 5,656,031; 5,658,256; 5,658,257; 5,658,258; 5,658,259; 5,662,610; 5,662,617; 5,665,071; 5,665,075; 5,669,889; 5,672,155; 5,672,161; 5,681,291; 5,681,295; 5,688,240; 5,688,251; 5,693,016; 5,693,022; 5,693,023; 5,695,472; 5,704,911; 5,704,921; 5,707,393; 5,709,662; 5,709,667; 5,709,668; 5,713,866; 5,713,871; 5,713,872; 5,720,727; 5,725,498; 5,738,655; 5,741,223; 5,743,879; 5,743,887; 5,743,888; 5,743,891; 5,746,718; 5,749,854; 5,749,860; 5,755,692; 5,769,822; 5,769,827; 5,779,675; 5,779,677; 5,779,684; 5,788,677; 5,788,713; 5,792,107;

5,792,121; 5,792,122; 5,795,336; 5,797,885; 5,800,403;
5,807,334; 5,807,345; 5,807,352; 5,810,775; 5,810,784;
5,817,054; 5,817,070; 5,820,602; 5,823,997; 5,823,998;
5,827,293; 5,830,130; 5,836,911; 5,836,920; 5,843,036;
5,843,047; 5,848,990; 5,851,197; 5,853,390; 5,853,393;
5,855,839; 5,858,000; 5,865,227; 5,865,804; 5,868,711;
5,879,337; 5,882,342; 5,885,257; 5,891,052; 5,891,092;
5,891,097; 5,891,105; 5,897,508; 5,899,885; 5,899,886;
5,908,404; 5,908,408; 5,910,131; 5,911,706; 5,919,166;
5,921,959; 5,921,960; 5,921,961; 5,921,963; 5,921,964;
5,925,019; 5,928,188; 5,928,194; 5,928,205; 5,931,813;
5,938,638; 5,938,639; 5,941,850; 5,944,692; 5,944,693;
5,951,522; 5,954,699; 5,957,892; 5,957,895; 5,957,897;
5,960,797; 5,961,491; 5,971,953; 5,976,111; 5,980,487;
5,980,488; 5,980,491; 5,980,494; 5,984,899; 5,984,900;
5,989,219; 5,989,221; 5,993,417; 5,993,418; 5,997,500;
5,997,511; 5,997,513; 6,001,080; 6,007,474; 6,010,486;
6,010,487; 6,015,396; 6,015,438; 6,017,325; 6,022,337;
6,033,386; 6,033,387; 6,036,674; 6,039,713; 6,050,974;
6,050,977; 6,056,716; 6,056,724; 6,056,734; 6,063,040;
6,063,053; 6,066,115; 6,068,616; 6,074,360; 6,074,369;
6,074,370; 6,077,245; 6,080,135; 6,083,199; 6,083,200;
6,086,562; 6,086,569; 6,090,077; 6,090,078; 6,090,080;
6,093,172; 6,099,500; 6,099,503; 6,099,504; 6,102,844;
6,113,574; 6,117,112; 6,117,113; 6,126,637; 6,129,710;
6,142,972; 6,149,626; 6,149,629; 6,156,008; 6,156,010;
6,156,013; 6,156,015; 6,159,161; 6,159,181; 6,159,185;
6,171,284; 6,179,812; 6,183,444; 6,183,446; 6,186,980;
6,192,891; 6,193,695; 6,206,856; 6,206,857; 6,210,369;
6,217,550; 6,217,559; 6,221,044; 6,221,051; 6,221,052;
6,224,576; 6,228,054; 6,228,055; 6,235,006; 6,238,372;
6,241,707; 6,241,708; 6,254,575; 6,254,580; 6,258,056;
6,261,264; 6,261,265; 6,267,748; 6,270,472; 6,270,481;
6,273,870; 6,280,399; 6,280,420; 6,280,421; 6,283,941;
6,293,925; 6,299,601; 6,309,374; 6,309,375; 6,312,409;
6,315,113; 6,319,233; 6,319,234; 6,322,536; 6,325,781;
6,325,789; 6,331,173; 6,332,875; 6,344,031; 6,356,783;
6,358,236; 6,361,525; 6,364.865; 6,368,303; 6,371,938;
6,379,336; 6,379,340; 6,387,078; 6,402,716; 6,409,701;
6,409,703; 6,409,706; 6,412,490; 6,413,236; 6,413,237;
6,416,323; 6,416,497; 6,419,658; 6,428,463; 6,428,517;
6,432,035; 6,432,082; 6,432,087; 6,436,068; 6,440,098;
6,443,929; 6,447,480; 6,454,743; 6,458,105; 6,461,331;
6,461,333; 6,468,247; 6,474,375; 6,475,194; 6,478,771;
6,478,780; 6,482,176; 6,485,469; 6,485,474; 6,494,863;
6,500,155; 6,508,755; 6,511,454; 6,514,230; 6,517,516;
6,517,517; 6,524,278; 6,527,734; 6,527,742; 6,530,896;
6,530,904; 6,537,249; 6,537,252; 6,544,234; 6,547,764;
6,551,275; 6,551,276; 6,551,278; 6,551,299; 6,554,798;
6,558,351; 6,558,357; 6,558,365; 6,565,533; 6,565,538;
6,569,115; 6,572,584; 6,572,585; 6,575,939; 6,579,256;
6,582,405; 6,584,910; 6,585,690; 6,585,693; 6,585,702;
6,589,158; 6,592,508; 6,592,555; 6,592,556; 6,595,962;
6,599,268; 6,599,269; 6,599,272; 6,605,058; 6,605,067;
6,605.073; 6,607,508; 6,607,509; 6,613,019; 6,613,022;
6,616,630; 6,616,638; 6,616,639; 6,620,136; 6,620,137;
6,620,138; 6,623,455; 6,623,458; 6,623,459; 6,626,309;
6,626,864; 6,629,957; 6,629,959; 6,632,198; 6,637,587;
6,638,248; 6,638,255; 6,641,561; 6,645,181; 6,652,482;
6,656,164; 6,659,975; 6,659,982; 6,663,593; 6,669,666;
6,673,034; 6,673,044; 6,673,049; 6,678,550; 6,679,863;
6,679,864; 6,685,676; 6,685,677; 6,689,091; 6,689,106;
6,689,107; 6,689,108; 6,692,470; 6,692,471; 6,699,218;
6,702,784; 6,706,011; 6,706,015; 6,706,019; 6,709,416;
6,712,787; 6,712,788; 6,716,191; 6,716,197; 6,716,198;
6,719,721; 6,719,728; 6,719,730; 6,723,068; 6,723,072;
6,726,655; 6,726,658; 6,726,661; 6,726,662; 6,730,059;
6,736,800; 6,740,059; 6,743,203; 6,749,833; 6,752,782;
6,752,784; 6,752,798; 6,761,706; 6,767,336; RE 33,585; RE
34,335; RE 34,936; RE 36,398; RE 36,447; RE 37,110; RE
37,252; RE 37,487; US2002/0123719; US2002/0123736;
US2003/0023203; US2003/0036725; US2003/0109827; and
US2003/0125671.

SUMMARY OF THE INVENTION

The present invention seeks to provide an improved medicinal container engagement and automatic needle device. There is thus provided in accordance with a preferred embodiment of the present invention a medicinal container engagement and automatic needle device including an automatic needle assembly and a medicinal container receptacle removably joined to the automatic needle assembly.

In accordance with a preferred embodiment of the present invention the medicinal container engagement and automatic needle device also includes a break-away connection joining the automatic needle assembly to the medicinal container receptacle. Preferably, the medicinal container engagement and automatic needle device also includes first and second syringe adapter elements respectively engaging the automatic needle assembly and the medicinal container receptacle.

In accordance with another preferred embodiment of the present invention the first and second syringe adapter elements are located in a side by side mutual orientation. Alternatively, the first and second syringe adapter elements are located in a parallel mutual orientation. Preferably, the break-away connection includes a safety element which prevents actuation of the automatic needle assembly while the medicinal container receptacle is joined to the automatic needle assembly.

In accordance with yet another preferred embodiment of the present invention the medicinal container engagement and automatic needle device also includes a safety element which prevents actuation of the automatic needle assembly while the medicinal container receptacle is joined to the automatic needle assembly.

There is also provided in accordance with another preferred embodiment of the present invention a medicinal container engagement and automatic needle device including an automatic needle assembly and a medicinal container engagement operated communication controller having at least two operative states and providing selectable fluid communication between either of the automatic needle assembly and a medicinal container and an additional vessel.

In accordance with a preferred embodiment of the present invention the medicinal container engagement and automatic needle device also includes a medicinal container receptacle joined to the automatic needle assembly. Preferably, a sealing element of the medicinal container is punctured prior to a position change of the medicinal container engagement operated communication controller.

In accordance with another preferred embodiment of the present invention insertion of the medicinal container results in fluid communication between the medicinal container and the additional vessel. Preferably, removal of the medicinal container results in fluid communication between the automatic needle device and the additional vessel.

In accordance with a further preferred embodiment of the present invention the automatic needle assembly includes a housing element, at least one resilient element arranged to be located within the housing element, at least one needle bearing element adapted, when actuated, to be displaced by the at least one resilient element with respect to the housing element from a non-penetration position to a penetration position and a needle guard adapted for positioning with respect to the housing element and wherein displacement of the needle guard is operative to actuate displacement of the at least one needle bearing element from the non-penetration position to the penetration position. Preferably, rearward displacement of the needle guard is operative to actuate displacement of the at least one needle bearing element from the non-penetration position to the penetration position.

In accordance with a still further preferred embodiment of the present invention the automatic needle assembly also includes a safety element adapted to prevent inadvertent actuation of displacement of the at least one needle bearing element. Preferably, the safety element prevents inadvertent rearward displacement of the needle guard. Additionally or alternatively the at least one resilient element includes a unitary resilient element. Alternatively, the at least one resilient element includes first and second coil springs.

In accordance with yet a further preferred embodiment of the present invention the housing element includes an injection device engagement portion. Preferably, the housing element and the at least one needle bearing element together define a fluid pathway from the injection device engagement portion through the needle at least when the needle bearing element is in both the non-penetration position and the penetration position. Additionally or alternatively, the needle guard is displaceable by the at least one resilient element.

In accordance with an additional preferred embodiment of the present invention the at least one resilient element includes first and second compression springs which provide selectable forward displacement to the at least one needle bearing element. Preferably, the needle bearing element includes a hub portion and a needle adhered thereto and extending through a septum. Additionally or alternatively, the automatic needle assembly also includes a safety tab operative for disabling actuation of the automatic needle device. As a further alternative, the safety tab includes a spacer portion and a tab portion.

In accordance with another preferred embodiment of the present invention the automatic needle assembly includes a housing element, at least one needle bearing element adapted, when actuated, to be displaced with respect to the housing element from a non-penetration position to a penetration position and a needle guard adapted for positioning with respect to the at least one needle bearing element and with respect to the housing element in a mutually locked needle guarding orientation, whereby displacement of the needle guard in a first direction relative to the housing is prevented by engagement of the needle guard with the at least one needle bearing element and displacement of the needle guard in a second direction relative to the housing, opposite to the first direction, is prevented by engagement of the needle guard with the housing element.

In accordance with yet another preferred embodiment of the present invention the housing element is an integrally formed element having a generally cylindrical configuration and is generally side-to-side symmetric about a longitudinal axis. Preferably, the housing element includes a rearward generally tubular portion which terminates in an open back and defines forwardly thereof a generally cylindrical portion, whose outer configuration includes top and bottom grip regions. Additionally or alternatively, the housing element includes first and second forwardly and rearwardly tapered side protrusions.

In accordance with still another preferred embodiment of the present invention the automatic needle assembly includes at an inner surface of the generally cylindrical portion forward and rearward inwardly extending transverse ribs and a plurality of inwardly extending longitudinal slots. Preferably, the automatic needle assembly includes at an interior of a generally tubular portion thereof, a generally cylindrical bore which communicates via a tapered interface with a forward bore, disposed interiorly of a cylindrical portion, the cylindrical bore being arranged to receive a septum. Additionally or alternatively, the automatic needle assembly includes apertures which are formed in cylindrical walls of the cylindrical bore in alignment along a line extending transversely to a longitudinal axis of the housing element.

In accordance with a further preferred embodiment of the present invention and wherein a forward-facing back wall surface of the generally cylindrical portion defines a seat for the at least one resilient element. Preferably, the housing element is formed with a pair of side-to-side symmetric windows, to allow viewing of the tip of a needle held by the needle bearing element. Additionally or alternatively, the needle bearing element includes a needle hub and a needle. More preferably, the needle bearing element has a generally cylindrical configuration and is top-to-bottom and side-to-side symmetric about a longitudinal axis.

In accordance with a still further preferred embodiment of the present invention the needle bearing element defines a generally tubular body having formed thereon a pair of up-down mutually spaced, forwardly facing, outwardly extending hook protrusions. Preferably, the protrusions are each associated with a rearward facing rib. Additionally or alternatively, a rearwardly extending arm is formed at both a top and a bottom of the tubular body, each arm including, adjacent an extreme rearwardly facing end thereof, a tapered inwardly facing tooth and forwardly thereof an outwardly facing tooth, having a transversely extending rearwardly facing surface.

In accordance with yet a further preferred embodiment of the present invention the top and bottom pairs of outwardly facing ribs are formed on the tubular portion, adjacent respective rearward facing ribs, the outwardly facing ribs being operative to slidably locate the needle bearing element within the needle guard. Preferably, the tubular body defines a generally open back and a forward facing wall portion adjacent in which is formed a recess, which communicates with a narrow axial bore, arranged to receive the needle, which extends therethrough. Additionally or alternatively, a rearward facing external wall portion, located at a rearward end of the tubular body, defines a seat for the at least one resilient element.

In accordance with an additional preferred embodiment of the present invention the needle guard has a generally cylindrical configuration and is top-to-bottom and side-to-side symmetric about a longitudinal axis. Preferably, the needle guard defines a generally tubular body having formed thereon a plurality of circumferentially spaced, longitudinally extending, outward facing ribs, having rearward facing ends, the outward facing ribs being adapted to slidably locate the needle guard within inwardly extending longitudinal slots of the housing element. Additionally or alternatively, extending rearwardly of the outwardly facing ribs there is provided a curved rearward facing portion having a pair of inwardly facing slots formed therein, and, extending rearwardly of the ribs, there is formed a symmetrically curved rearward facing portion having a pair of ribs formed therein.

In accordance with another preferred embodiment of the present invention the curved rearward facing portions together with the rearward facing ends define a seat for a spring forming part of the at least one resilient element. Preferably, the inwardly facing slots are operative to slidably locate the needle bearing element within the needle guard, by allowing the outwardly facing ribs to slide therein. Additionally or alternatively, a rearwardly extending arm is formed at each side of the tubular body, each of the arms including adjacent an extreme rearwardly facing end thereof, an outwardly facing tooth, having an inclined forward surface and a transversely extending rearwardly facing surface.

In accordance with yet another preferred embodiment of the present invention the tubular body defines a generally open back and a forward facing wall portion, defining an injection site engagement surface. Preferably, the injection site engagement surface includes a pair of mutually concentric circles of mutually spaced forwardly extending protrusions and the forward facing wall portion is formed with an axial bore, arranged to allow a needle to extend therethrough. Additionally or alternatively, the needle guard is formed with a pair of side-to-side symmetric windows, to allow viewing of the tip of a needle.

In accordance with still another preferred embodiment of the present invention in a pre-use operative orientation suitable for storage, the housing element is joined to the needle bearing element by snap fit engagement of inner facing teeth formed on the needle bearing element into apertures formed in cylindrical walls of the housing element. Preferably, the at least one resilient element includes first and second compression springs, the first compression spring being maintained under compression between forward-facing back wall surface of a generally cylindrical portion of the housing element and a rearward facing wall portion of the needle bearing element and the second compression spring being maintained under compression between the forward facing back wall surface and rearward facing ends of the needle guard, which is slidably retained against disassembly forward movement by the positioning of curved rearward facing portions thereof immediately rearward of the inner facing teeth of the needle bearing element. Additionally or alternatively, the needle bearing element is retained in its place by engagement of rearwardly outwardly facing surfaces of the inner facing teeth with curved rearward facing portions of the needle guard, thus preventing rearwardly extending arms of the needle bearing element from bending outwardly and releasing the snap fit engagement of the inner facing teeth and apertures formed in the cylindrical walls of the cylindrical bore of the housing element.

In accordance with a further preferred embodiment of the present invention and wherein due to engagement of the needle guard with an injection site on a body, the needle guard is forced, against the urging of the at least one resilient element, to move axially in a rearward direction with respect to the remainder of the automatic needle device, thus sliding the curved rearward facing portions thereof further rearward of the outwardly facing teeth of the needle bearing element, thus allowing the arms of the needle bearing element to cantilever outwardly. Additionally or alternatively, and wherein at all times the needle sealingly and slidably engages a septum.

BRIEF DESCRIPTION OF THE DRAWINGS

The present invention will be understood and appreciated more fully from the following detailed description, taken in conjunction with the drawings in which:

FIGS. 7A and 7B are respective top and side view simplified planar illustrations of the needle hub assembly of FIGS. 6A and 6B;

FIGS. 8A and 8B are sectional illustrations taken along respective section lines and directions VIIIA-VIIIA and VIIIB-VIIIB in FIGS. 7A and 7B;

FIGS. 11A and 11B are respective top and side view simplified planar illustrations of the needle guard element of FIGS. 10A and 10B;

FIGS. 12A and 12B are sectional illustrations taken along respective section lines and directions XIIA-XIIA and XIIB-XIIB in FIGS. 11A and 11B;

FIGS. 14A, 14B, 14C, 14D, 14E, 14F, 14G, 14H and 14I are simplified pictorial illustration of various stages of typical use of the medicinal container engagement and automatic needle device of FIG. 1;

FIGS. 19A and 19B are respective top and side view simplified planar illustrations of the medicinal container engagement and automatic needle device of FIG. 18;

FIG. 20 is a sectional illustration taken along section lines XX-XX in FIG. 19B;

FIGS. 22A and 22B are respective top and side view simplified planar illustrations of the medicinal container engagement and automatic needle device of FIG. 21;

FIG. 23 is a sectional illustration taken along section lines XXIII-XXIII in FIG. 22B;

FIG. 24 is a simplified assembled view illustration of the medicinal container engagement and automatic needle device of FIGS. 1 and 14E in a syringe-needle housing element engagement operative orientation;

FIGS. 25A and 25B are respective top and side view simplified planar illustrations of the medicinal container engagement and automatic needle device of FIG. 24;

FIG. 26 is a sectional illustration taken along section lines XXVI-XXVI in FIG. 25B;

FIGS. 28A and 28B are respective top and side view simplified planar illustrations of the medicinal container engagement and automatic needle device of FIG. 27;

FIGS. 29A and 29B are sectional illustrations taken along respective section lines XXIXA-XXIXA and XXIXB-XXIXB in FIGS. 28A and 28B.

FIG. 30 is a simplified pictorial illustration of the medicinal container engagement and automatic needle device of FIGS. 1 and 14G in an injection site engagement operative orientation;

FIGS. 31A and 31B are respective top and side view simplified planar illustrations of the medicinal container engagement and automatic needle device of FIG. 31;

FIGS. 32A and 32B are sectional illustrations taken along respective section lines XXXIIA-XXXIIA and XXXIIB-XXXIIB in FIGS. 31A and 31B;

FIGS. 34A and 34B are respective top and side view simplified planar illustrations of the medicinal container engagement and automatic needle device of FIG. 33;

FIGS. 35A and 35B are sectional illustrations taken along respective section lines XXXVA-XXXVA and XXXVB-XXXVB in FIGS. 34A and 34B;

FIG. 36 is a simplified pictorial illustration of the medicinal container engagement and automatic needle device of FIGS. 1 and 14I in a post-drug delivery, needle guarded operative orientation;

FIGS. 37A and 37B are respective top and side view simplified planar illustrations of the medicinal container engagement and automatic needle device of FIG. 36;

FIGS. 38A and 38B are sectional illustrations taken along respective section lines XXXVIIIA-XXXVIIIA and XXXVIIIB-XXXVIIIB in FIGS. 37A and 37B;

FIG. 50 is a simplified top view planar illustration of the medicinal container engagement and automatic needle device of FIG. 49;

FIG. 51 is a sectional illustration taken along section lines LI-LI in FIG. 50;

FIG. 56 is simplified top view planar illustration of the medicinal container engagement and automatic needle device of FIG. 55;

FIG. 57 is a sectional illustration taken along section lines LVII-LVII in FIG. 56;

FIG. 59 is a simplified top view planar illustration of the medicinal container engagement and automatic needle device of FIG. 58; and FIG. 60 is a sectional illustration taken along section lines LX-LX in FIG. 59.

DETAILED DESCRIPTION OF PREFERRED EMBODIMENTS

Figure 1:
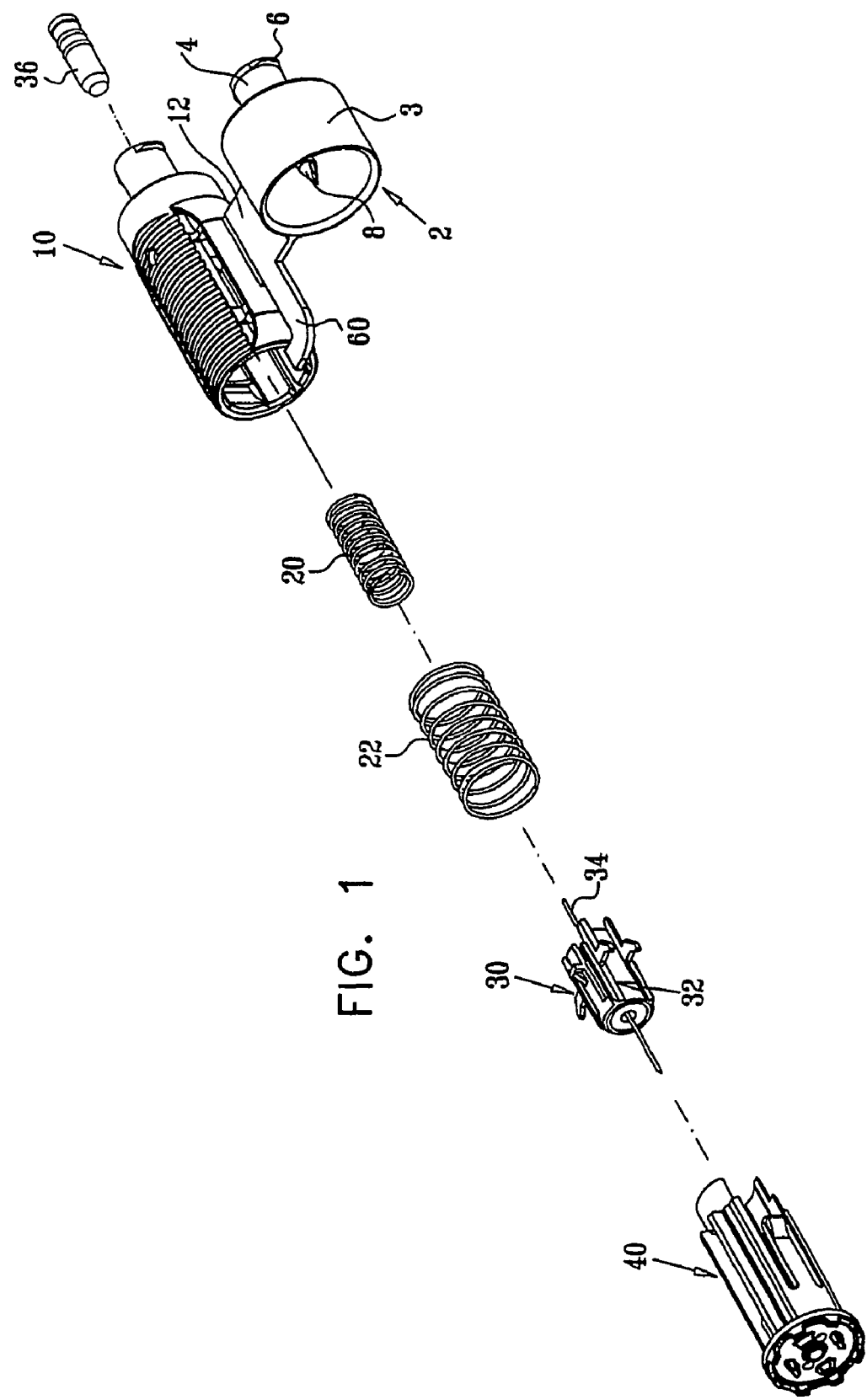
FIG. 1 is a simplified exploded view illustration of a medicinal container engagement and automatic needle device constructed and operative in accordance with a preferred embodiment of the present invention.

Reference is now made to FIG. 1 is a simplified exploded view illustration of a medicinal container engagement and automatic needle device constructed and operative in accordance with a preferred embodiment of the present invention.

As seen with particular clarity in FIG. 1, the medicinal container engagement and automatic needle device comprises a vial adapter element 2 including a vial port 3 integrally formed with a syringe adapter portion 4 preferably having luer lock protrusions 6. The syringe adapter portion 4 is in fluid communication with a spike 8 which lies within vial port 3. The vial adapter element 2 is removably joined to a needle housing element 10 preferably by means of an integrally formed break-away connection 12, which is configured to cleanly break away from needle housing element 10, preferably without leaving burrs or other protrusions.

Disposed within needle housing element 10 are generally coaxially seated respective first and second compression springs 20 and 22, which provide selectable forward displacement to a needle hub assembly 30, which includes a hub portion 32 and a needle 34 adhesively adhered thereto and extending rearwardly through a septum 36, and to a needle guard element 40. Alternatively, needle hub portion 32 may be injected onto the needle, by a method such as insert molding.

A safety tab 60 is preferably integrally formed with breakaway connection 12, thus disabling actuation of the automatic needle functionality of the medicinal container engagement and automatic needle device until the vial adapter element 2 and break away connection 12 are removed, as described hereinbelow.

It will be appreciated by persons skilled in the art that safety tab 60 may be designed in many different shapes, such as a portion which is inserted into a slot between the needle guard element 40 and the needle housing element 10, as a stand alone injection molded part, or as an integral part of any suitable part of the medicinal container engagement and automatic needle device such as the needle guard element 40 or the needle hub 32.

It will additionally be appreciated by those skilled in the art that compression springs 20 and 22 may be replaced with other suitable types of resilient elements such as tension springs, elastomeric compression springs or plastic springs which may be integrated into needle housing element 10, into needle hub portion 32 or into needle guard element 40.

Figure 2A:
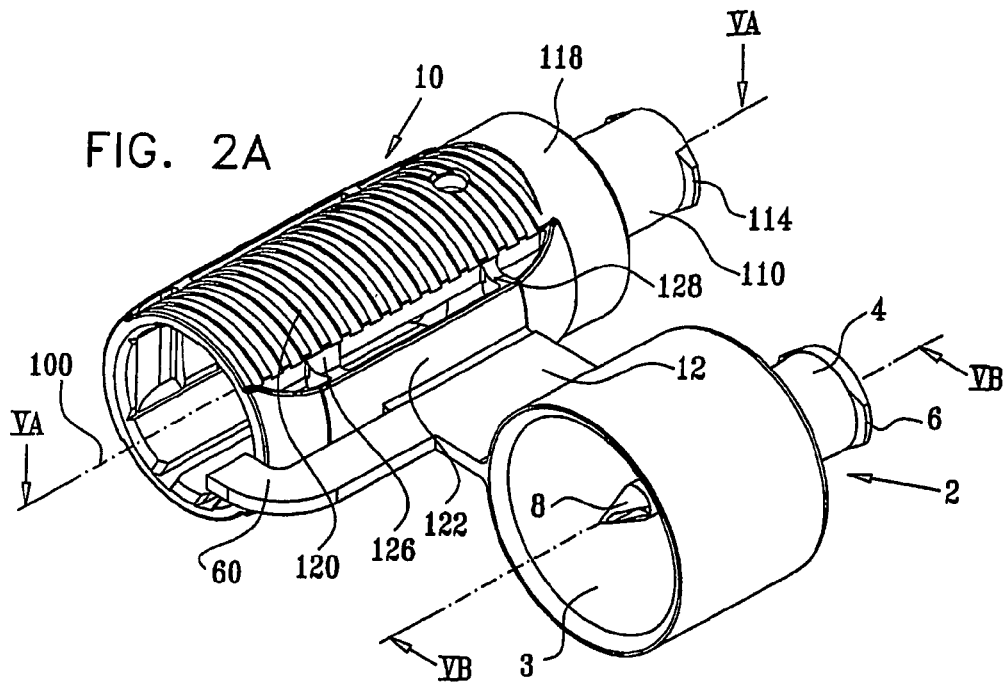
FIGS. 2A and 2B are simplified pictorial illustrations of a housing element which forms part of the medicinal container engagement and automatic needle device of FIG. 1.
Figure 2B:
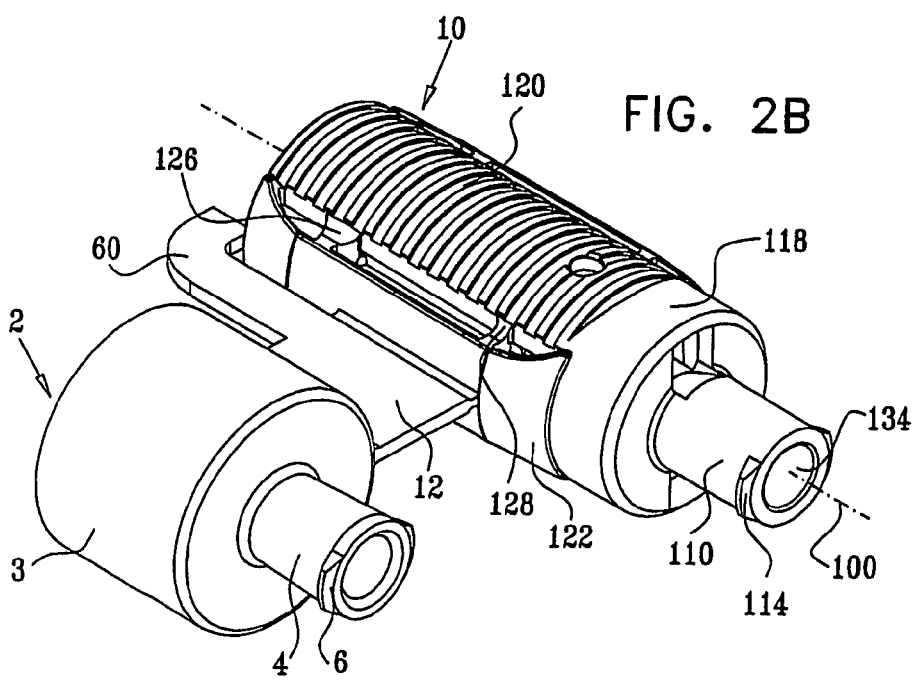
Figure 3A:
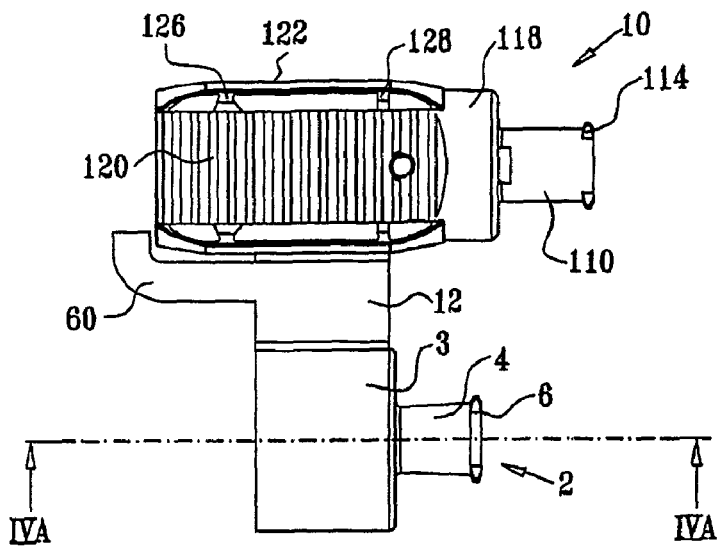
FIGS. 3A and 3B are respective top and side view simplified planar illustrations of the housing element of FIGS. 2A and 2B.
Figure 3B:
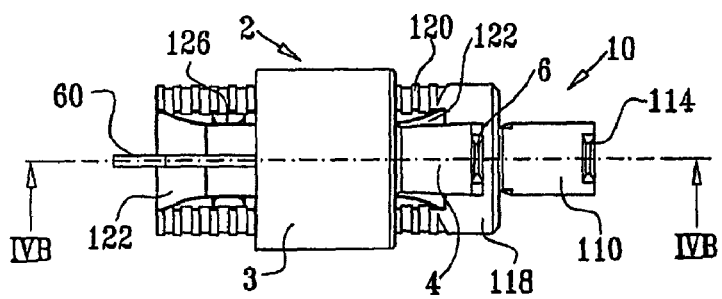
Figure 4A:
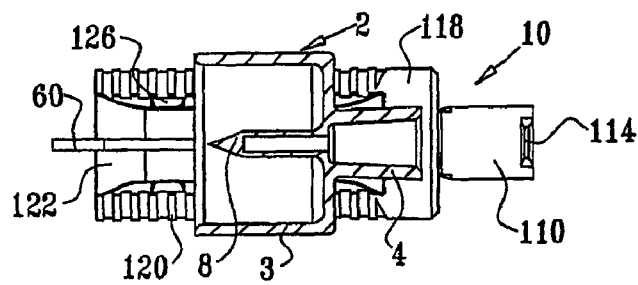
FIGS. 4A, 4B are sectional illustrations taken along respective section lines and directions IVA-IVA and IVB-IVB in FIGS. 3A and 3B.
Figure 4B:
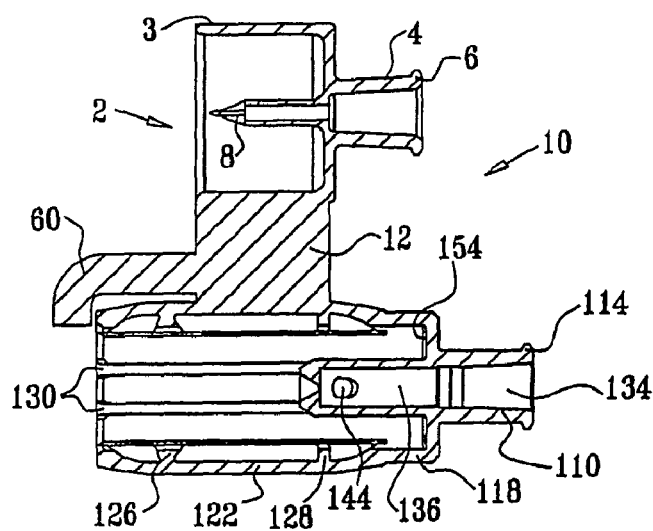
Figure 5A:
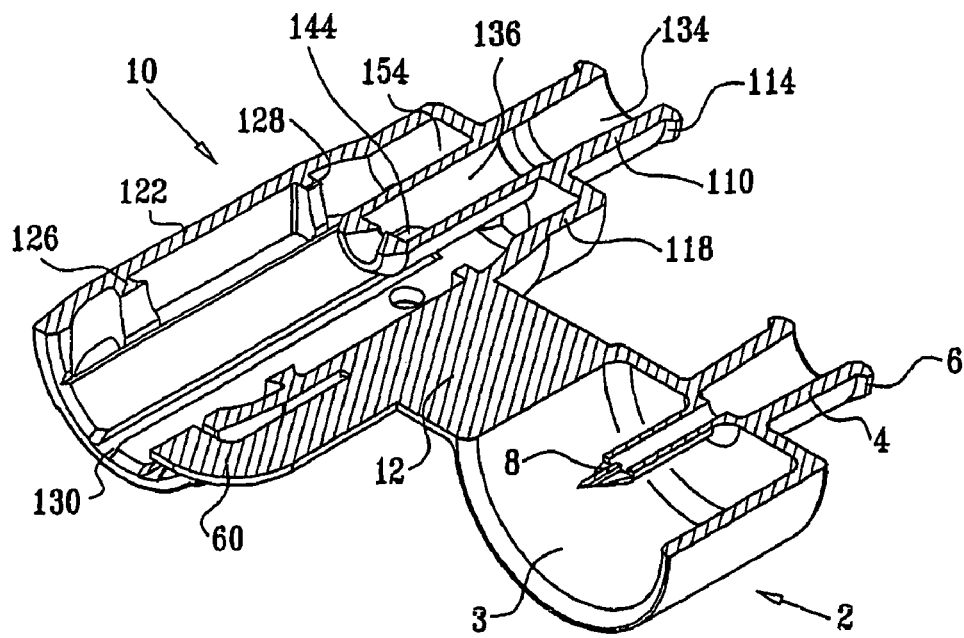
FIGS. 5A and 5B are pictorial sectional illustrations taken along respective section lines and directions VA-VA and VB-VB in FIG. 2A.
Figure 5B:
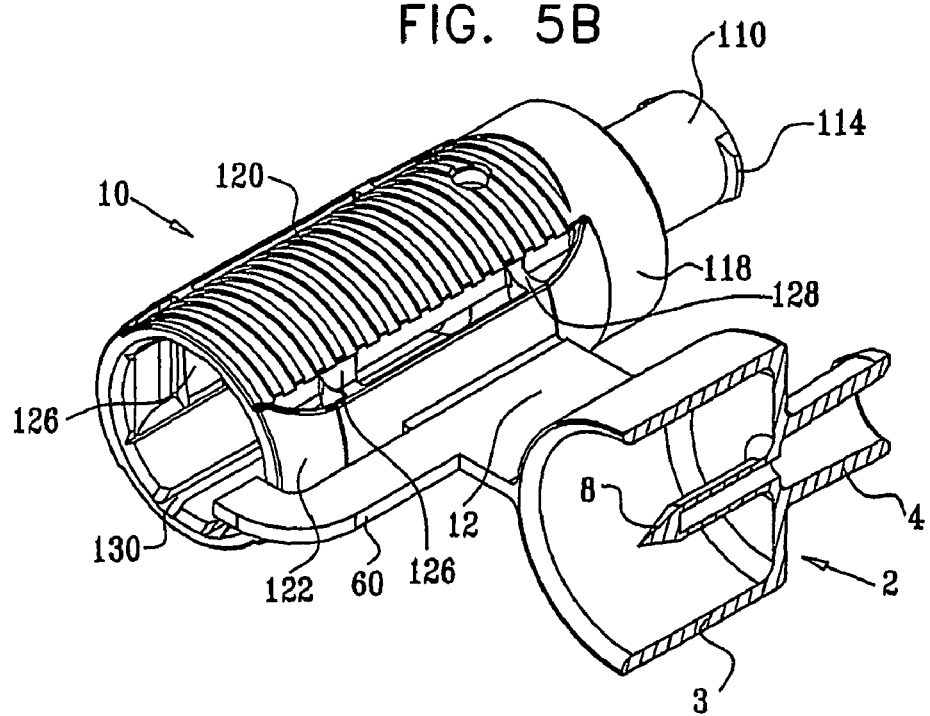

Reference is now made to FIGS. 2A and 2B, which are simplified pictorial illustrations of a preferred needle housing element 10 which forms part of the medicinal container engagement and automatic needle device of FIG. 1, to FIGS. 3A and 3B are respective top and side view simplified planar illustrations thereof, to FIGS. 4A and 4B which are sectional illustrations taken along respective section lines and directions IVA-IVA and IVB-IVB in FIGS. 3A and 3B and to FIGS. 5A and 5B which are pictorial sectional illustrations taken along respective section lines and directions VA-VA and VB-VB in FIG. 2A.

As seen in FIGS. 2A-5B, the needle housing element 10 preferably is an integrally formed element, preferably injection molded of plastic. Needle housing element 10 preferably has a generally cylindrical configuration and is preferably top-to-bottom and side-to-side symmetric about a longitudinal axis 100.

Needle housing element 10 preferably includes a rearward generally tubular portion 110, which terminates in an open back and defines generally symmetric side-facing tabs 114. Forward of rearward generally tubular portion 110 there is provided a generally cylindrical portion 118, whose outer configuration preferably includes top and bottom grip regions 120, which are ribbed in a direction transverse to longitudinal axis 100 and first and second forwardly and rearwardly tapered side protrusions 122.

As described above with reference to FIG. 1, there is provided a vial adapter element 2 including a vial port 3 integrally formed with a syringe adapter portion 4 preferably having luer lock protrusions 6. The syringe adapter portion 4 is in fluid communication with a spike 8 which lies within vial port 3. The vial adapter element 2 is removably joined to one of the first and second forwardly and rearwardly tapered side protrusions 122 of needle housing element 10 preferably by means of an integrally formed break-away connection 12, which is configured to cleanly break away from side protrusion 122 of needle housing element 10, preferably without leaving burrs or other protrusions.

At an inner surface of generally cylindrical portion 118 there are provided forward and rearward inwardly extending transverse ribs 126 and 128 and a plurality of inwardly extending longitudinal slots 130. The interior of tubular portion 110 defines a generally cylindrical bore 134. Bore 134 communicates via a tapered interface with a forward bore 136, disposed interiorly of cylindrical portion 118, which is arranged to receive septum 36. Bore 136 has a circular cross section which is slightly smaller than that of bore 134.

Apertures 144 are formed in the cylindrical walls of bore 136 in alignment along a line extending transversely to longitudinal axis 100. A forward-facing back wall surface 154 of generally cylindrical portion 118 defines a spring seat for springs 20 and 22.

The needle housing element 10 may optionally be formed with a pair of side-to-side symmetric windows, to allow viewing of the tip of the needle 34, for example, when purging air bubbles from syringe 502. Alternatively, needle housing element 10 may be formed of a transparent material.

Figure 6A:
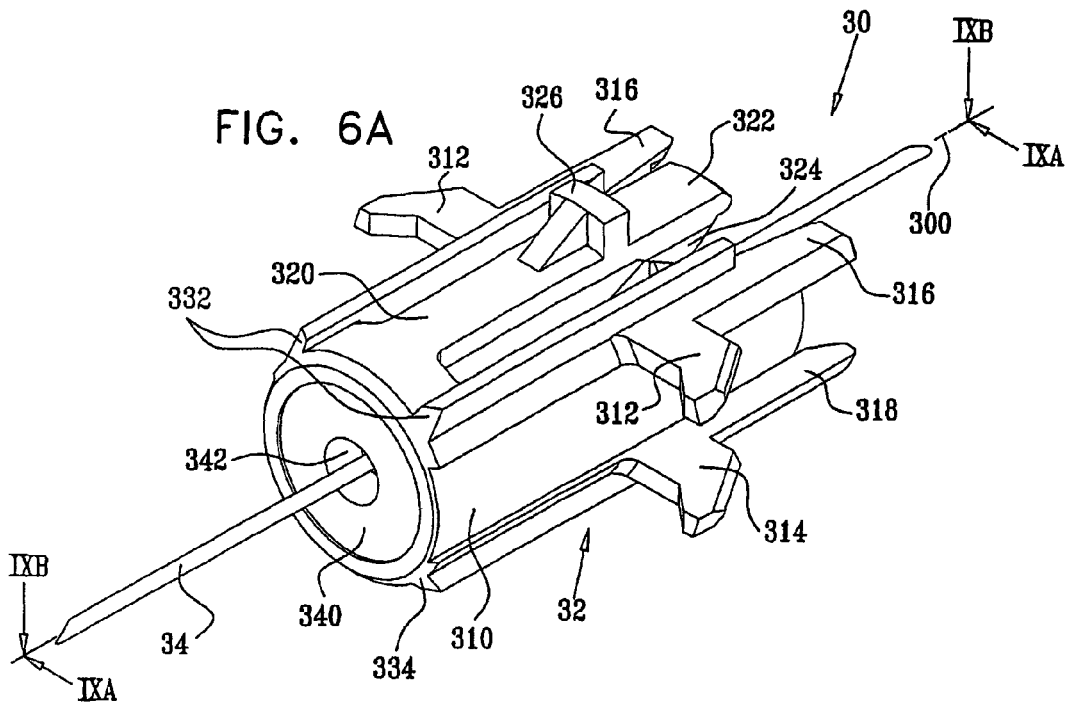
FIGS. 6A and 6B are simplified pictorial illustrations of a needle hub assembly which forms part of the medicinal container engagement and automatic needle device of FIG. 1.
Figure 6B:
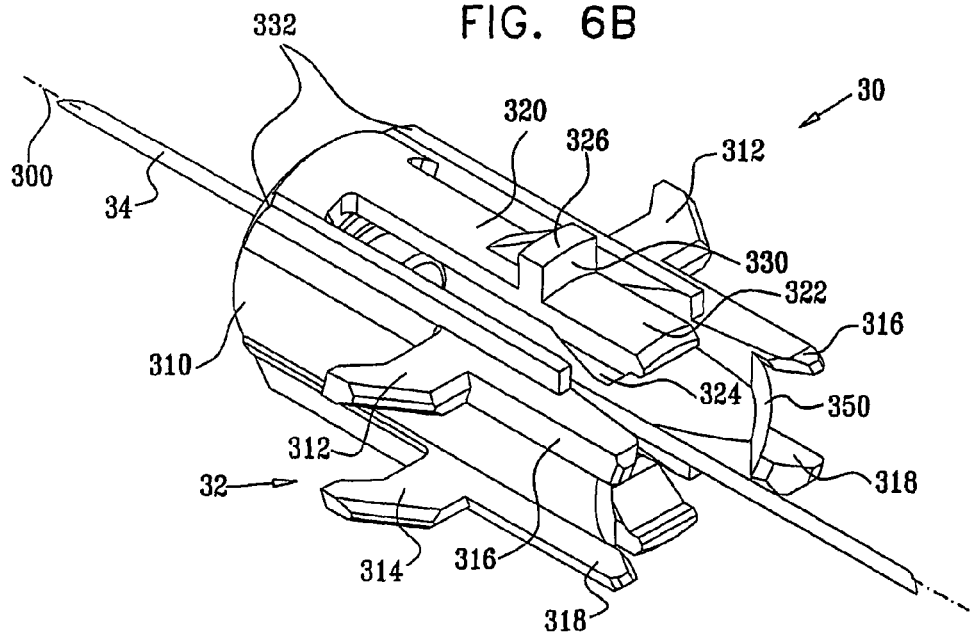
Figure 9A:
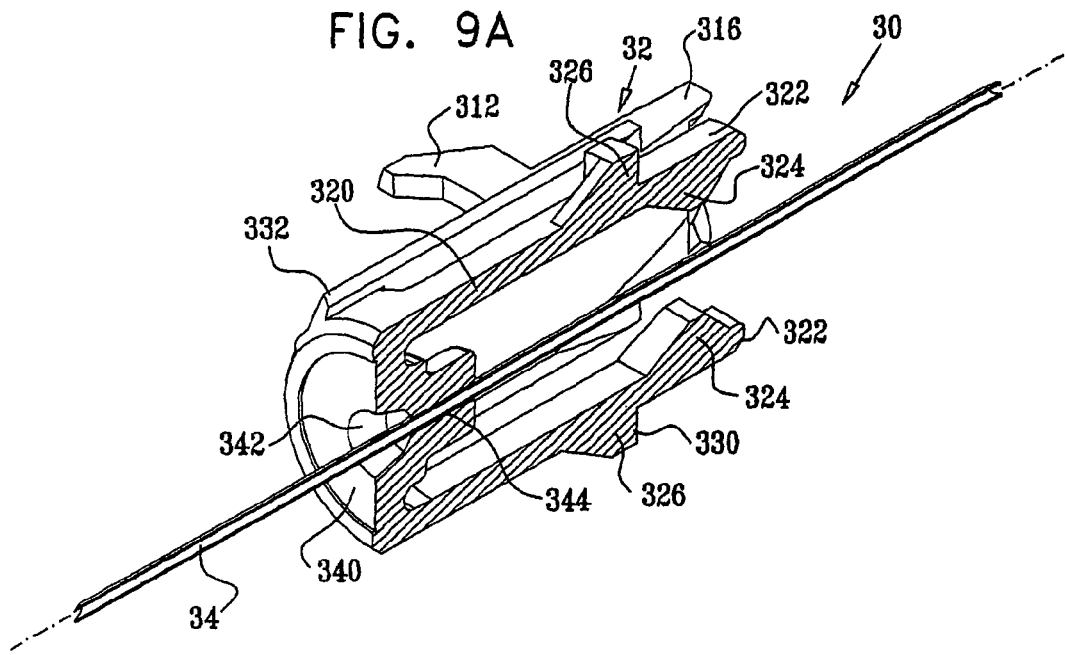
FIGS. 9A and 9B are pictorial sectional illustrations taken along respective section lines and directions IXA-IXA and IXB-IXB in FIG. 6A.
Figure 9B:
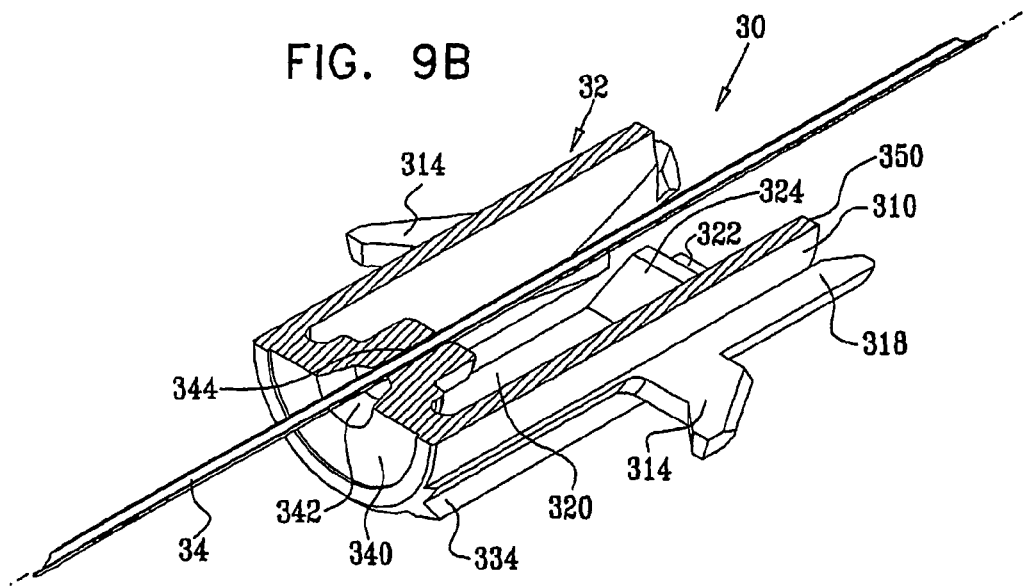

Reference is now made to FIGS. 6A and 6B, which are simplified pictorial illustrations of a needle hub assembly 30 which forms part of the medicinal container engagement and automatic needle device of FIG. 1, to FIGS. 7A and 7B, which are respective top and side view simplified planar illustrations of the needle hub assembly of FIGS. 6A and 6B, to FIGS. 5A and 8B, which are sectional illustrations taken along respective section lines and directions VIIIA-VIIIA and VIIIB-VIIIB in FIGS. 7A and 7B and to FIGS. 9A and 9B, which are pictorial sectional illustrations taken along respective section lines and directions IXA-IXA and IXB-IXB in FIG. 6A.

As seen in FIGS. 6A-9B, the needle hub assembly 30 preferably comprises a needle hub 32, which is an integrally formed element, preferably injection molded of plastic, and a needle 34. Needle hub assembly 30 preferably has a generally cylindrical configuration and is preferably top-to-bottom and side-to-side symmetric about a longitudinal axis 300, which, when assembled together with needle housing element 10, is coaxial with longitudinal axis 100 (FIGS. 2A-5B).

Needle hub assembly 30 preferably defines a generally tubular body 310. A pair of up-down mutually spaced, forwardly facing, outwardly extending hook protrusions 312 and 314 is formed on each side of tubular portion 310. Protrusions 312 and 314 are each associated with a rearward facing rib, here designated 316 and 318 respectively.

A rearwardly extending arm 320 is formed at both the top and the bottom of tubular body 310. Each arm includes, adjacent an extreme rearwardly facing end 322 thereof, a tapered inwardly facing tooth 324 and forwardly thereof an outwardly facing tooth 326, having a transversely extending rearwardly facing surface 330.

Top and bottom pairs of outwardly facing ribs 332 and 334 are preferably formed on tubular portion 310, adjacent rearward facing ribs 316 and 318 respectively. Outwardly facing ribs 332 and 334 are operative to slidably locate needle hub assembly 30 within needle guard element 40. Tubular body 310 defines a generally open back and a forward facing wall portion 340 adjacent in which is formed a recess 342, which communicates with a narrow axial bore 344, arranged to receive needle 34, which extends therethrough and is held in place, preferably by an adhesive, which is located in recess 342. A rearward facing external wall portion 350, located at the rearward end of tubular body 310, defines a spring seat for spring 20, which is partially surrounded by rearward facing ends of ribs 316 and 318.

Figure 10A:
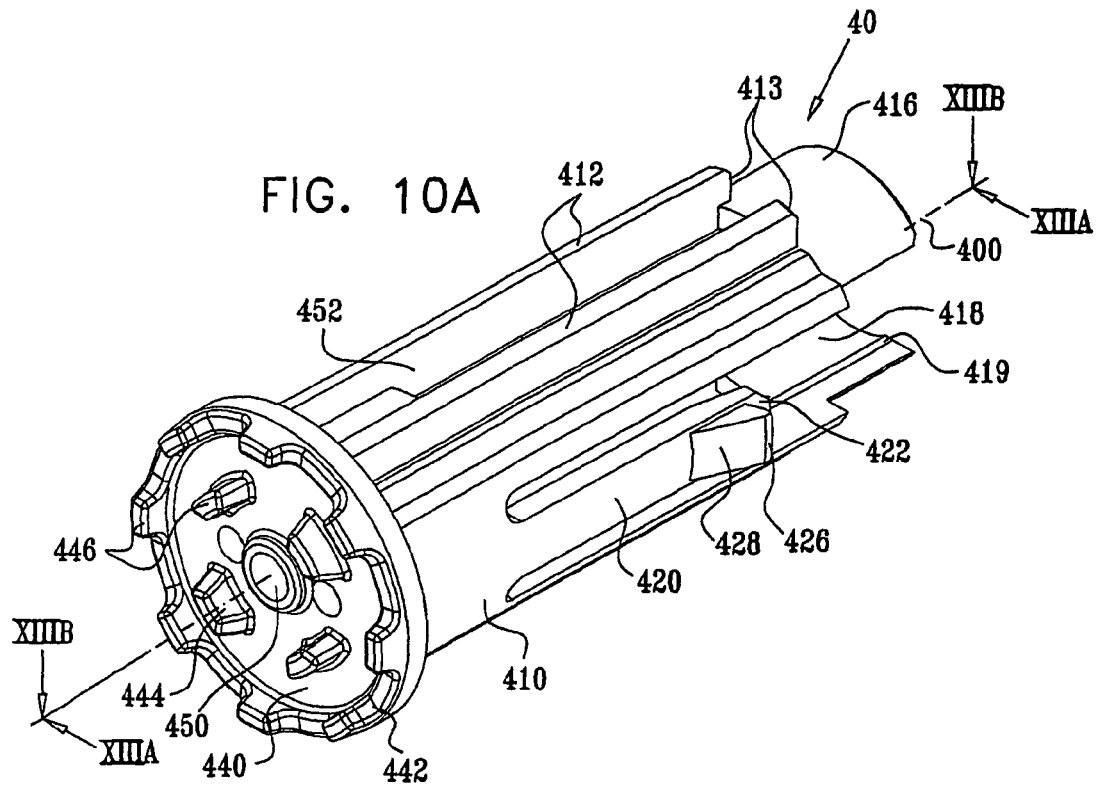
FIGS. 10A and 10B are simplified pictorial illustrations of a needle guard element which forms part of the medicinal container engagement and automatic needle device of FIG. 1.
Figure 10B:
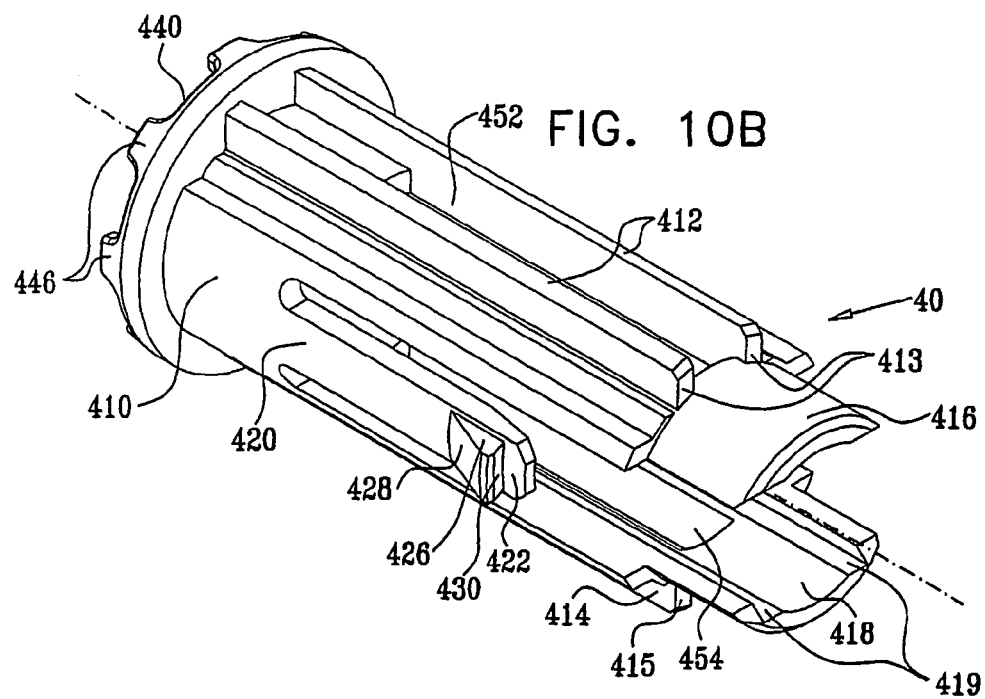

Reference is now made to FIGS. 10A and 10B, which are simplified pictorial illustrations of a needle guard element 40 which forms part of the medicinal container engagement and automatic needle device of FIG. 1, to FIGS. 11A and 11B, which are respective top and side view simplified planar illustrations of the needle guard element of FIGS. 10A and 10B, to FIGS. 12A and 12B, which are sectional illustrations taken along respective section lines and directions XIIA-XIIA and XIIB-XIIB in FIGS. 11A and 11B and to FIGS.

13A and 13B which are pictorial sectional illustrations taken along respective section lines and directions XIIIA-XIIIA and XIIIB-XIIIB in FIG. 10A.

As seen in FIGS. 10A-13B, the needle guard element 40 preferably is an integrally formed element, preferably injection molded of plastic. Needle guard 40 preferably has a generally cylindrical configuration and is preferably top-to-bottom and side-to-side symmetric about a longitudinal axis 400, which, when assembled together with needle housing element 10 and needle hub assembly 30 is coaxial with longitudinal axis 100 (FIGS. 2A-5B) and longitudinal axis 300 (FIGS. 6A-9B).

Needle guard element 40 preferably defines a generally tubular body 410. Four mutually circumferentially spaced, longitudinally extending, outward facing ribs 412 and 414, having rearward facing ends 413 and 415 respectively, are formed on both the top and the bottom of generally tubular body 410. Outward facing ribs 412 and 414 are adapted to slidably locate the needle guard element 40 within the inwardly extending longitudinal slots 130 of the needle housing element 10. Extending rearwardly of ribs 412 is a curved rearward facing portion 416 having a pair of slots 417 formed therein, and extending rearwardly of ribs 414 is a similar and symmetrically curved rearward facing portion 418 having a pair of slots 419 formed therein.

Curved rearward facing portions 416 and 418 together with rearward facing ends 413 and 415 define the seat for spring 22. Slots 417 and 419 are operative to slidably locate needle hub assembly 30 within needle guard element 40, by allowing outwardly facing ribs 332 and 334 to slide therein. A rearwardly extending arm 420 is formed at each side of tubular body 410. Each arm includes adjacent an extreme rearwardly facing end 422 thereof, an outwardly facing tooth 426, having an inclined forward surface 428 and a transversely extending rearwardly facing surface 430.

Tubular body 410 defines a generally open back and a forward facing wall portion 440, defining an injection site engagement surface characterized in that it has a pair of mutually concentric circles 442 and 444 of mutually spaced forwardly extending protrusions 446. Forward facing wall portion 440 is formed with an axial bore 450, arranged to allow needle 34 to extend therethrough.

Top and bottom windows 452 and 454 are defined between respective pairs of ribs 412 and 414.

The needle guard element 40 may optionally be formed with a pair of side-to-side symmetric windows, to allow viewing of the tip of the needle 34, for example when purging air bubbles from syringe 50. Alternatively, needle guard element 40 may be formed of a transparent material.

Figure 14C:
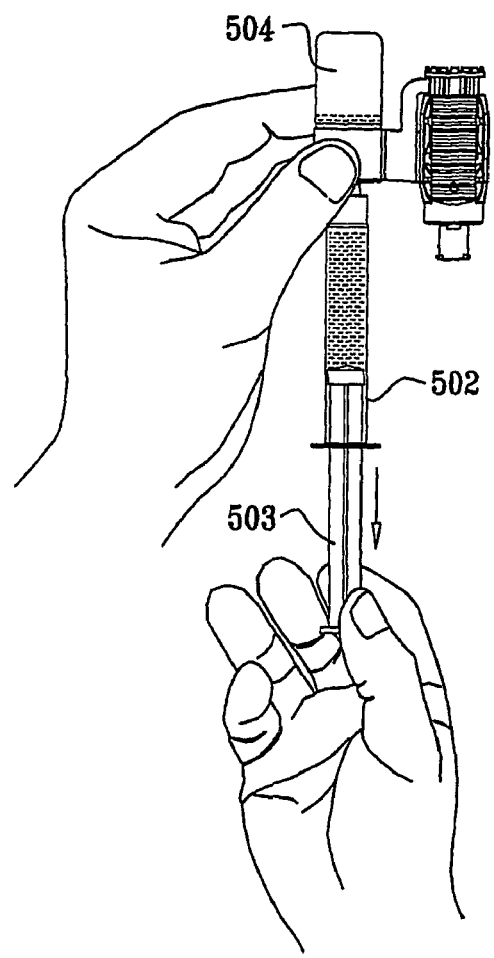

Reference is now made to FIGS. 14A, 14B, 14C, 14D, 14E, 14F, 14G, 14H and 14I, which when taken together form a simplified pictorial illustration of various stages of typical use of the medicinal container engagement and automatic needle device of FIG. 1. In FIG. 14A the medicinal container engagement and automatic needle device of FIG. 1 is shown prior to use in a pre-use operative orientation, described hereinbelow with reference to FIGS. 15A-17B. When ready for use, the user attaches a syringe 502, having its plunger 503 retracted, to the syringe adapter portion 4 of the vial adapter element 2, as seen in FIG. 14A.

Figure 14D:
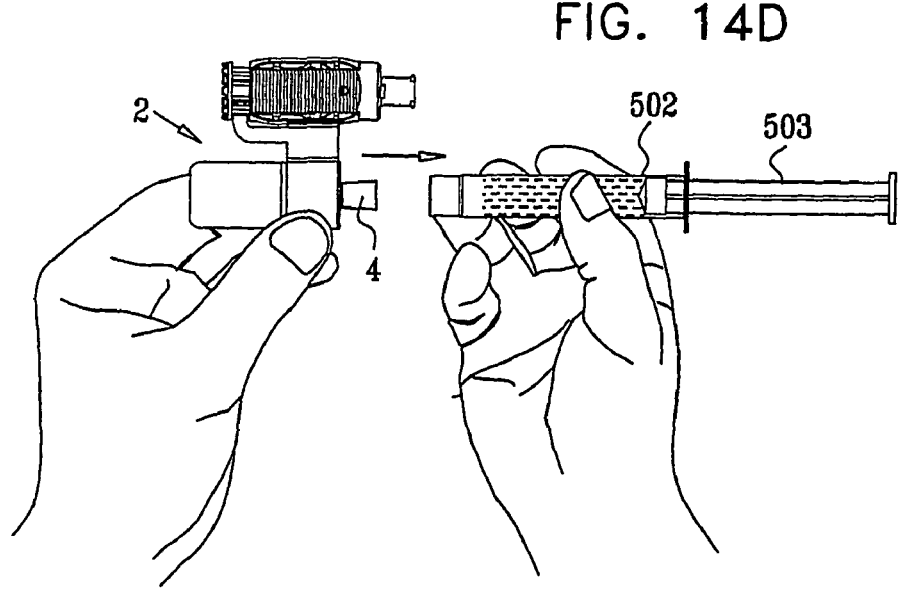

FIG. 14B shows attachment of a vial 504 to the vial port 3 of the vial adapter element 2 and FIG. 14C shows drawing liquid from vial 504 into syringe 502, as described hereinbelow with reference to FIGS. 18-23. FIG. 14D illustrates subsequent disconnection of syringe 502 from syringe adapter portion 4 of vial adapter element 2 as described hereinbelow with reference to FIGS. 24-26, and FIG. 14E shows connection of syringe 502 to tubular portion 110 of needle housing element 10. FIG. 14F shows breaking of the vial adapter element 2 and its connection 12 from needle housing element 10, preferably enabling actuation of the automatic needle functionality of the medicinal container engagement and automatic needle device, by virtue of removal of safety tab 60, as described hereinbelow with reference to FIGS. 27-29B.

It is appreciated that the fact that the vial adapter element 2 is joined to the needle housing element 10 greatly simplifies carrying out of the steps illustrated in FIGS. 14A-14E and thus reduces the chances of error.

Figure 14E:
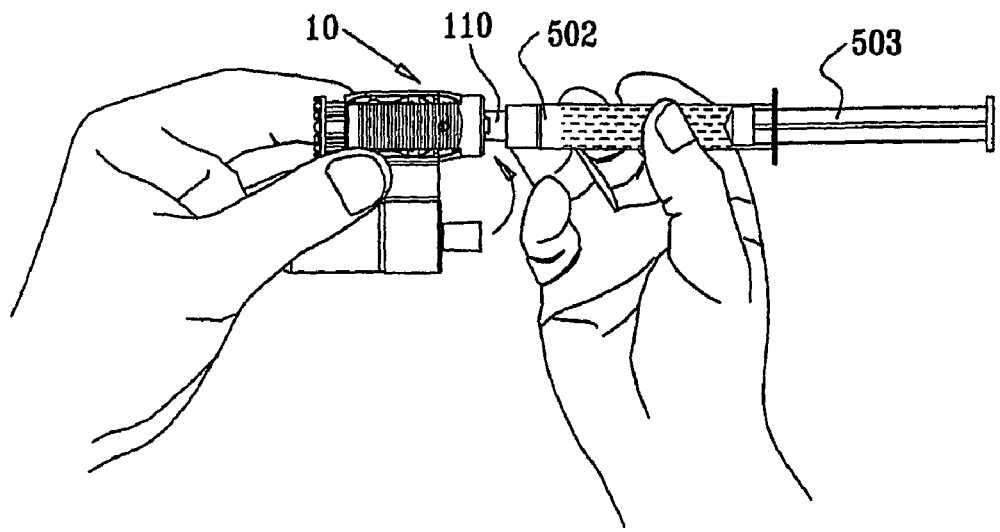
Figure 14F:
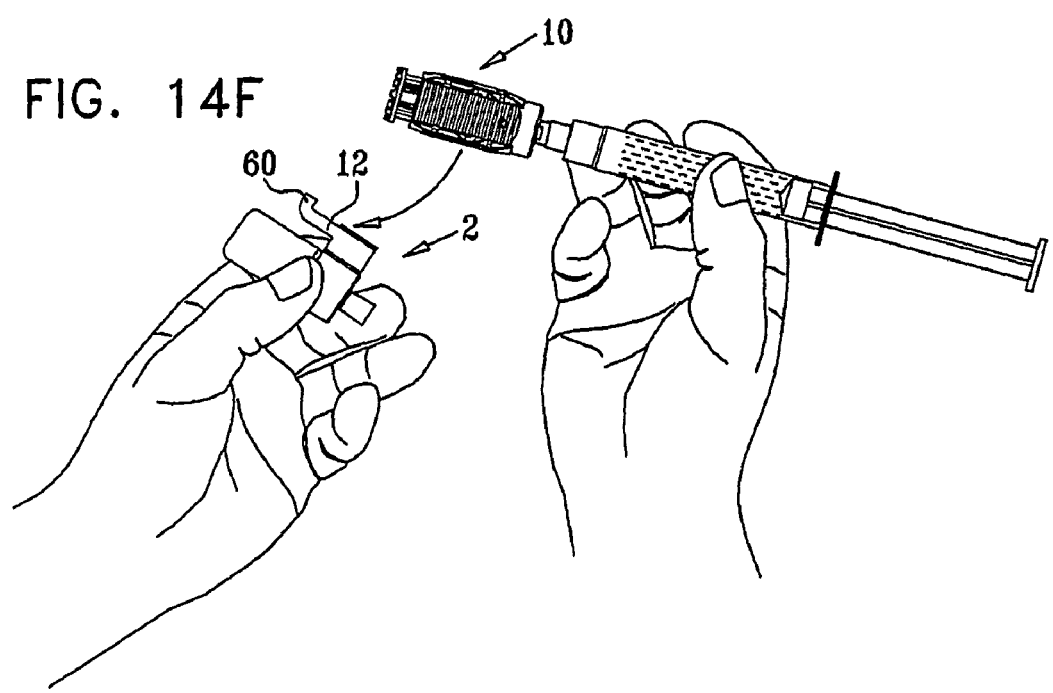
Figure 14G:
Figure 14H:

Reference is now made to FIG. 14G, which shows a user actuating the automatic needle functionality of the medicinal container engagement and automatic needle device by pushing it against an injection site as described hereinbelow with reference to 30-32B. In response to user actuation, automatic needle penetration takes place at the injection site, as indicated in FIG. 14H. Immediately thereafter drug delivery takes place, by user depression of plunger 503 in syringe 502. The operative orientation of the medicinal container engagement and automatic needle device at this stage is described hereinbelow with reference to FIGS. 33-35B.

Figure 14I:
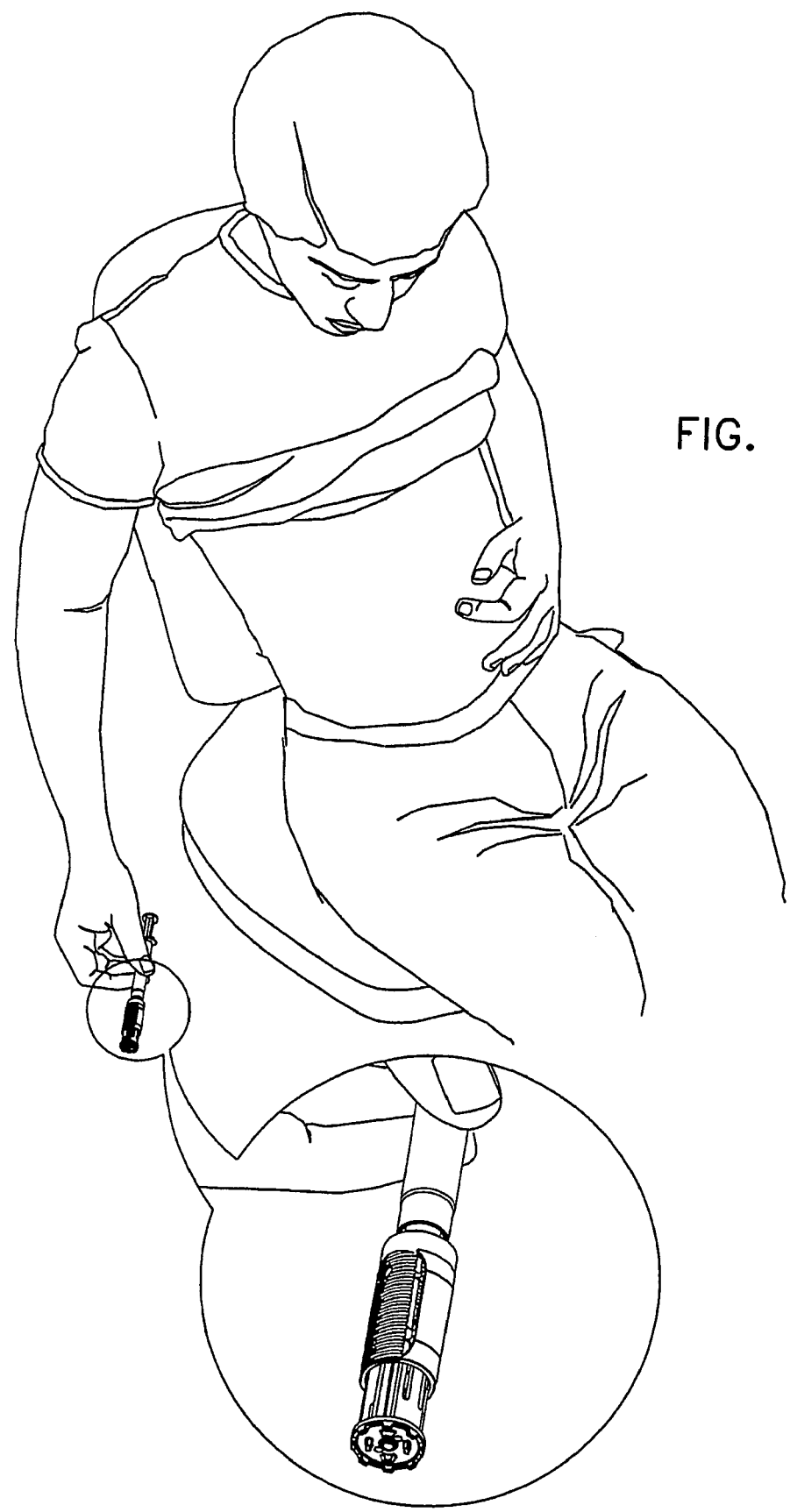

The operative orientation of the medicinal container engagement and automatic needle device immediately following completion of drug delivery and disengagement of the automatic needle from the injection site is indicated in FIG. 14I and is described hereinbelow with reference to FIGS. 36-38B.

Figure 15A:
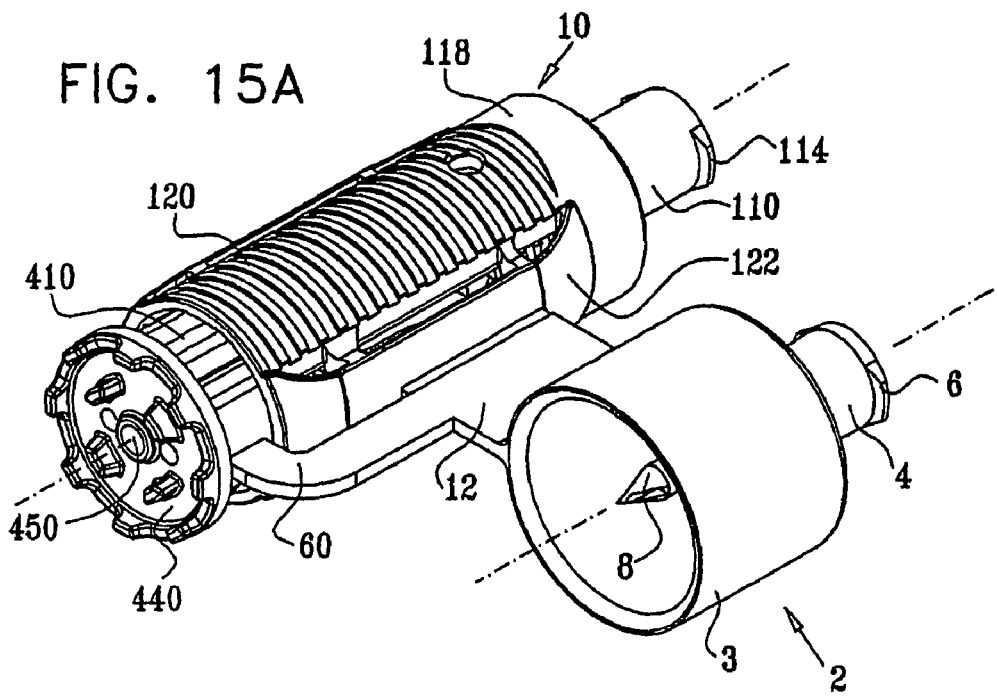
FIGS. 15A and 15B are simplified assembled pictorial view illustrations of the medicinal container engagement and automatic needle device of FIGS. 1 and 14A in a pre-use operative orientation.
Figure 15B:
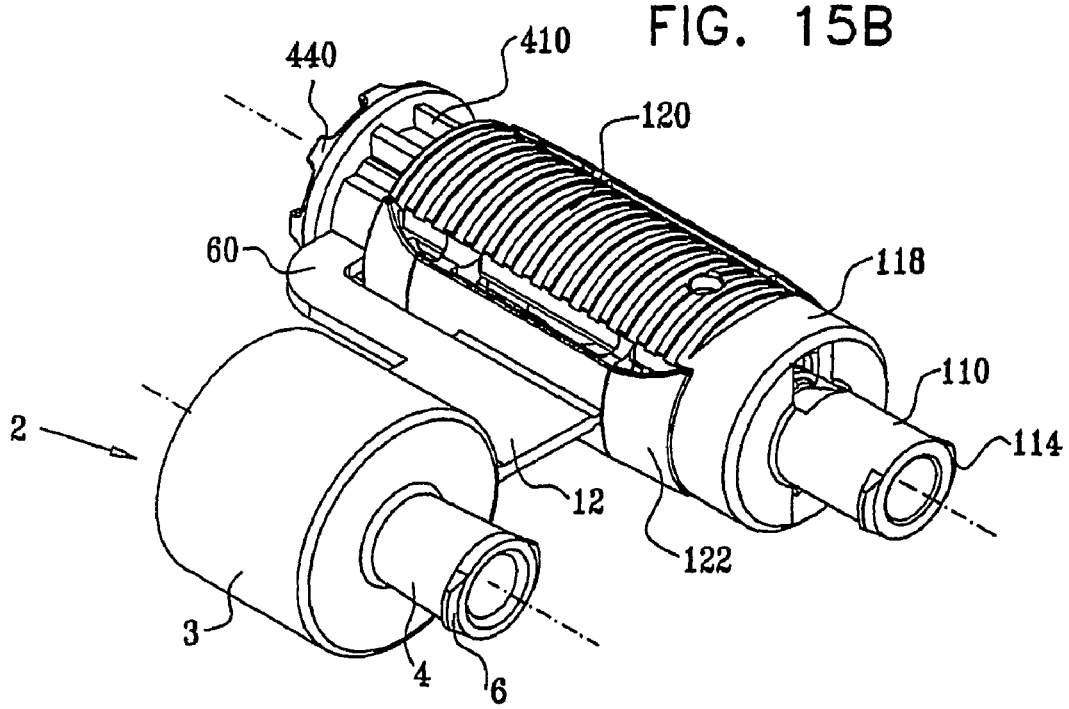
Figure 16A:
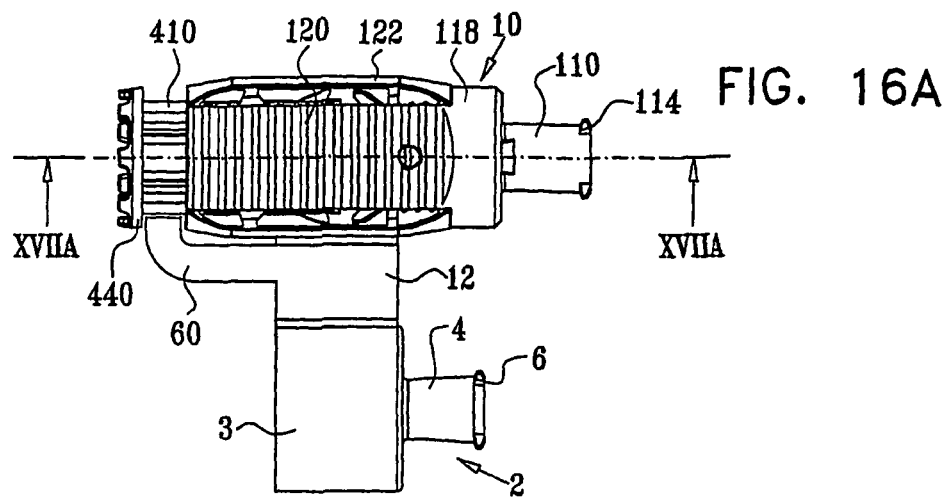
FIGS. 16A and 16B are respective top and side view simplified planar illustrations of the medicinal container engagement and automatic needle device of FIGS. 15A and 15B.
Figure 16B:
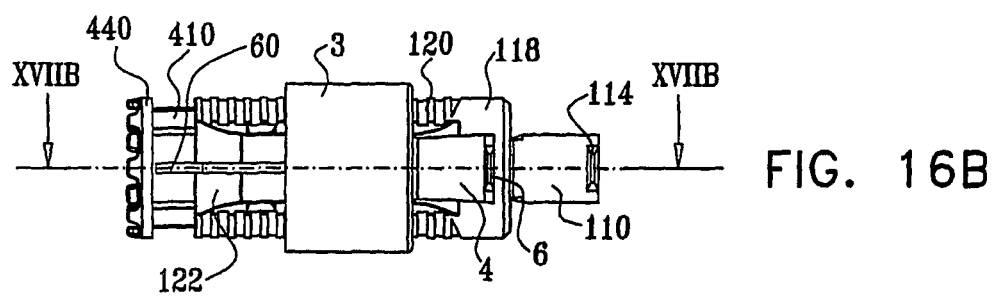
Figure 17A:
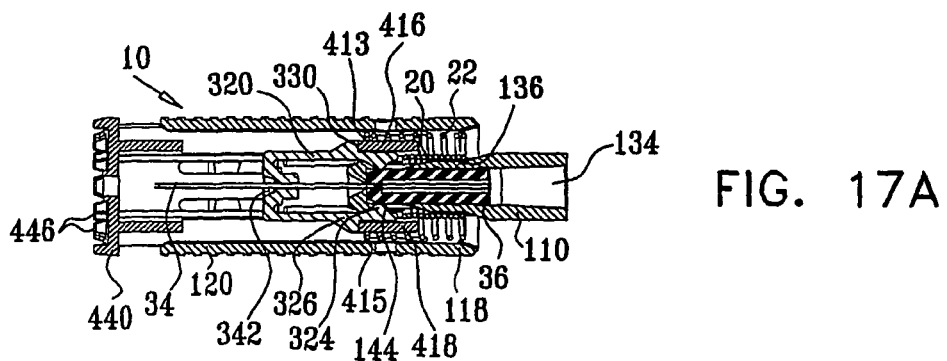
FIGS. 17A and 17B are sectional illustration taken along respective section lines and directions XVIIA-XVIIA and XVIIB-XVIIB in FIGS. 16A and 16B.
Figure 17B:
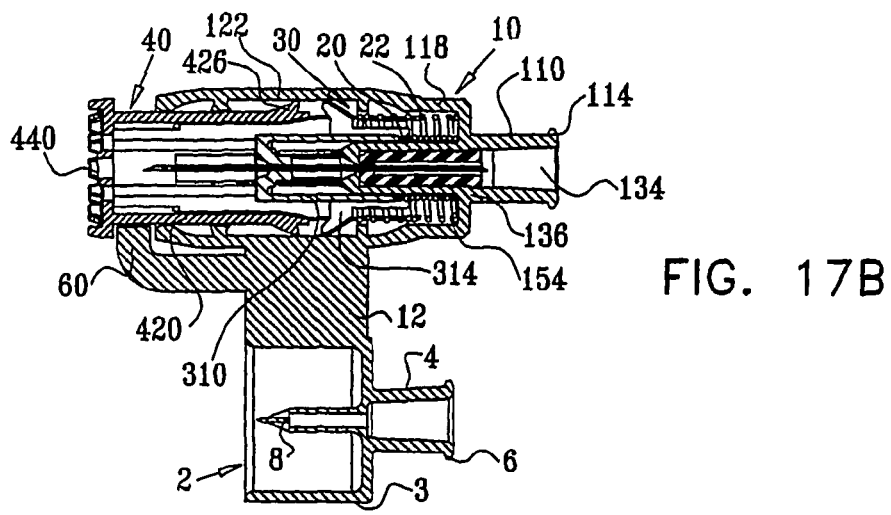

Reference is now made to FIGS. 15A and 15B, which are simplified assembled view illustrations of the medicinal container engagement and automatic needle device of FIGS. 1 and 14A in a pre-use operative orientation, to FIGS. 16A and 16B, which are respective top and side view simplified planar illustrations thereof and to FIGS. 17A and 17B, which are sectional illustrations taken along respective section lines and directions XVIIA-XVIIA and XVIIB-XVIIB in FIGS. 16A and 16B.

As seen in FIGS. 15A-17B, in a pre-use operative orientation of the medicinal container engagement and automatic needle device, suitable for storage, the needle housing element 10 is joined to the needle hub assembly 30 by engagement of inner facing teeth 324 into apertures 144 formed in the cylindrical walls of bore 136. First and second compression springs 20 and 22 are located mutually coaxially within needle housing element 10.

Compression spring 20 is maintained under compression between forward-facing back wall surface 154 of generally cylindrical portion 118 of needle housing element 10 and rearward facing wall portion 350 of hub assembly 30.

Compression spring 22 is maintained under compression between forward facing back wall surface 154 and rearward facing ends 413 and 415 of needle guard element 40, which is slidably retained against forward movement by the positioning of curved rearward facing portions 416 and 418 thereof immediately rearward of teeth 326 of needle hub assembly 30.

The needle hub assembly 30 is retained in place by engagement of outwardly facing surfaces of inner facing teeth 324 of rearwardly extending arms 320 and curved rearward facing portions 416 and 418 of needle guard element 40. This prevents rearwardly extending arms 320 of needle hub assembly 30 from bending outwardly and releasing the engagement of inner facing teeth 324 and apertures 144 formed in the cylindrical walls of bore 136 of the needle housing element 10. The safety tab 60 prevents the needle guard element 40 from moving backwards and allowing needle penetration.

Figure 18:
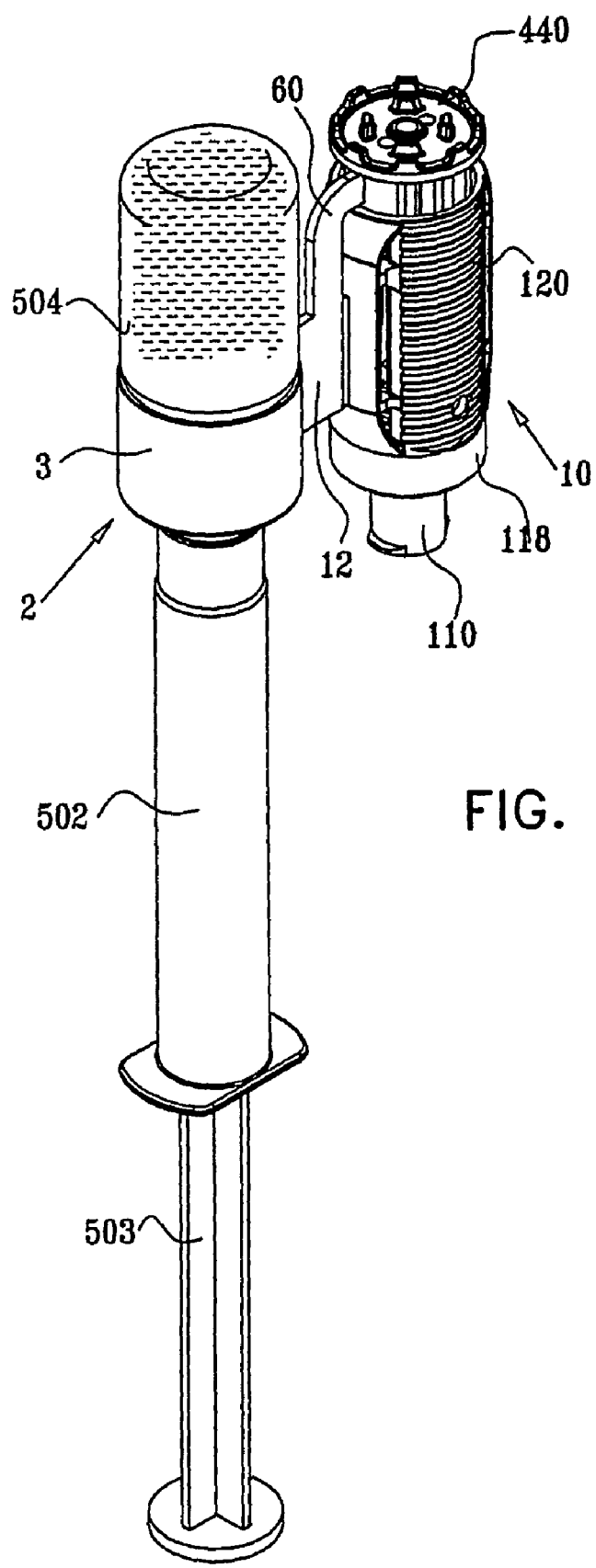
FIG. 18 is a simplified assembled view illustration of the medicinal container engagement and automatic needle device of FIGS. 1, 14A and 14B in a vial engagement operative orientation.

Reference is now made to FIG. 18, which is a simplified assembled view illustration of the medicinal container engagement and automatic needle device of FIGS. 1, 14A and 14B in a vial engagement operative orientation, to FIGS. 19A and 19B, which are respective top and side view simplified planar illustrations thereof and to FIG. 20, which is a sectional illustration taken along section lines XX-XX in FIG. 19B. It is noted that the interior of syringe 502, coupled via syringe adapter portion 4, is in fluid communication with the interior of vial 504, supported in vial port 3, via spike 8.

Figure 21:
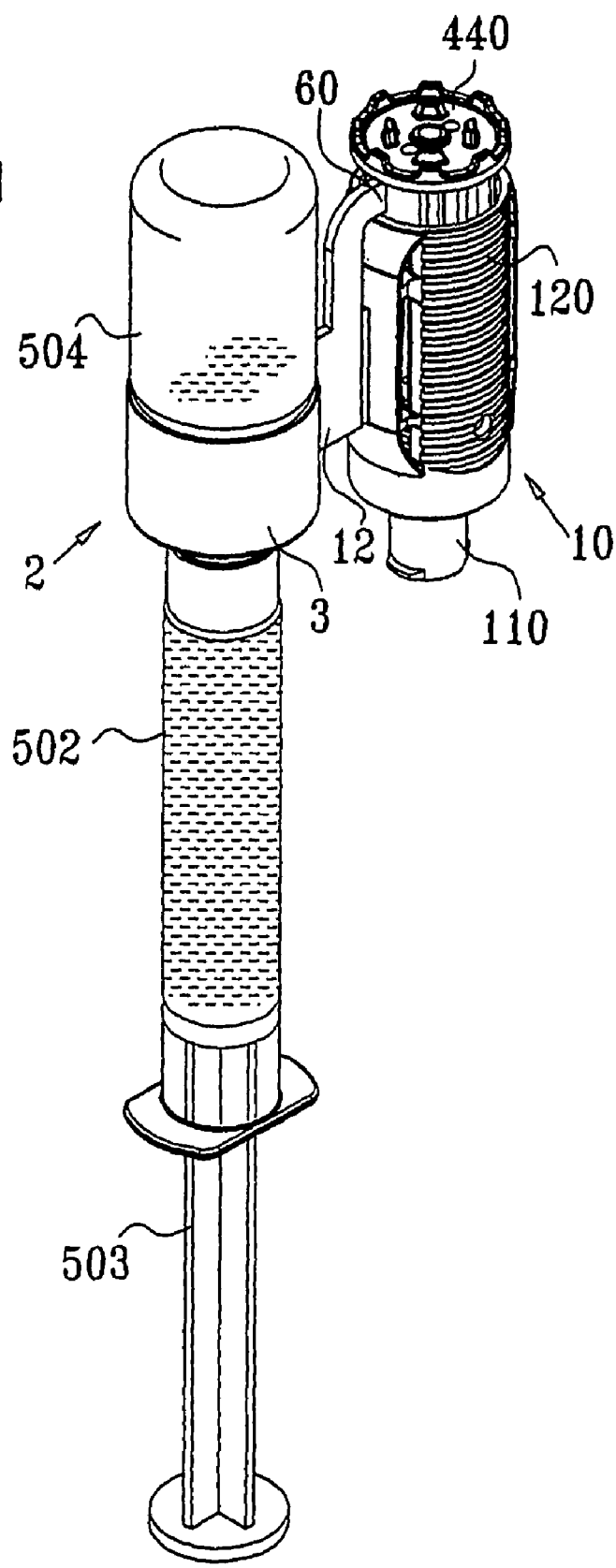
FIG. 21 is a simplified assembled view illustration of the medicinal container engagement and automatic needle device of FIGS. 1 and 14C in a liquid drawing operative orientation.

Reference is now made to FIG. 21, which is a simplified assembled view illustration of the medicinal container engagement and automatic needle device of FIGS. 1 and 14C in a liquid drawing operative orientation, to FIGS. 22A and 22B, which are respective top and side view simplified planar illustrations thereof and to FIG. 23, which is a sectional illustration taken along section lines XXIII-XXIII in FIG. 22B. It is noted that the interior of syringe 502, coupled via syringe adapter portion 4, contains liquid drawn from the interior of vial 504, supported in vial port 3, via spike 8. This stage may take place after mixing liquid from multiple vials and/or reconstitution of lyophilized drugs.

Reference is now made to FIG. 24, which is a simplified assembled view illustration of the medicinal container engagement and automatic needle device of FIGS. 1 and 14E in a syringe-needle housing element engagement operative orientation, to FIGS. 25A and 25B, which are respective top and side view simplified planar illustrations thereof and to FIG. 26, which is a sectional illustration taken along section lines XXVI-XXVI in FIG. 25B. It is noted that the interior of syringe 502, is in fluid communication via bore 134 of tubular portion 110 of needle housing element 10 with needle 34 This stage typically takes place prior to breaking of connection 12 from needle housing element 10.

Figure 27:
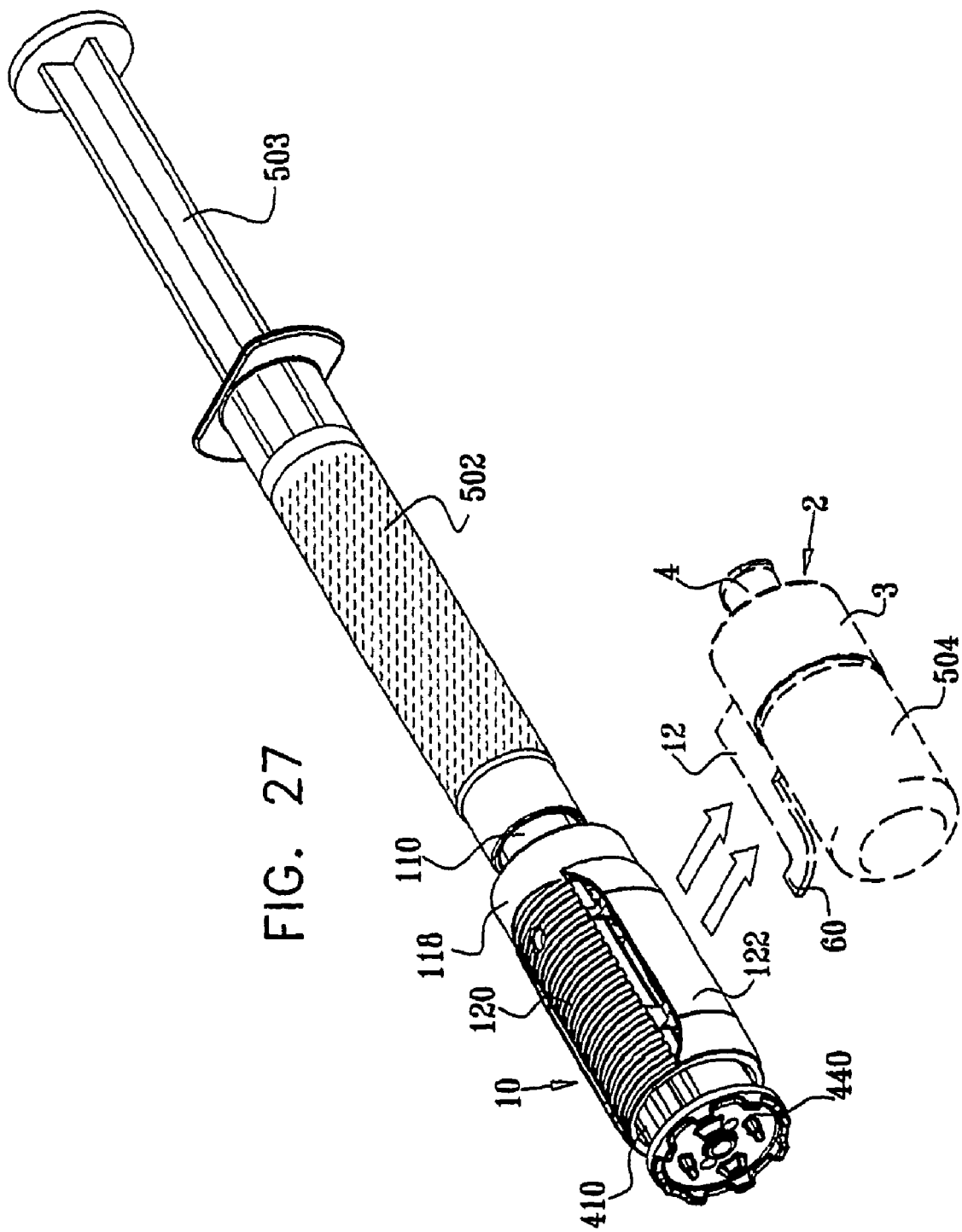
FIG. 27 is a simplified assembled view illustration of the medicinal container engagement and automatic needle device of FIGS. 1 and 14F in a vial adapter element disengagement operative orientation.

Reference is now made to FIG. 27, which is a simplified assembled view illustration of the medicinal container engagement and automatic needle device of FIGS. 1 and 14F in a syringe-needle housing element engagement operative orientation, to FIGS. 28A and 28B, which are respective top and side view simplified planar illustrations thereof and to FIGS. 29A and 29B, which are sectional illustrations taken along section lines XXIXA-XXIXA and XXIXB-XXIXB in FIGS. 28A and 28B respectively. It is noted that the vial adapter element 2 along with its connection 12 is separated from the needle housing element 10 along tapered side protrusion 122 and thus safety tab 60 is also removed. The vial adapter element 2 may be discarded. Alternatively, where a separate safety tab is provided, the vial adapter element 2 need not be separated from the needle housing element 10.

Reference is now made to FIG. 30, which is a simplified pictorial illustration of the medicinal container engagement and automatic needle device of FIGS. 1 and 14G in an injection site engagement operative orientation, to FIGS. 31A and 31B, which are respective top and side view simplified planar illustrations thereof and to FIGS. 32A and 32B, which are sectional illustrations taken along respective section lines and directions XXXIIA-XXXIIA and XXXIIB-XXXIIB in FIGS. 31A and 31B.

As seen particularly in FIG. 32A, due to engagement of the needle guard element 40 with an injection site on a body, the needle guard 40 is forced, against the urging of spring 22, to move axially in a rearward direction with respect to the remainder of the medicinal container engagement and automatic needle device, thus sliding curved rearward facing portions 416 and 418 thereof further rearward of teeth 326 of needle hub assembly 30.

This rearward repositioning of curved rearward facing portions 416 and 418 and the pressure of spring 20, allow arms 320 of needle hub assembly 30 to cantilever outwardly.

Figure 33:
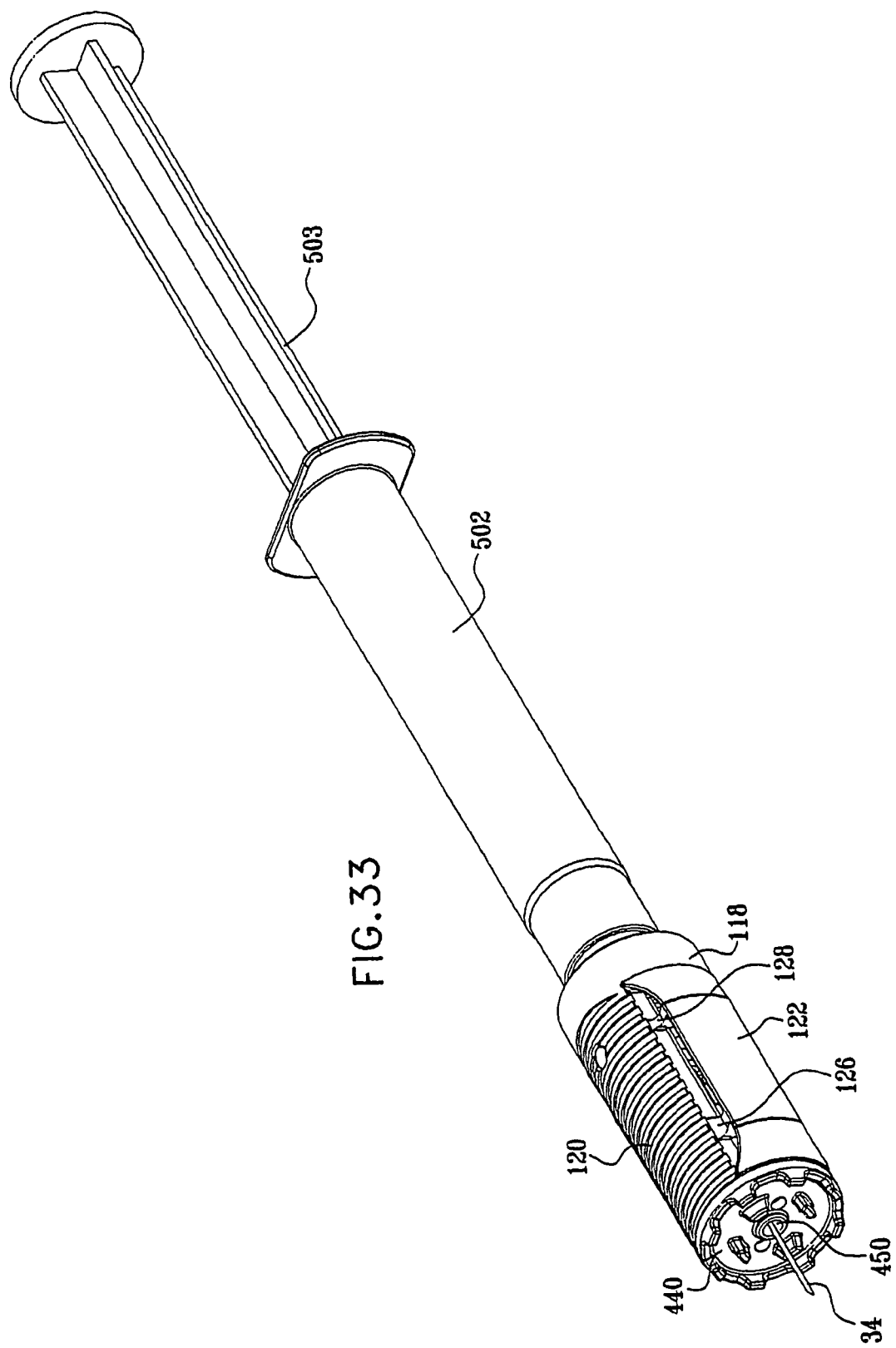
FIG. 33 is a simplified pictorial illustration of the medicinal container engagement and automatic needle device of FIGS. 1 and 14H in an actuated operative orientation.

Reference is now made to FIG. 33, which is a simplified pictorial illustration of the medicinal container engagement and automatic needle device of FIGS. 1 and 14H in an actuated operative orientation, to FIGS. 34A and 34B which are respective top and side view simplified planar illustrations thereof and to FIGS. 35A and 35B which are sectional illustrations taken along respective section lines and directions XXXVA-XXXVA and XXXVB-XXXVB in FIGS. 34A and 34B.

As seen particularly in FIG. 35A, under the urging of spring 20, inner facing teeth 324 slide out of apertures 144 formed in the cylindrical walls of bore 136, thus allowing the needle hub assembly 30 to move axially forward and to provide needle penetration. The forward motion of needle hub assembly 30 stops when protrusions 312 and 314 come into touching engagement with inwardly extending transverse ribs 126 of the housing 10. At this stage, drug delivery may take place in response to manual operation of syringe 502

It is appreciated that at all times needle 34 sealingly and slidably engages septum 36.

Figures 38A, 38B:
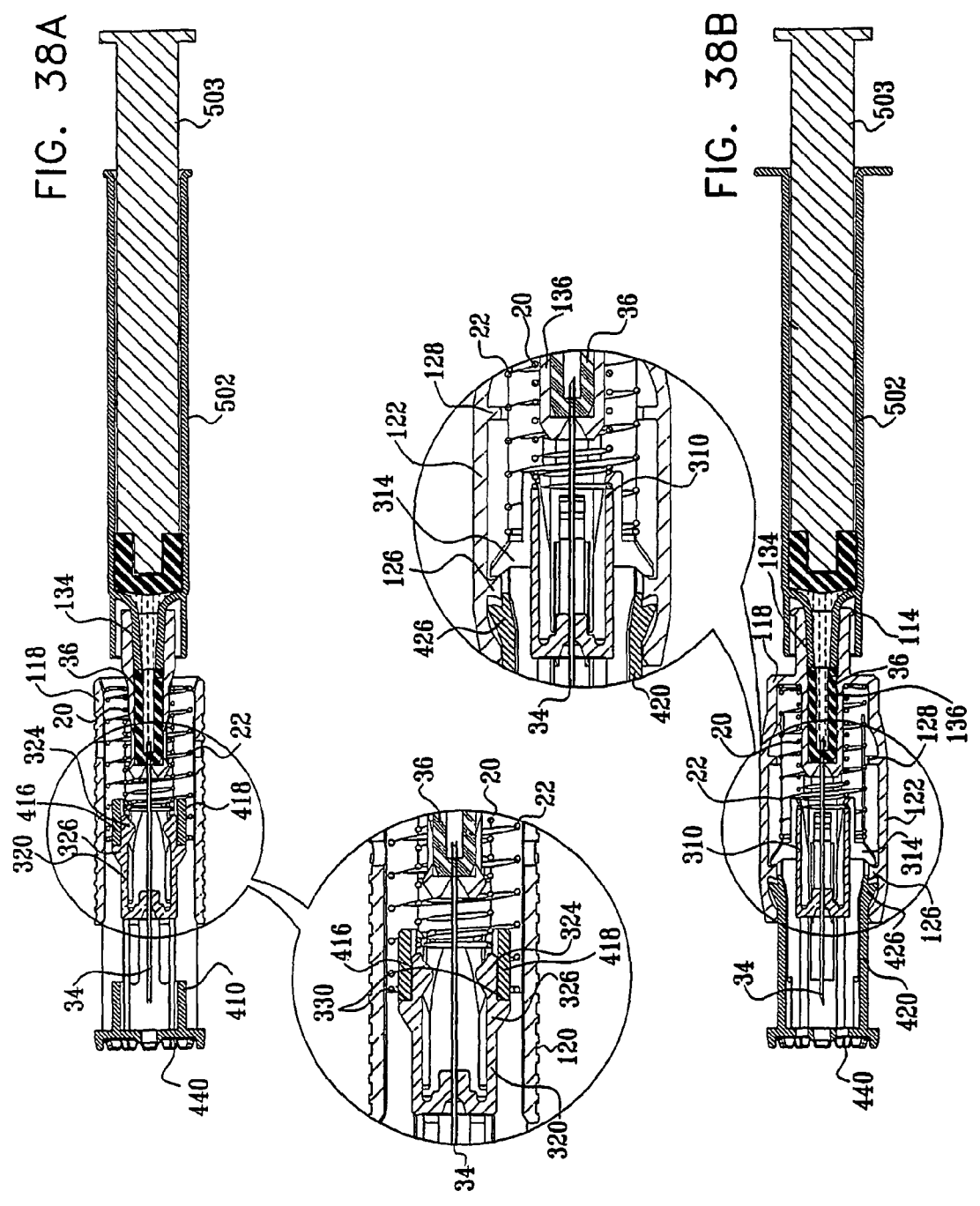

Reference is now made to FIG. 36, which is a simplified pictorial illustration of the medicinal container engagement and automatic needle device of FIGS. 1 and 14I in a post-drug delivery, needle guarded operative orientation, to FIGS. 37A and 37B, which are respective top and side view simplified planar illustrations thereof and to FIGS. 38A and 38B, which are sectional illustrations taken along respective section lines and directions XXXVIIIA-XXXVIIIA and XXXVIIIB-XXXVIIIB in FIGS. 37A and 37B.

FIGS. 36-38B illustrate the medicinal container engagement and automatic needle device fully disengaged from the injection site and the needle guard 40 is fully extended under the urging of spring 22 to fully enclose the needle 34. The needle guard 40 is prevented from moving farther forwards by engagement of curved rearward facing portions 416 and 418 and rearwardly extending surface 330 of teeth 326 of needle hub assembly 30. The needle hub assembly 30 is prevented from moving further forward by protrusions 312 and 314 leaning against inwardly extending transverse ribs 126 of the housing 10. The needle guard 40 is prevented from moving rearwardly by outwardly facing tooth 426, which fits in front of inwardly extending transverse ribs 126 of the needle housing element 10. Therefore, at this stage the needle guard 40 is locked in place, protecting keeping the needle 34 from inadvertent engagement.

It is appreciated that the medicinal container engagement and automatic needle device can be attached to various types of injection devices, and that the a luer adapter defined by an internal tapered surface of the tubular portion 110 of the needle housing element 10 and the syringe adapter portion 4 of the medicinal container engagement and automatic needle device may be readily modified for engagement with various injection devices such as pen injectors.

Figure 39:
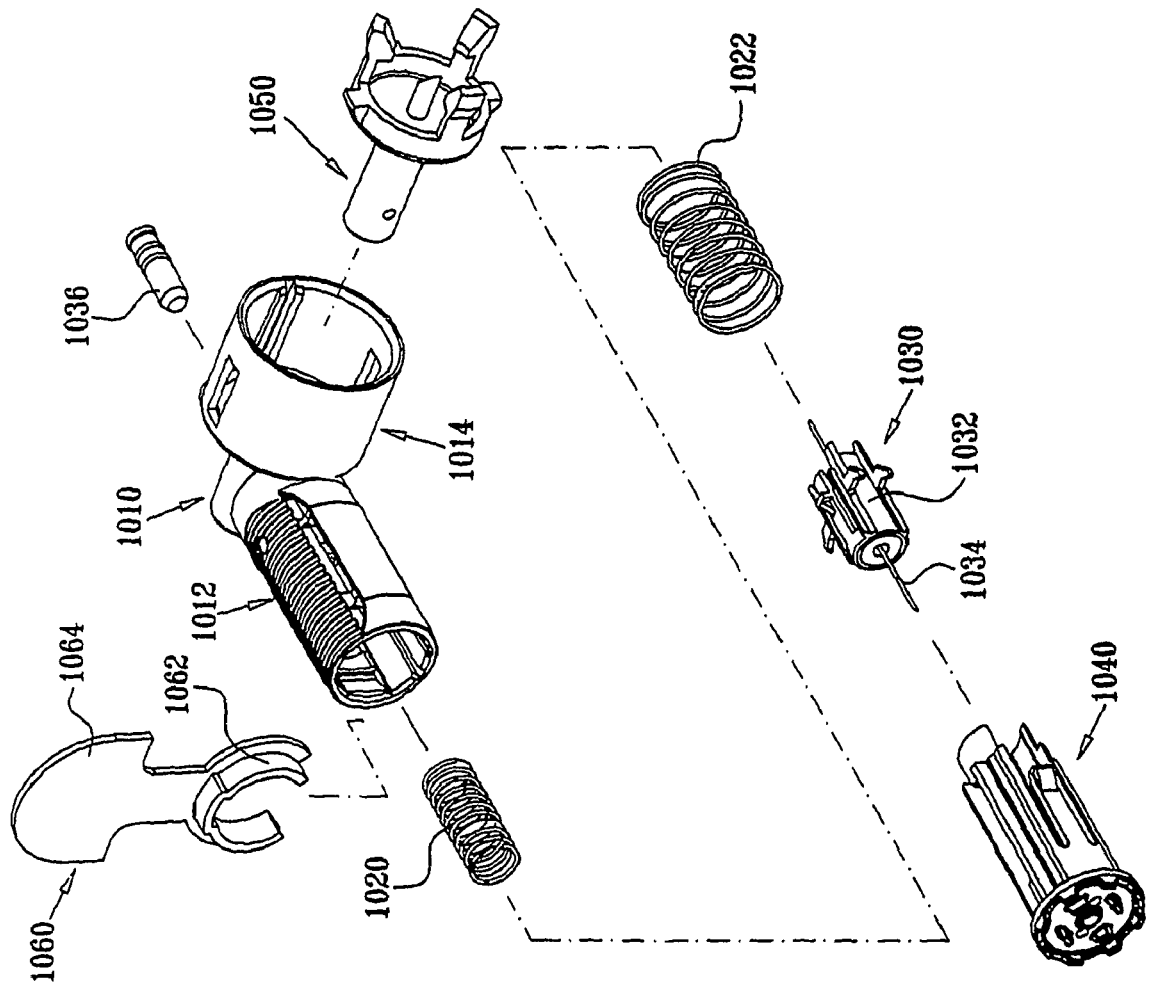
FIG. 39 is a simplified exploded view illustration of a medicinal container engagement and automatic needle device constructed and operative in accordance with another preferred embodiment of the present invention.

Reference is now made to FIG. 39 is a simplified exploded view illustration of a medicinal container engagement and automatic needle device constructed and operative in accordance with another preferred embodiment of the present invention.

As seen with particular clarity in FIG. 39, the medicinal container engagement and automatic needle device comprises a housing element 1010 which includes an automatic needle housing portion 1012 and a vial adapter housing portion 1014.

Disposed within automatic needle housing portion 1012 are generally coaxially seated respective first and second compression springs 1020 and 1022, which provide selectable forward displacement to a needle hub assembly 1030, which includes a hub portion 1032 and a needle 1034 adhesively adhered thereto and extending rearwardly through a septum 1036, and to a needle guard element 1040. Alternatively, needle hub portion 1032 may be injected onto the needle, by a method such as insert molding.

Selectably positionable in vial adapter housing portion 1014 is a two-position vial communication element 1050 which is generally operative to provide fluid communication only between the interior of a syringe and the interior of a vial, when a vial operatively engages the communication element 1050 and to provide fluid communication only between the interior of the syringe and needle 1034, when a vial does not engage the communication element 1050.

A safety tab 1060 including a tubular portion 1062 and a tab portion 1064 is preferably mounted onto the needle guard element 1040 and in front of housing element 1010, thus disabling actuation of the medicinal container engagement and automatic needle device. The medicinal container engagement and automatic needle device is only functional once the safety tab is removed, as described hereinbelow.

It will be appreciated by persons skilled in the art that safety tab 1060 can be formed of any suitable material, for example such as polypropylene, and may designed in many different shapes, such as a portion which is inserted into a slot between the needle guard element 1040 and the housing element 1010, as a stand alone injection molded part, or as an integral part of any suitable part of the medicinal container engagement and automatic needle device.

It will additionally be appreciated by those skilled in the art that compression springs 1020 and 1022 may be replaced with a resilient element such as tension springs, elastomeric compression springs or plastic springs which may be integrated into housing element 1010, into needle hub portion 1032 or into needle guard element 1040.

Figure 40A:
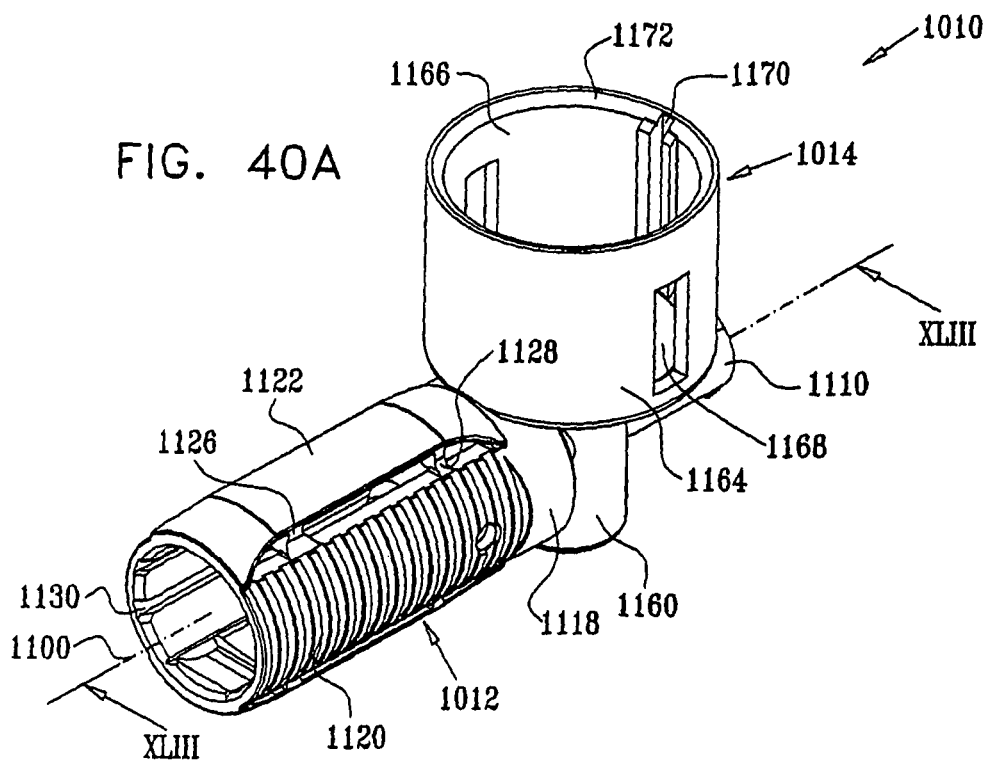
FIGS. 40A and 40B are simplified pictorial illustrations of a housing element which forms part of the medicinal container engagement and automatic needle device of FIG. 39.
Figure 40B:
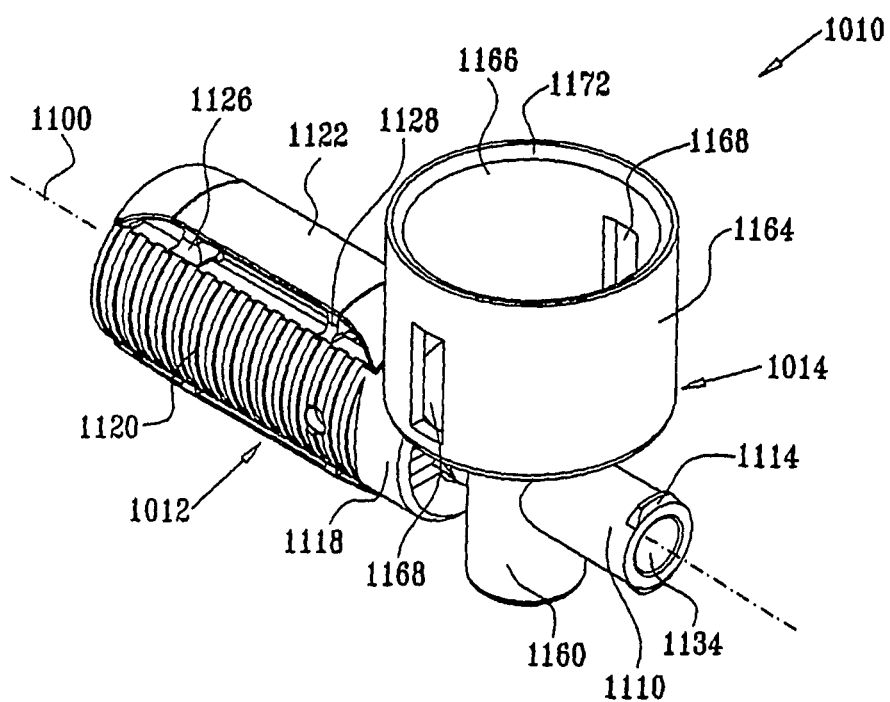
Figure 41A:
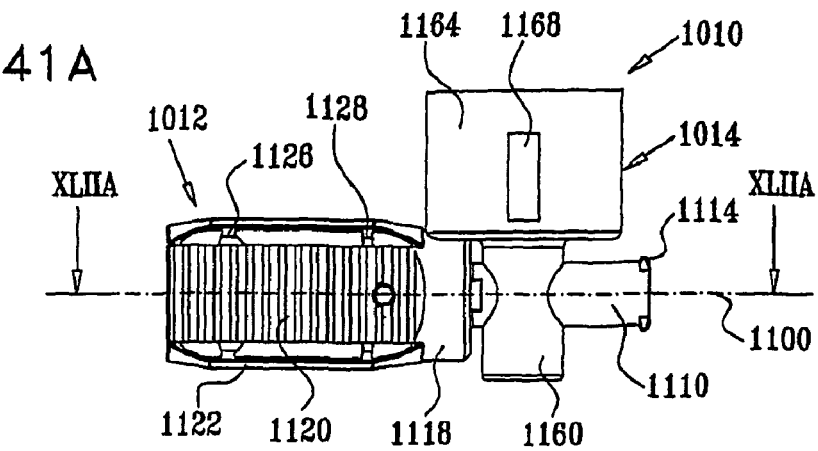
FIGS. 41A and 41B are respective top and side view simplified planar illustrations of the housing element of FIGS. 40A and 40B.
Figure 41B:
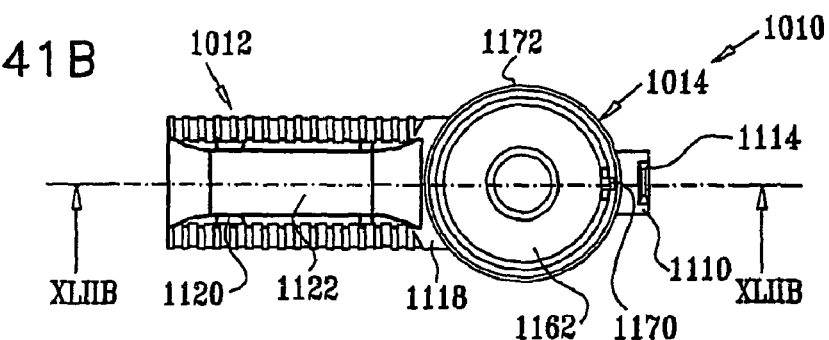
Figure 42A:
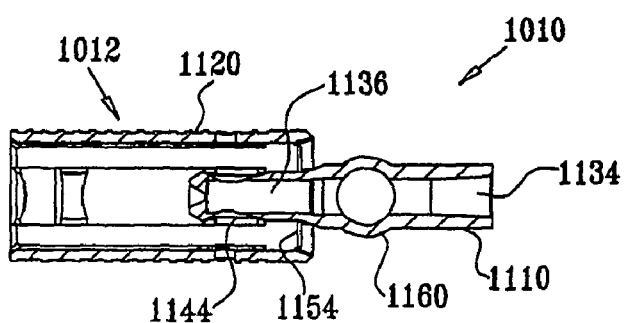
FIGS. 42A and 42B are sectional illustrations taken along respective section lines XLIIA-XLIIA and XLIIB-XIIB in FIGS. 41A and 41B.
Figure 42B:
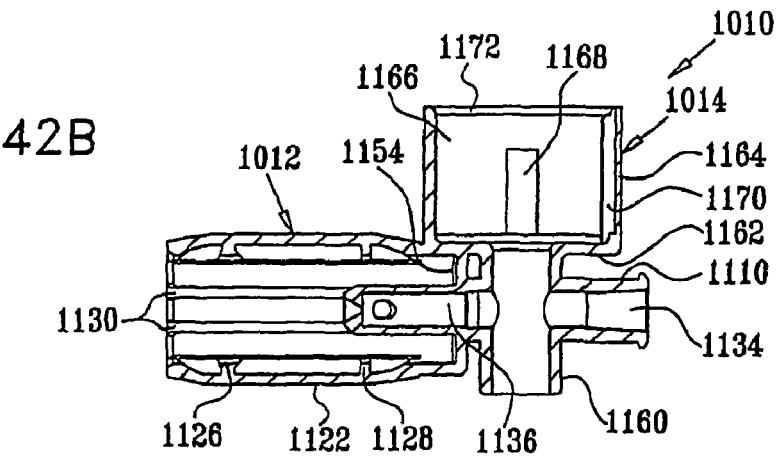
Figure 43:
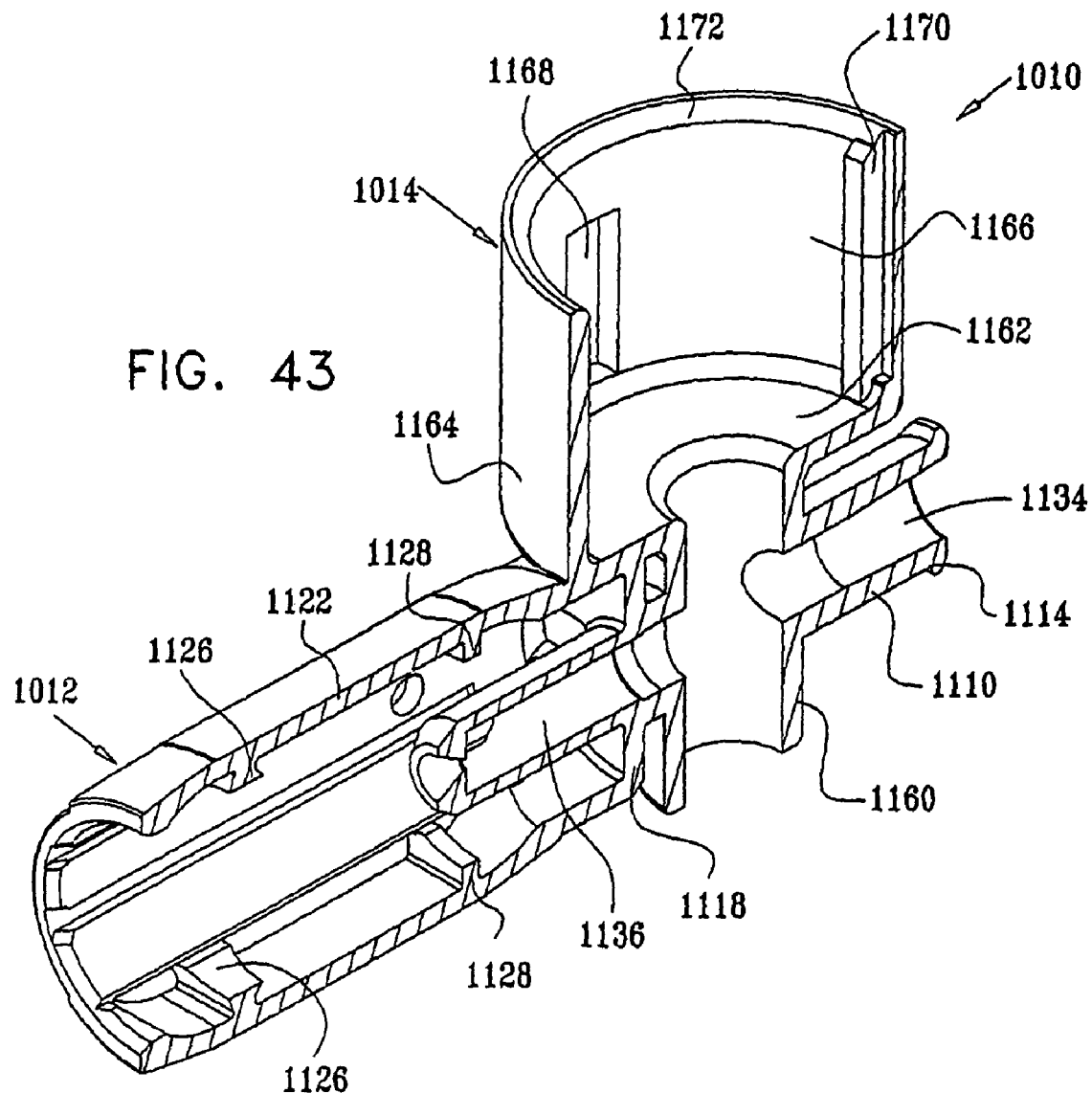
FIG. 43 is a pictorial sectional illustration taken along section line XLIII-XLIII in FIG. 40A.

Reference is now made to FIGS. 40A and 40B, which are simplified pictorial illustrations of a preferred housing element 1010 which forms part of the medicinal container engagement and automatic needle device of FIG. 39, to FIGS. 41A and 41B which are respective top and side view simplified planar illustrations thereof, to FIGS. 42A and 42B which are sectional illustrations taken along respective section lines and directions XLIIA-XLIIA and XLIIB-XLIIB in FIGS. 41A and 41B and to FIG. 43 which is a pictorial sectional illustration taken along section line XLIII-XLIII in FIG. 40A.

As seen in FIGS. 40A-43, the housing element 1010 preferably is an integrally formed element, preferably injection molded of plastic. Housing element 1010 preferably has a generally cylindrical configuration and is preferably side-to-side symmetric about a longitudinal axis 1100, and as noted above, includes an automatic needle housing portion 1012 and a vial adapter housing portion 1014.

Automatic needle housing portion 1012 is similar to needle housing element 1010 described above in the embodiment of FIGS. 1-38B and preferably includes a rearward generally tubular portion 1110, which terminates in an open back and defines generally symmetric side-facing tabs 1114. Forward of rearward generally tubular portion 1110 there is provided a generally cylindrical portion 1118, whose outer configuration preferably includes top and bottom grip regions 1120, which are ribbed in a direction transverse to longitudinal axis 1100 and first and second forwardly and rearwardly tapered side protrusions 1122.

At an inner surface of generally cylindrical portion 1118 there are provided forward and rearward inwardly extending transverse ribs 1126 and 1128 and a plurality of inwardly extending longitudinal slots 1130. The interior of tubular portion 1110 defines a generally cylindrical bore 1134. Bore 1134 communicates via a tapered interface with a forward bore 1136, disposed interiorly of cylindrical portion 1118, which is arranged to receive septum 1036. Bore 1136 has a circular cross section which is slightly smaller than that of bore 1134.

Apertures 1144 are formed in the cylindrical walls of bore 1136 in alignment along a line extending transversely to longitudinal axis 1100. A forward-facing back wall surface 1154 of generally cylindrical portion 1118 defines a spring seat for springs 1020 and 1022.

Vial adapter housing portion 1014 includes a tubular portion 1160 which intersects and communicates with tubular portion 1110 and extends to a base 1162 of a cylindrical vial port 1164 having a cylindrical wall 1166 in which are preferably formed a plurality of slots 1168 and a track 1170. Cylindrical wall 1166 preferably defines a inwardly tapered circumferential edge 1172.

The housing element 1010 may optionally be formed with a pair of side-to-side symmetric windows, to allow viewing of the tip of the needle 1034, for example, when purging air bubbles from syringe 2006. Alternatively, housing element 1010 may be formed of a transparent material.

Reference is now made to FIGS. 6A and 6B, which are simplified pictorial illustrations of a needle hub assembly 30 which forms part of the medicinal container engagement and automatic needle device of FIG. 1, to FIGS. 7A and 7B, which are respective top and side view simplified planar illustrations of the needle hub assembly of FIGS. 6A and 6B, to FIGS. 8A and 8B, which are sectional illustrations taken along respective section lines and directions VIIIA-VIIIA and VIIIB-VIIIB in FIGS. 7A and 7B and to FIGS. 9A and 9B, which are pictorial sectional illustrations taken along respective section lines and directions IXA-IXA and IXB-IXB in FIG. 6A.

The needle hub assembly 1030 is identical to needle hub assembly 30 shown in FIGS. 6A-9B.

Figure 13A:
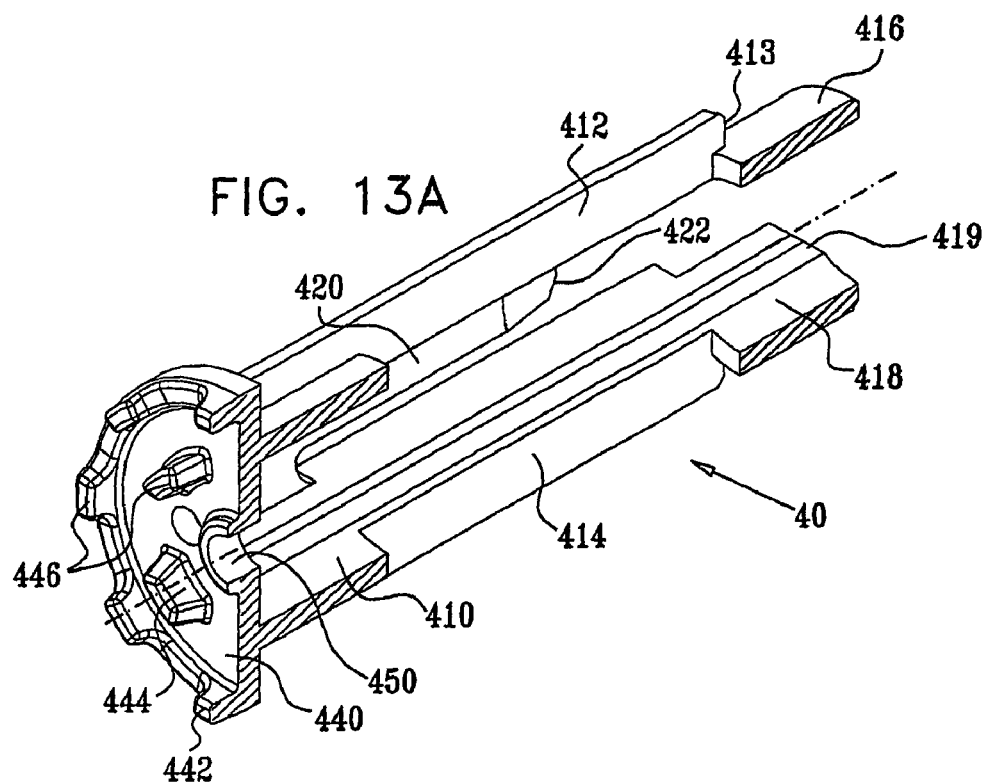
FIGS. 13A and 13B are pictorial sectional illustrations taken along respective section lines and directions XIIIA-XIIIA and XIIIB-XIIIB in FIG. 10A.
Figure 13B:
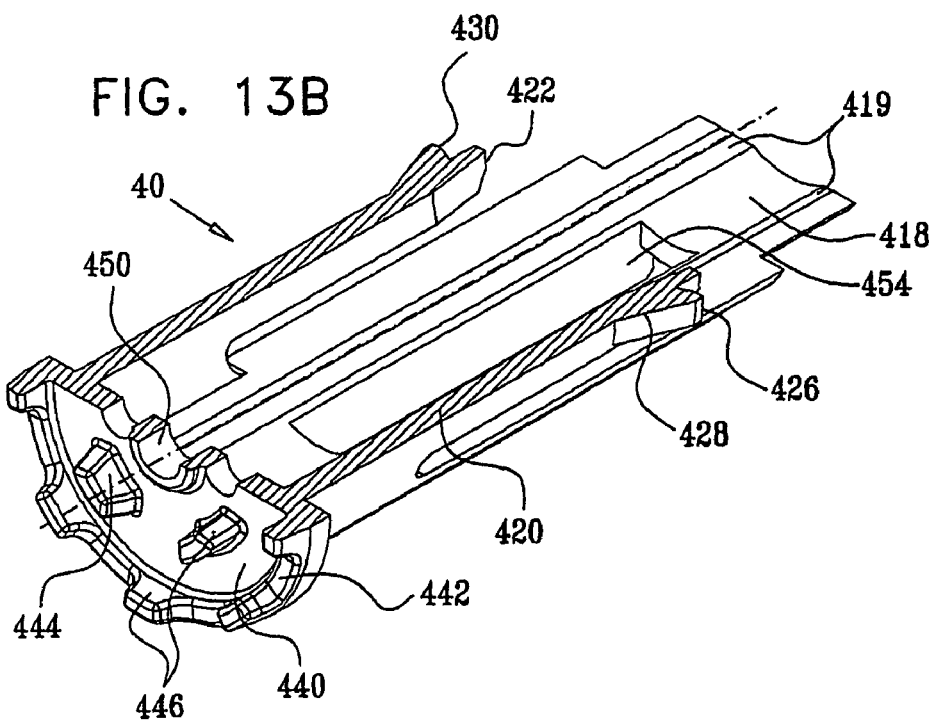

Reference is now made to FIGS. 10A and 10B, which are simplified pictorial illustrations of a needle guard element 40 which forms part of the medicinal container engagement and automatic needle device of FIG. 1, to FIGS. 11A and 11B, which are respective top and side view simplified planar illustrations of the needle guard element of FIGS. 10A and 10B, to FIGS. 12A and 12B, which are sectional illustrations taken along respective section lines and directions XIIA-XIIA and XIIB-XIIB in FIGS. 11A and 11B and to FIGS. 13A and 13B which are pictorial sectional illustrations taken along respective section lines and directions XIIIA-XIIIA and XIIIB-XIIIB in FIG. 10A.

The needle guard element 1040 is identical to needle guard element 40 shown in FIGS. 10A-13B.

Figure 44:
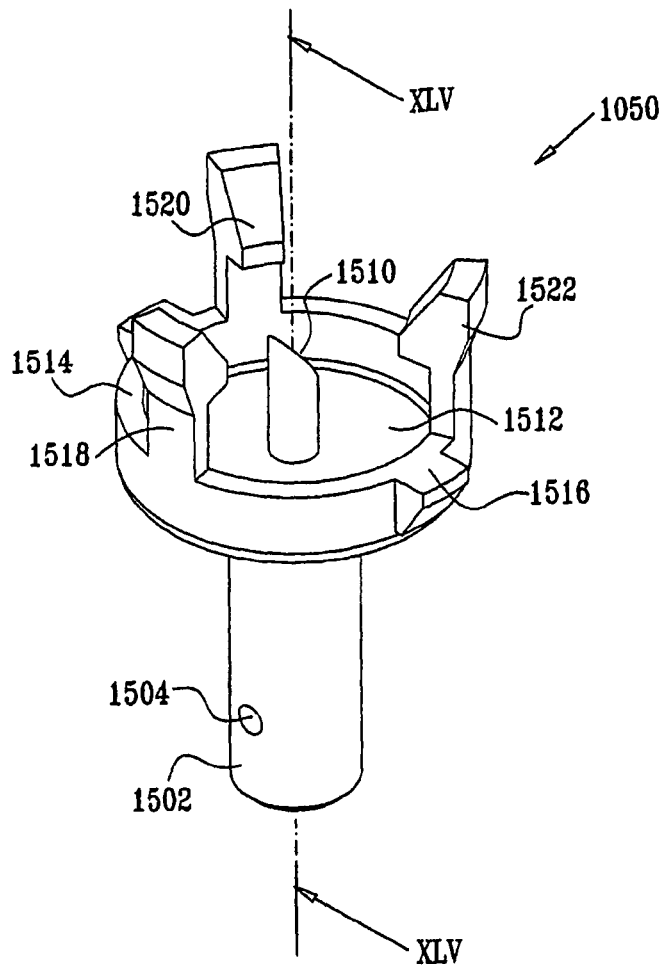
FIG. 44 is a simplified pictorial illustration of a vial communication element which forms part of the medicinal container engagement and automatic needle device of FIG. 39.
Figure 45:
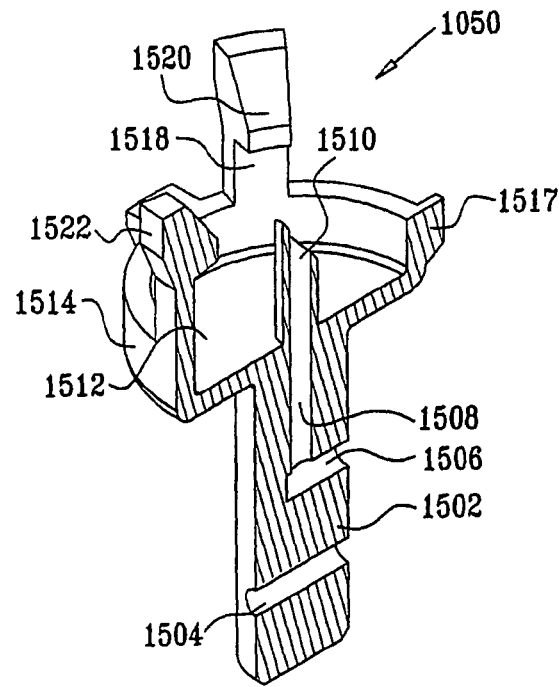
FIG. 45 is a pictorial sectional illustration taken along section line XLV-XLV in FIG. 44.

Reference is now made to FIGS. 44 and 45 which together illustrate two-position vial communication element 1050. As seen in FIGS. 44 and 45, two-position vial communication element 1050 includes a generally cylindrical portion 1502, including a throughgoing transverse bore 1504 and a partially throughgoing transverse bore 1506, axially spaced from bore 1504 and communicating with an axial bore 1508 which terminates in a hollow spike 1510.

Spike 1510 extends from a base 1512 which is surrounded by a ring 1514. Extending radially outwardly from ring 1514 are a plurality of slot engagement elements 1516 which engage slots 1168 in cylindrical wall 1166 and limit axial travel of two-position vial communication element 1050 relative thereto. Also preferably extending radially outwardly from ring 1514 there is provided a track riding protrusion 1517 which rides along track 1170.

Extending axially from ring 1514 are a plurality of resilient vial engagement fingers 1518 having inwardly facing protrusions 1520, whose operative engagement with a neck of a vial tends to displace the vial communication element 1050 axially along with the vial relative to vial adapter housing portion 1014 subject to the limits established by engagement of slot engagement elements 1516 and slots 1168.

Preferably fingers 1518 also include outwardly facing protrusions 1522 which resiliently engage circumferential edge 1172 in a manner which tends to result in establishment of fluid communication between the interior of a vial via spike 1510 and bores 1506 and 1508 prior to axial displacement of vial communication element 1050.

Generally, the two-position vial communication element 1050 engages the interior of cylindrical wall 1166 resulting in friction between tubular portion 1502 and tubular portion 1160 and thus tends to retain its axial position relative to vial adapter housing portion 1014 in the absence of application of an axial force thereto by engagement with a vial.

Figure 46A:
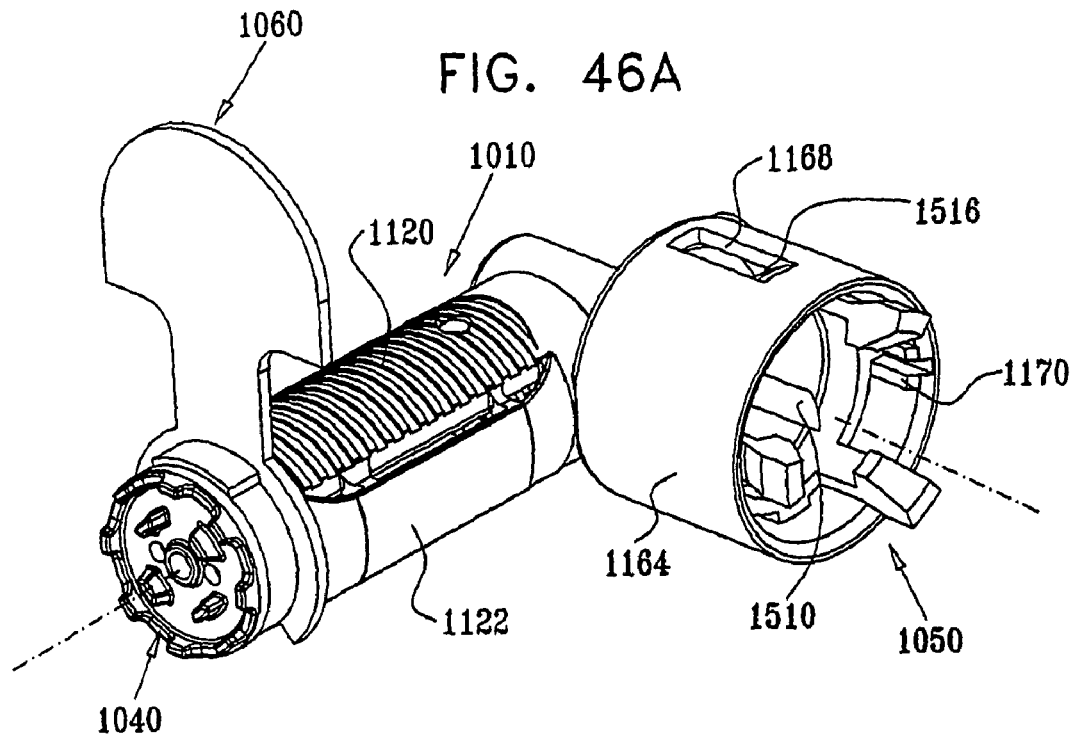
FIGS. 46A and 46B are simplified assembled pictorial view illustrations of the medicinal container engagement and automatic needle device of FIG. 39 in a pre-use operative orientation.
Figure 46B:
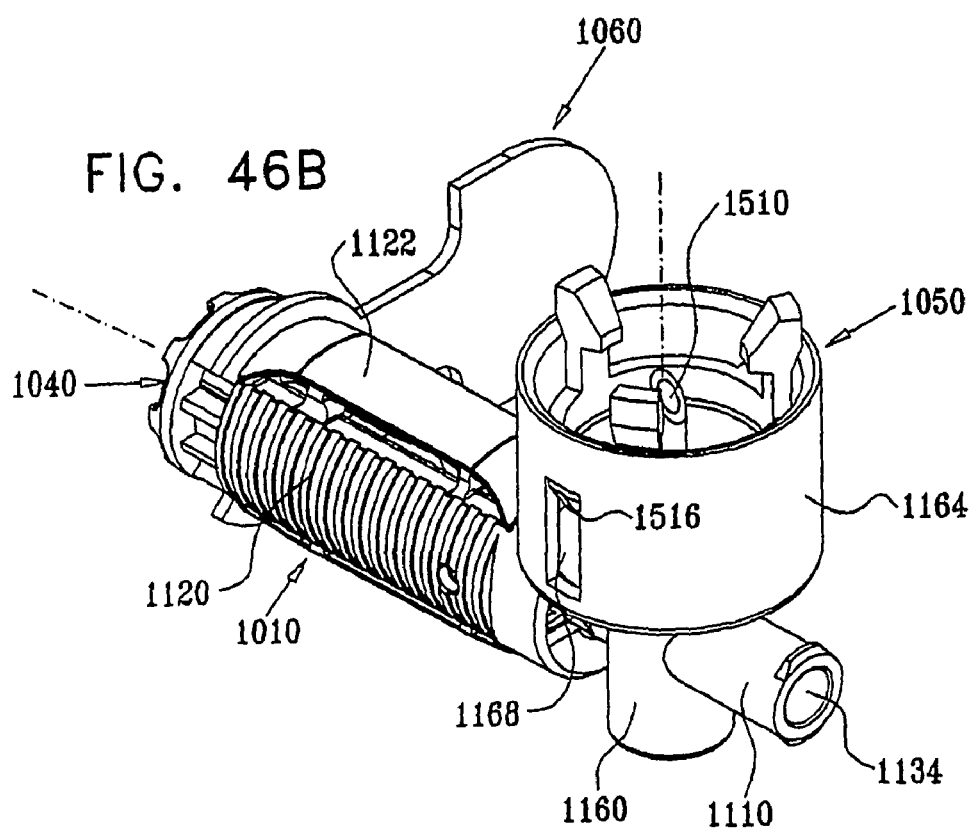
Figure 47A:
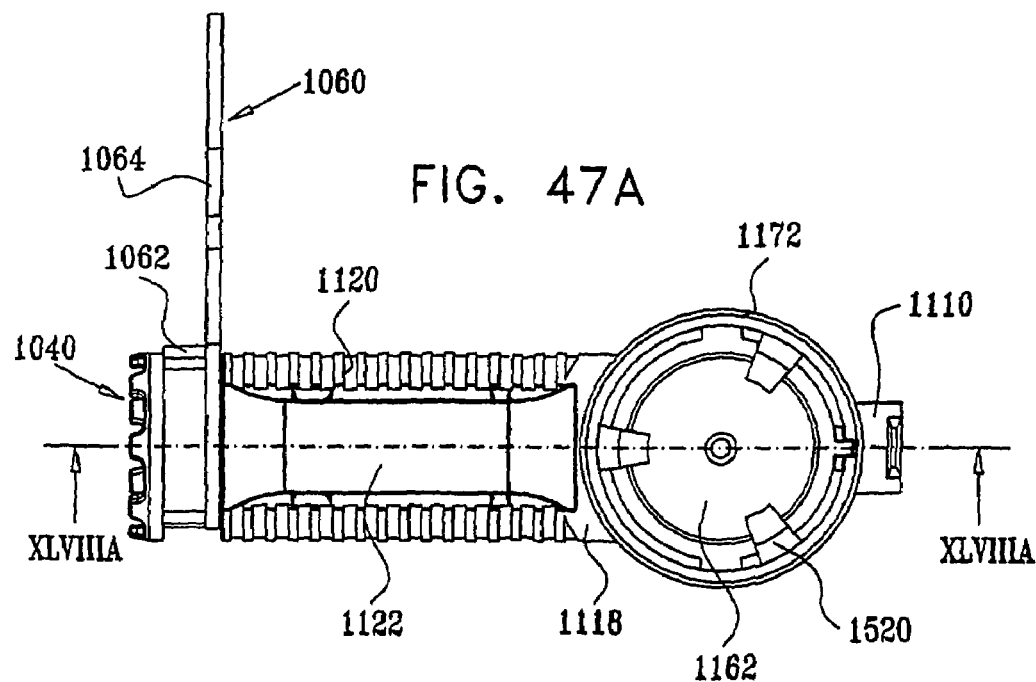
FIGS. 47A and 47B are respective top and side view simplified planar illustrations of the medicinal container engagement and automatic needle device of FIGS. 46A and 46B.
Figure 47B:
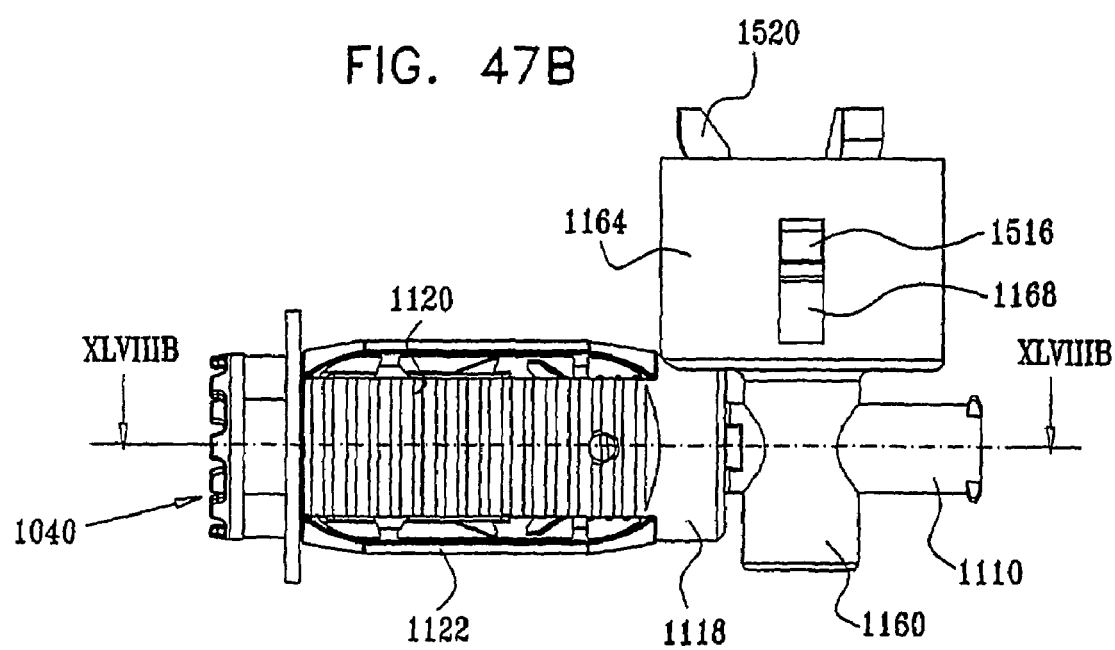
Figure 48A:
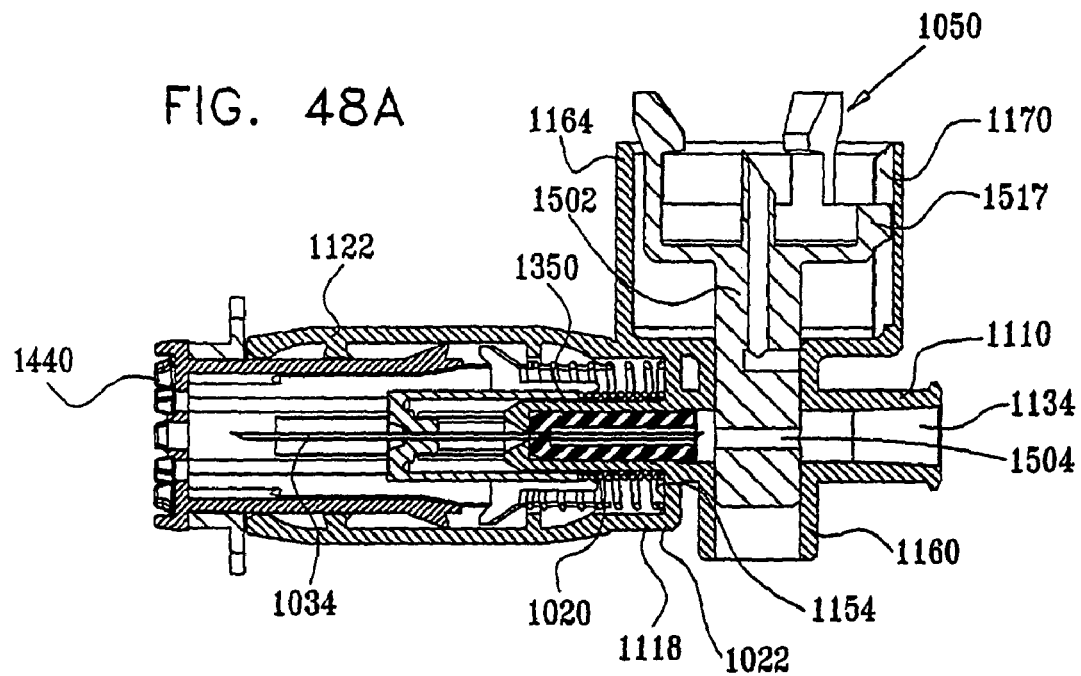
FIGS. 48A and 48B are sectional illustration taken along respective section lines and directions XLVIIIA-XLVIIIA and XLVIIIB-XLVIIIB in FIGS. 47A and 47B.
Figure 48B:
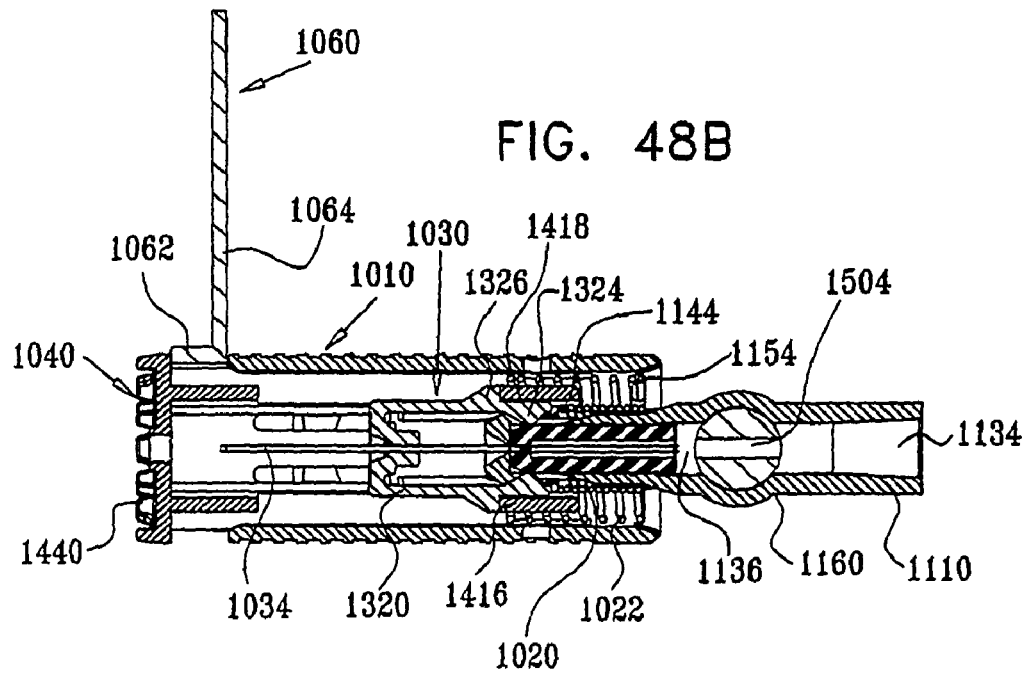

Reference is now made to FIGS. 46A and 46B, which are simplified assembled view illustrations of the medicinal container engagement and automatic needle device of FIG. 39 in a pre-use operative orientation, to FIGS. 47A and 47B, which are respective top and side view simplified planar illustrations thereof and to FIGS. 48A and 48B, which are sectional illustrations taken along respective section lines and directions XLVIIIA-XLVIIIA and XLVIIIB-XLVIIIB in FIGS. 47A and 47B.

As seen in FIGS. 46A-48B, in a pre-use operative orientation of the medicinal container engagement and automatic needle device, suitable for storage, the housing element 1010 is joined to the needle hub assembly 1030 by engagement of inner facing teeth 1324 into apertures 1144 formed in the cylindrical walls of bore 1136. First and second compression springs 1020 and 1022 are located mutually coaxially within housing element 1010.

Compression spring 1020 is maintained under compression between forward-facing back wall surface 1154 of generally cylindrical portion 1118 of housing element 1010 and a rearward facing wall portion 1350 of hub assembly 1030.

Compression spring 1022 is maintained under compression between forward facing back wall surface 1154 and rearward facing ends 1413 and 1415 of needle guard element 1040, which is slidably retained against forward movement by the positioning of curved rearward facing portions 1416 and 1418 thereof immediately rearward of teeth 1326 of needle hub assembly 1030.

The needle hub assembly 1030 is retained in place by engagement of outwardly facing surfaces of inner facing teeth 1324 of rearwardly extending arms 1320 and curved rearward facing portions 1416 and 1418 of needle guard element 1040. This prevents rearwardly extending arms 1320 of needle hub assembly 1030 from bending outwardly and releasing the engagement of inner facing teeth 1324 and apertures 1144 formed in the cylindrical walls of bore 1136 of the housing element 1010. The safety tab 1060 prevents the needle guard element 1040 from moving backwards and allowing needle penetration.

The two-position vial communication element 1050 is slidably seated in tubular portion 1160 of housing element 1010. Relative sliding motion between two-position vial communication element 1050 and housing element 1010 is provided by engagement of track riding protrusion 1517 of two-position vial communication element 1050 with track 1170 of housing element 1010. Additionally, engagement between slot engagement elements 1516 of two-position vial communication element 1050 with slots 1168 of housing element 1010 limits the axial displacement of the two-position vial communication element 1050 relative to the housing element 1010.

As seen with particular clarity in FIGS. 48A-48B, in the absence of engagement of a vial with two-position vial communication element 1050, the two-position vial communication element 1050 is in a position wherein bore 1504 is in a position whereby it provides liquid communication between a bore 1134 of tubular portion 1110 and needle 1034. It is appreciated that the cylindrical portion 1502 of two-position vial communication element 1050 and the tubular portion 1160 are constructed such that liquid sealing is provided therebetween, whereby liquid communicating between bore 1134 and needle 1034 does not reach the interior of cylindrical portion 1164 or leak out of tubular portion 1160.

Figure 49:
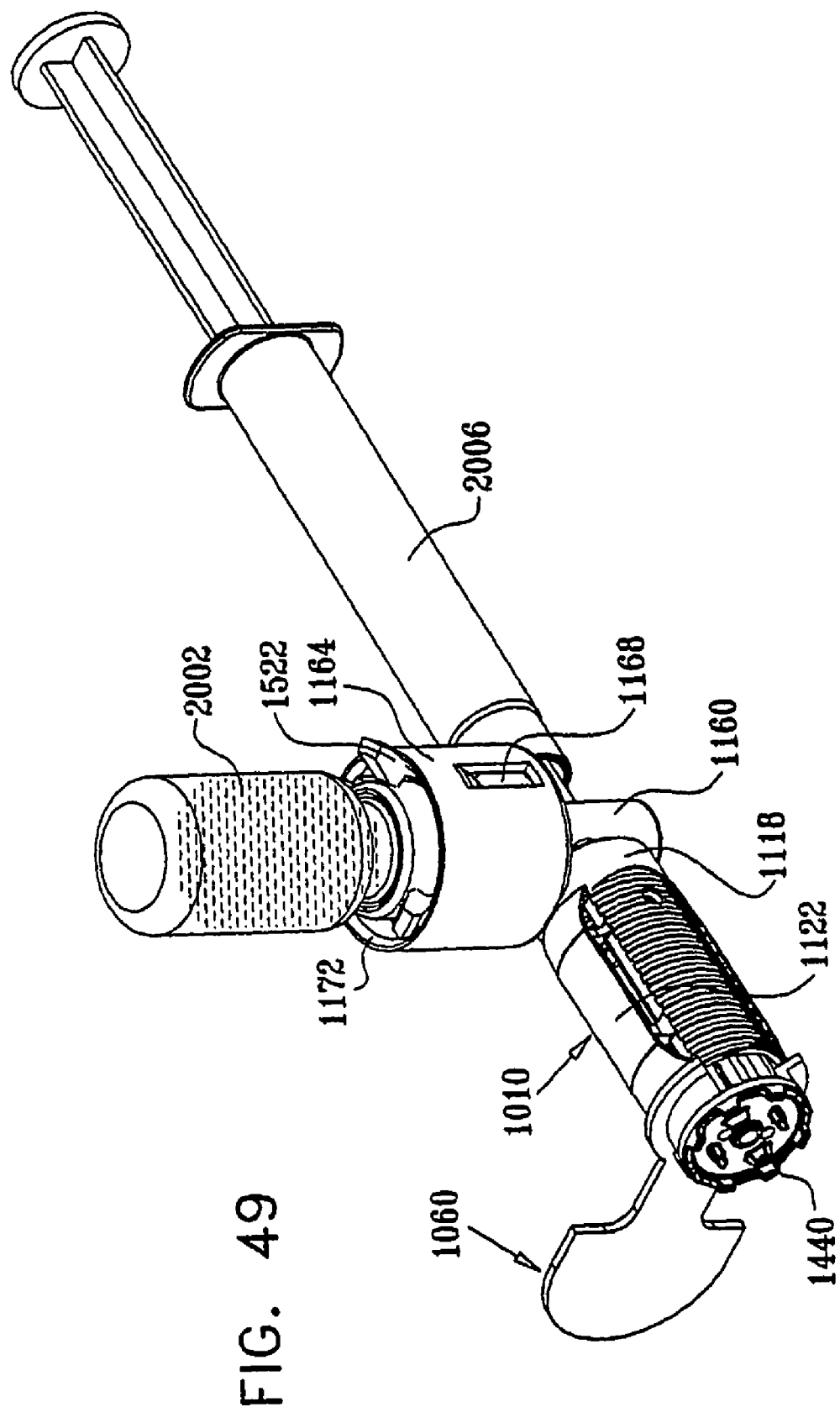
FIG. 49 is a simplified assembled view illustration of the medicinal container engagement and automatic needle device of FIG. 39 in a vial puncture operative orientation.

Reference is now made to FIG. 49, which is a simplified assembled view illustration of the medicinal container engagement and automatic needle device of FIG. 39 in a vial puncture operative orientation, to FIG. 50, which is a simplified top view planar illustration thereof and to FIG. 51, which is a sectional illustration taken along section lines LI-LI in FIG. 50.

As seen in FIGS. 49-51, upon initial insertion of a vial 2002 into engagement with two-position vial communication element 1050, the engagement of protrusions 1522 with edge 1172 of housing element 1010 causes the spike 1510 to puncture a vial stopper 2204.

Figure 52:
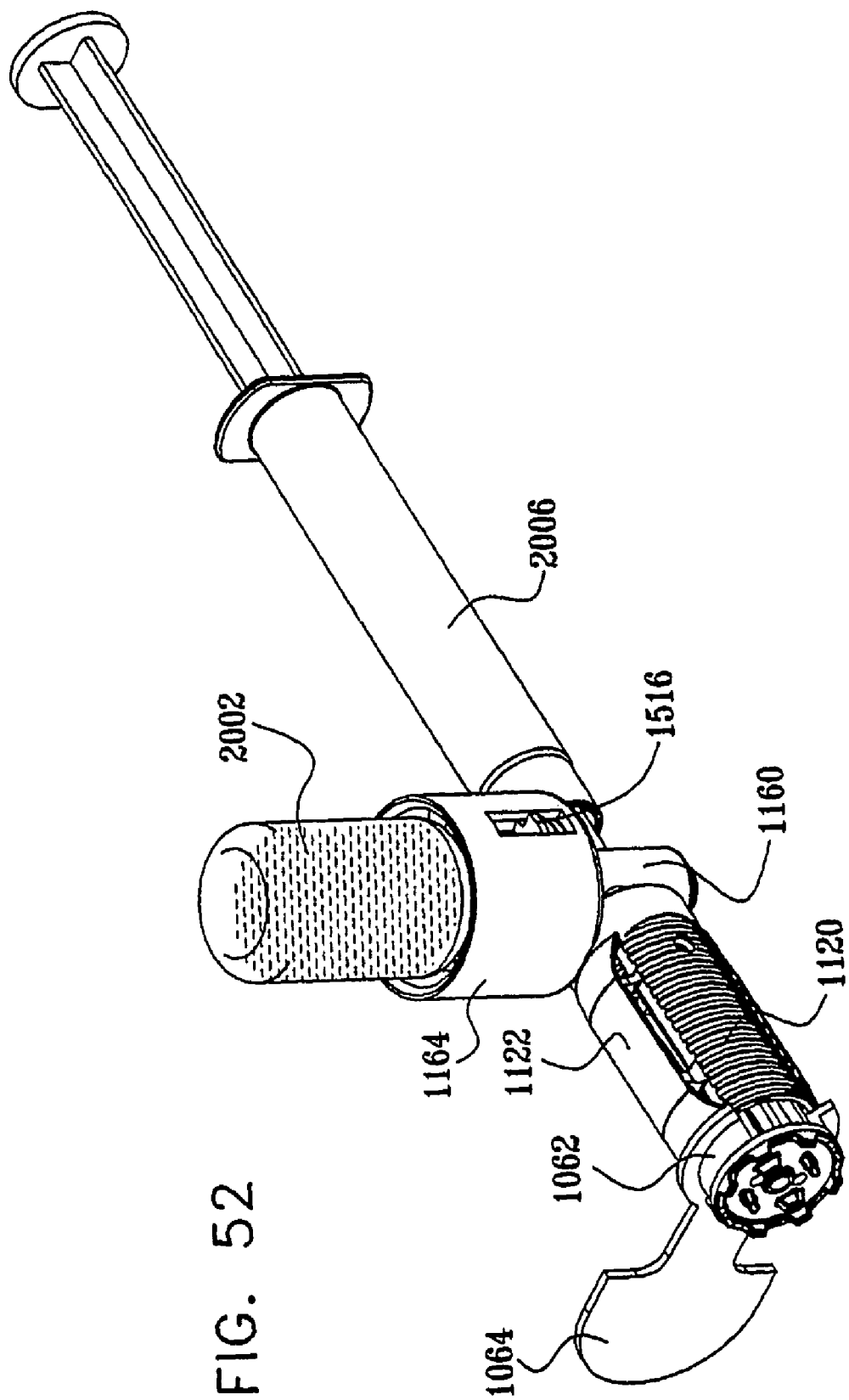
FIG. 52 is a simplified assembled view illustration of the medicinal container engagement and automatic needle device of FIG. 39 in vial attachment operative orientation.
Figure 53:
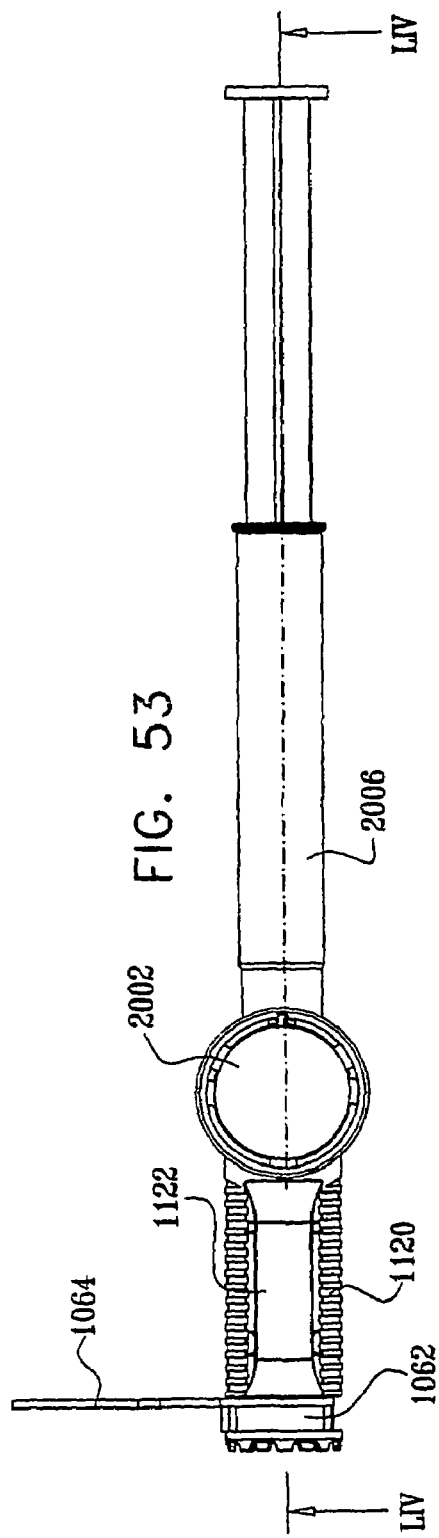
FIG. 53 is a simplified top view planar illustration of the medicinal container engagement and automatic needle device of FIG. 52.
Figure 54:
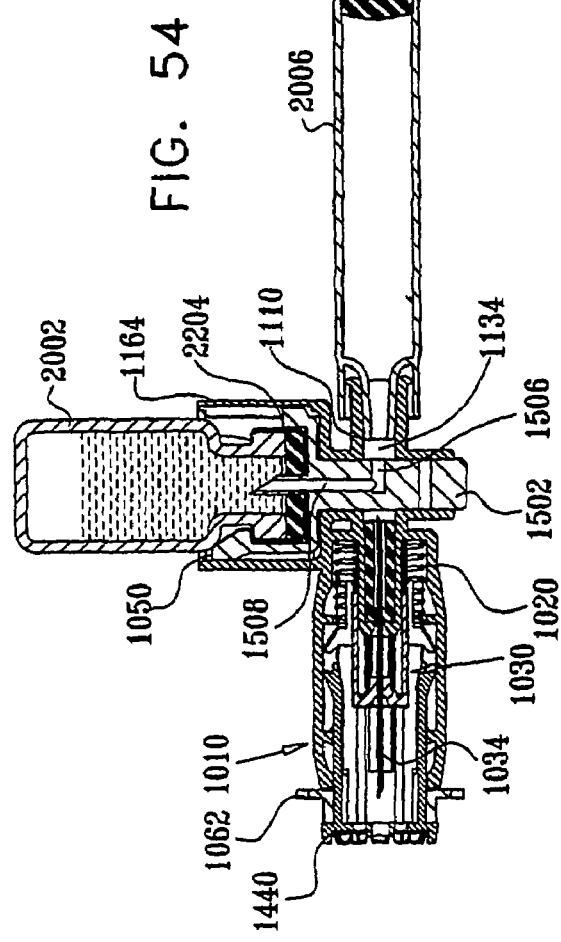
FIG. 54 is a sectional illustration taken along section lines LIV-LIV in FIG. 53.

Reference is now made to FIG. 52, which is a simplified assembled view illustration of the medicinal container engagement and automatic needle device of FIG. 39 in vial attachment operative orientation, to FIG. 53, which is a simplified top view planar illustration thereof and to FIG. 54, which is a sectional illustration taken along section lines LIV-LIV in FIG. 53.

As seen in FIGS. 52-54, only after puncturing of vial stopper 2204, does two-position vial communication element 1050 move axially to a position wherein liquid communication between bore 1134 of cylindrical portion 1110 and needle 1034 is terminated and liquid communication between bore 1134 and the interior of the vial 2002 via bores 1506 and 1508 is established. As noted above, it is appreciated that the cylindrical portion 1502 of two-position vial communication element 1050 and the tubular portion 1160 are constructed such that liquid sealing is provided therebetween, whereby liquid communicating between bore 1134 and the interior of vial 2002 does not reach the needle 1034 or leak out of tubular portion 1160.

Figure 55:
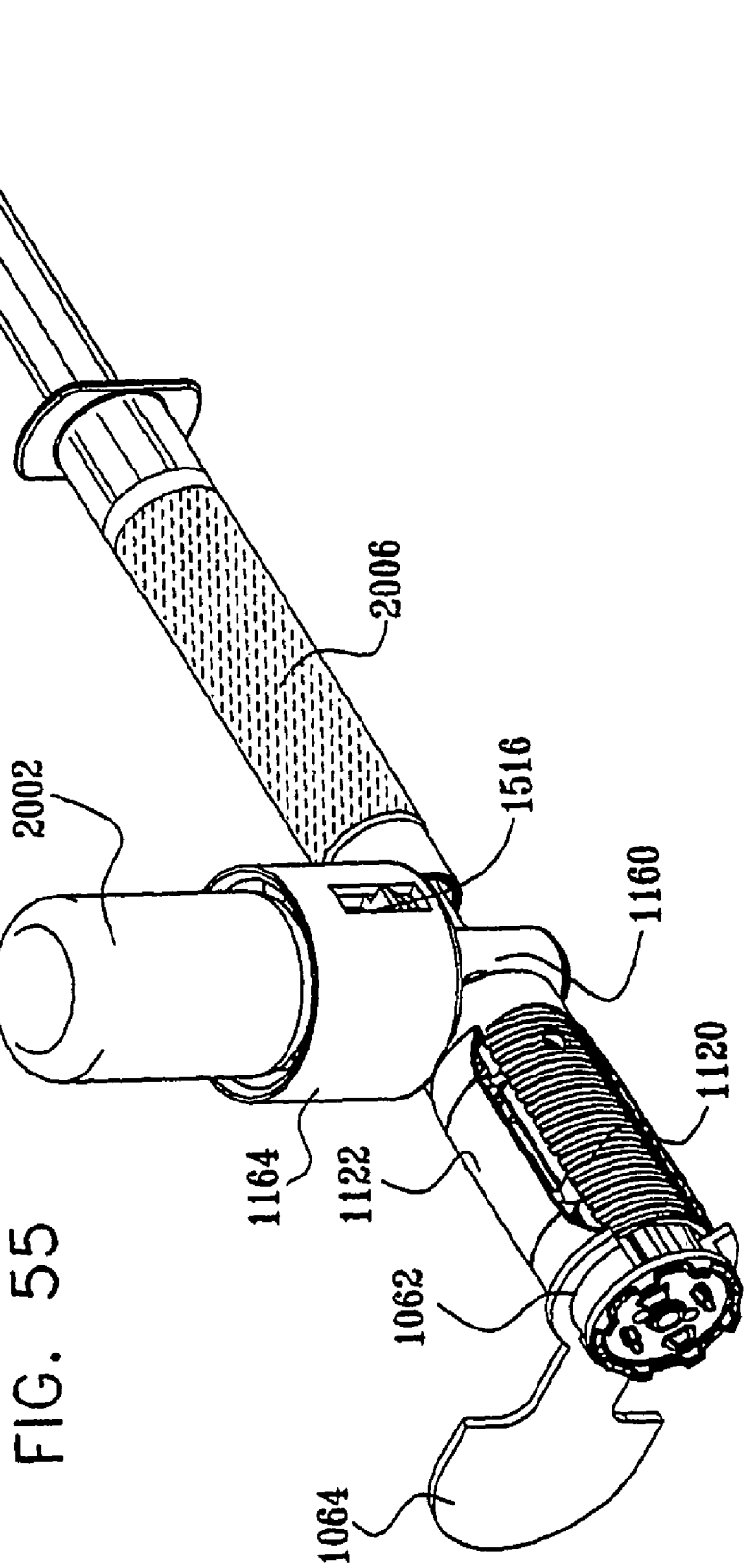
FIG. 55 is a simplified assembled view illustration of the medicinal container engagement and automatic needle device of FIG. 39 in a liquid drawing operative orientation.

Reference is now made to FIG. 55, which is a simplified assembled view illustration of the medicinal container engagement and automatic needle device of FIG. 39 in a liquid drawing operative orientation, to FIG. 56, which is a top view simplified planar illustration thereof and to FIG. 57, which is a sectional illustration taken along section lines LVII-LVII in FIG. 56. It is noted that the interior of a syringe 2006, coupled via cylindrical portion 1110 of housing element 1010 and bores 1506 and 1508, contains liquid drawn from the interior of vial 2002, supported in two-position vial engagement element, via spike 1510. This stage may take place after mixing liquid from multiple vials and/or reconstitution of lyophilized drugs.

Figure 58:
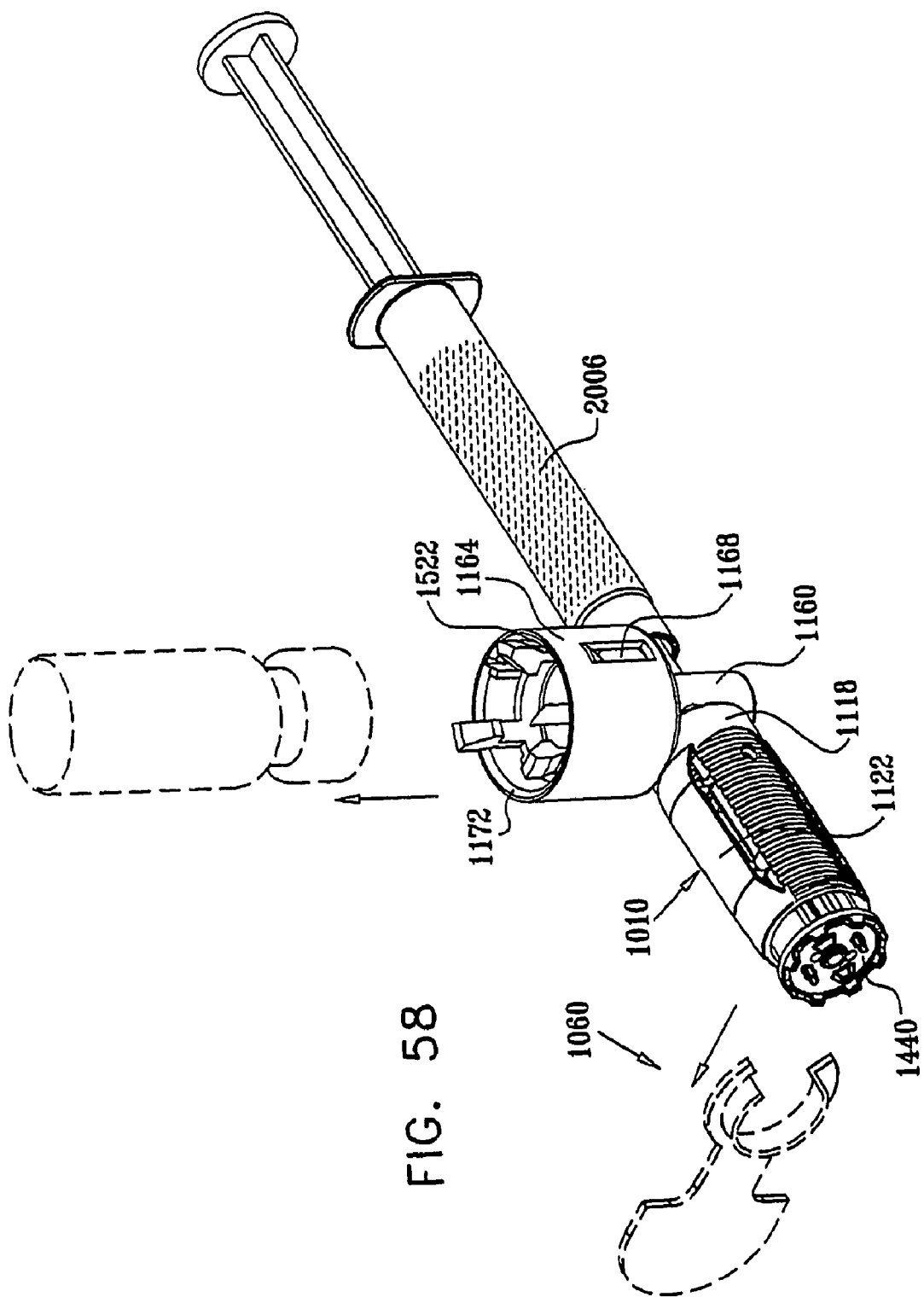
FIG. 58 is a simplified assembled view illustration of the medicinal container engagement and automatic needle device of FIG. 39 in a vial detachment operative orientation.

Reference is now made to FIG. 58, which is a simplified assembled view illustration of the medicinal container engagement and automatic needle device of FIG. 39 a vial detachment operative orientation, to FIG. 59, which is a simplified top view planar illustration thereof and to FIG. 60, which is a sectional illustration taken along section lines LX-LX in FIG. 59.

When a user seeks to remove vial 2002 from engagement with two-position vial communication element 1050, the engagement of protrusions 1520 of fingers 1518 with the neck of the vial 2002 causes the two-position vial communication element 1050 to be displaced axially to its pre-use orientation relative to cylindrical portion 1164, in an opposite manner to that described hereinabove with reference to FIGS. 49-54, such that once again bore 1504 is in a position whereby it provides liquid communication between bore 1134 of cylindrical portion 1110 and needle 1034.

As seen in FIGS. 58-60, due to the limitation of the axial displacement of the two-position vial communication element 1050 by engagement of slot engagement elements 1516 with slots 1168, after repositioning of the two-position vial communication element 1050, the spike 1510 is pulled out of the vial stopper 2204. At this stage the two-position vial communication element 1050 is in a position wherein liquid communication between bore 1134 of cylindrical portion 1110 and needle 1034 is established and liquid communication between bore 1134 and the interior of the vial 2002 via bores 1506 and 1508 is terminated. As noted above, it is appreciated that the cylindrical portion 1502 of two-position vial communication element 1050 and tubular portion 1160 are constructed such that liquid sealing is provided therebetween, whereby liquid communicating between bore 1134 and needle 1034 does not reach the interior of cylindrical portion 1164 or leak out of tubular portion 1160.

At this stage, a user may remove safety tab 1060 by pulling on tab portion 1064 such that tubular portion 1062 is removed from housing element 1010, thus enabling actuation of the automatic needle functionality of the medicinal container engagement and automatic needle device.

It is appreciated that once syringe 2006 contains the drug to be injected, the injection process is identical to that described hereinabove with reference to FIGS. 30-38B.

It will be appreciated by persons skilled in the art that the present invention is not limited to what has been particularly shown and described hereinabove. Rather the scope of the present invention includes both combinations and subcombinations of various features described hereinabove as well as modifications of such features which would occur to a person of ordinary skill in the art upon reading the foregoing description and which are not in the prior art.

The invention claimed is:

1. A medicinal container engagement and automatic needle device comprising:
   an automatic needle assembly including a needle and a first syringe adapter element; and
   a medicinal container receptacle including a second syringe adapter element, said medicinal container receptacle being removably joined by a break-away connection to said automatic needle assembly, said break-away connection including a safety element which prevents actuation of said automatic needle assembly while said medicinal container receptacle is joined to said automatic needle assembly,
   said first syringe adapter and said second syringe adapter being configured to receive an external syringe attached thereto.

2. A medicinal container engagement and automatic needle device according to claim 1 and wherein said first and second syringe adapter elements are located in a side by side mutual orientation.

3. A medicinal container engagement and automatic needle device according to claim 1 and wherein said first and second syringe adapter elements are located in a parallel mutual orientation.

4. A medicinal container engagement and automatic needle device according to claim 1 and wherein said automatic needle assembly comprises:
   a housing element;
   at least one resilient element arranged to be located within said housing element;
   at least one needle bearing element adapted, when actuated, to be displaced by said at least one resilient element with respect to said housing element from a non-penetration position to a penetration position; and
   a needle guard adapted for positioning with respect to said housing element and wherein displacement of said needle guard is operative to actuate displacement of said at least one needle bearing element from said non-penetration position to said penetration position.

5. A medicinal container engagement and automatic needle device according to claim 4 and wherein rearward displacement of said needle guard is operative to actuate displacement of said at least one needle bearing element from said non-penetration position to said penetration position.

6. A medicinal container engagement and automatic needle device according to claim 4 and also wherein said automatic needle assembly also comprises a safety element adapted to prevent inadvertent actuation of displacement of said at least one needle bearing element.

7. A medicinal container engagement and automatic needle device according to claim 6 and wherein said safety element prevents inadvertent rearward displacement of said needle guard.

8. A medicinal container engagement and automatic needle device according to claim 4 and wherein said at least one resilient element comprises a unitary resilient element.

9. A medicinal container engagement and automatic needle device according to claim 4 and wherein said at least one resilient element comprises first and second coil springs.

10. A medicinal container engagement and automatic needle device according to claim 4 and wherein said housing element includes an injection device engagement portion.

11. A medicinal container engagement and automatic needle device according to claim 10 and wherein said housing element and said at least one needle bearing element together define a fluid pathway from said injection device engagement portion through said needle at least when said needle bearing element is in both said non-penetration position and said penetration position.

12. A medicinal container engagement and automatic needle device according to claim 4 and wherein said needle guard is displaceable by said at least one resilient element.

13. A medicinal container engagement and automatic needle device according to claim 4 and wherein said at least one resilient element comprises first and second compression springs which provide selectable forward displacement to said at least one needle bearing element.

14. A medicinal container engagement and automatic needle device according to claim 4 and wherein said needle bearing element includes a hub portion and said a needle is adhered thereto and extends through a septum.

15. A medicinal container engagement and automatic needle device according to claim 4 and wherein said automatic needle assembly also comprises a safety tab operative for disabling actuation of the automatic needle device.

16. A medicinal container engagement and automatic needle device according to claim 15 and wherein said safety tab includes a spacer portion and a tab portion.

17. A medicinal container engagement and automatic needle device according to claim 4 and wherein said housing element is an integrally formed element having a generally cylindrical configuration and is generally side-to-side symmetric about a longitudinal axis.

18. A medicinal container engagement and automatic needle device according to claim 4 and wherein said housing element includes a rearward generally tubular portion which terminates in an open back and defines forwardly thereof a generally cylindrical portion, whose outer configuration includes top and bottom grip regions.

19. A medicinal container engagement and automatic needle device according to claim 18 and wherein said automatic needle assembly comprises at an inner surface of said generally cylindrical portion forward and rearward inwardly extending transverse ribs and a plurality of inwardly extending longitudinal slots.

20. A medicinal container engagement and automatic needle device according to claim 18 and wherein a forward-facing back wall surface of said generally cylindrical portion defines a seat for said at least one resilient element.

21. A medicinal container engagement and automatic needle device according to claim 4 and wherein said housing element includes first and second forwardly and rearwardly tapered side protrusions.

22. A medicinal container engagement and automatic needle device according to claim 4 and wherein said automatic needle assembly comprises at an interior of a generally tubular portion thereof, a generally cylindrical bore which communicates via a tapered interface with a forward bore, disposed interiorly of a cylindrical portion, said cylindrical bore being arranged to receive a septum.

23. A medicinal container engagement and automatic needle device according to claim 4 and wherein said housing element is formed with a pair of side-to-side symmetric windows, to allow viewing of the tip of said a-needle held by said needle bearing element.

24. A medicinal container engagement and automatic needle device according to claim 4 and wherein said needle bearing element comprises a needle hub and a said needle.

25. A medicinal container engagement and automatic needle device according to claim 24 and wherein said needle bearing element has a generally cylindrical configuration and is top-to-bottom and side-to-side symmetric about a longitudinal axis.

26. A medicinal container engagement and automatic needle device according to claim 24 and wherein said needle bearing element defines a generally tubular body having formed thereon a pair of up-down mutually spaced, forwardly facing, outwardly extending hook protrusions.

27. A medicinal container engagement and automatic needle device according to claim 26 and wherein a rearwardly extending arm is formed at both a top and a bottom of said tubular body, each arm including, adjacent an extreme rearwardly facing end thereof, a tapered inwardly facing tooth and forwardly thereof an outwardly facing tooth, having a transversely extending rearwardly facing surface.

28. A medicinal container engagement and automatic needle device according to claim 26 and wherein top and bottom pairs of outwardly facing ribs are formed on said tubular portion, adjacent respective rearward facing ribs, said outwardly facing ribs being operative to slidably locate said needle bearing element within said needle guard.

29. A medicinal container engagement and automatic needle device according to claim 26 and wherein said tubular body defines a generally open back and a forward facing wall portion adjacent in which is formed a recess, which communicates with a narrow axial bore, arranged to receive said needle, which extends therethrough.

30. A medicinal container engagement and automatic needle device according to claim 26 and wherein a rearward facing external wall portion, located at a rearward end of said tubular body, defines a seat for said at least one resilient element.

31. A medicinal container engagement and automatic needle device according to claim 4 and wherein said needle guard has a generally cylindrical configuration and is top-to-bottom and side-to-side symmetric about a longitudinal axis.

32. A medicinal container engagement and automatic needle device according to claim 4 and wherein said needle guard defines a generally tubular body having formed thereon a plurality of circumferentially spaced, longitudinally extending, outward facing ribs, having rearward facing ends, said outward facing ribs being adapted to slidably locate said needle guard within inwardly extending longitudinal slots of said housing element.

33. A medicinal container engagement and automatic needle device according to claim 32 and wherein extending rearwardly of said outwardly facing ribs there is provided a curved rearward facing portion having a pair of inwardly facing slots formed therein, and, extending rearwardly of said ribs, there is formed a symmetrically curved rearward facing portion having a pair of ribs formed therein.

34. A medicinal container engagement and automatic needle device according to claim 33 and wherein said curved rearward facing portions together with said rearward facing ends define a seat for a spring forming part of said at least one resilient element.

35. A medicinal container engagement and automatic needle device according to claim 33 and wherein said inwardly facing slots are operative to slidably locate said needle bearing element within said needle guard, by allowing said outwardly facing ribs to slide therein.

36. A medicinal container engagement and automatic needle device according to claim 32 and wherein a rearwardly extending arm is formed at each side of said tubular body, each of said arms including adjacent an extreme rearwardly facing end thereof, an outwardly facing tooth, having an inclined forward surface and a transversely extending rearwardly facing surface.

37. A medicinal container engagement and automatic needle device according to claim 32 and wherein said tubular body defines a generally open back and a forward facing wall portion, defining an injection site engagement surface.

38. A medicinal container engagement and automatic needle device according to claim 37 and wherein said injection site engagement surface includes a pair of mutually concentric circles of mutually spaced forwardly extending protrusions and said forward facing wall portion is formed with an axial bore, arranged to allow said needle to extend therethrough.

39. A medicinal container engagement and automatic needle device according to claim 4 and wherein said needle guard is formed with a pair of side-to-side symmetric windows, to allow viewing of the tip of said needle.

40. A medicinal container engagement and automatic needle device according to claim 4 and wherein, in a pre-use operative orientation suitable for storage, said housing element is joined to said needle bearing element by snap fit engagement of inner facing teeth formed on said needle bearing element into apertures formed in cylindrical walls of said housing element.

41. A medicinal container engagement and automatic needle device according to claim 40 and wherein said at least one resilient element comprises first and second compression springs, said first compression spring being maintained under compression between forward-facing back wall surface of a generally cylindrical portion of said housing element and a rearward facing wall portion of said needle bearing element and said second compression spring being maintained under compression between said forward facing back wall surface and rearward facing ends of said needle guard, which is slidably retained against disassembly forward movement by the positioning of curved rearward facing portions thereof immediately rearward of said inner facing teeth of said needle bearing element.

42. A medicinal container engagement and automatic needle device according to claim 40 and wherein said needle bearing element is retained in its place by engagement of rearwardly outwardly facing surfaces of said inner facing teeth with curved rearward facing portions of said needle guard, thus preventing rearwardly extending arms of said needle bearing element from bending outwardly and releasing the snap fit engagement of said inner facing teeth and apertures formed in the cylindrical walls of said cylindrical bore of said housing element.

43. A medicinal container engagement and automatic needle device according to claim 40 and wherein due to engagement of said needle guard with an injection site on a body, said needle guard is forced, against the urging of said at least one resilient element, to move axially in a rearward direction with respect to the remainder of the automatic needle device, thus sliding said curved rearward facing portions thereof further rearward of said outwardly facing teeth of said needle bearing element, thus allowing said arms of said needle bearing element to cantilever outwardly.

44. A medicinal container engagement and automatic needle device according to claim 40 and wherein at all times said needle sealingly and slidably engages a septum.

45. A medicinal container engagement and automatic needle device according to claim 1 and wherein said automatic needle assembly comprises:
 a housing element;
 at least one needle bearing element adapted, when actuated, to be displaced with respect to said housing element from a non-penetration position to a penetration position; and
 a needle guard adapted for positioning with respect to said at least one needle bearing element and with respect to said housing element in a mutually locked needle guarding orientation, whereby displacement of said needle guard in a first direction relative to said housing is prevented by engagement of said needle guard with said at least one needle bearing element and displacement of said needle guard in a second direction relative to said housing, opposite to said first direction, is prevented by engagement of said needle guard with said housing element.

46. A medicinal container engagement and automatic needle device comprising:
 an automatic needle assembly including a needle; and
 a medicinal container receptacle removably joined to said automatic needle assembly, said medicinal container receptacle comprising a break-away connection joining said automatic needle assembly to said medicinal container receptacle, said break-away connection including a safety element which prevents actuation of said automatic needle assembly while said medicinal container receptacle is joined to said automatic needle assembly.

\* \* \* \* \*